(12) United States Patent
Ates et al.

(10) Patent No.: US 10,370,355 B2
(45) Date of Patent: Aug. 6, 2019

(54) TETRAHYDROISOQUINOLINE DERIVATIVES

(71) Applicant: UCB Biopharma SPRL, Brussels (BE)

(72) Inventors: Ali Ates, Brussels (BE); Eric Jnoff, Brussels (BE); Laurent Provins, Brussels (BE); Anne Valade, Brussels (BE); Adrian Hall, Brussels (BE)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 16/086,698

(22) PCT Filed: Apr. 7, 2017

(86) PCT No.: PCT/EP2017/058422
§ 371 (c)(1),
(2) Date: Sep. 20, 2018

(87) PCT Pub. No.: WO2017/178377
PCT Pub. Date: Oct. 19, 2017

(65) Prior Publication Data
US 2019/0106406 A1    Apr. 11, 2019

(30) Foreign Application Priority Data
Apr. 13, 2016  (EP) .................... 16165012

(51) Int. Cl.
C07D 401/06 (2006.01)
C07D 471/04 (2006.01)

(52) U.S. Cl.
CPC ......... C07D 401/06 (2013.01); C07D 471/04 (2013.01)

(58) Field of Classification Search
None
See application file for complete search history.

(56) References Cited

FOREIGN PATENT DOCUMENTS
WO    2016/055479    4/2016

OTHER PUBLICATIONS
CAPLUS 1974:83355.*
(Continued)

Primary Examiner — Heidi Reese
(74) Attorney, Agent, or Firm — McDonnell Boehnen Hulbert & Berghoff LLP

(57) ABSTRACT

The present invention relates to tetrahydroisoquinoline derivatives according to formula (I), wherein G represents a fused heterocyclic system selected from the groups represented by formula ($G^1$), ($G^2$), ($G^3$), ($G^4$), ($G^5$), and ($G^6$), which are Positive Allosteric Modulators of D1 and accordingly of benefit as pharmaceutical agents for the treatment of diseases in which D1 receptors play a role.

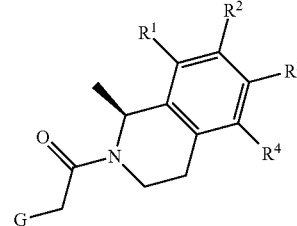

(I)

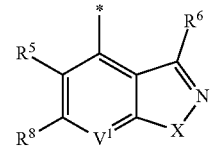

($G^1$)

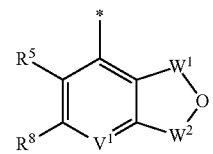

($G^2$)

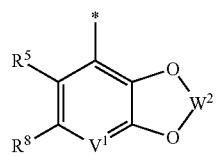

($G^3$)

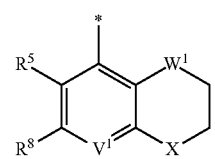

($G^4$)

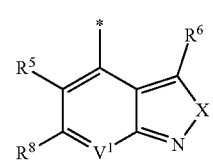

($G^5$)

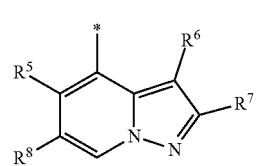

($G^6$)

17 Claims, No Drawings

(56) References Cited

OTHER PUBLICATIONS

Conn et al., "Allosteric modulators of GPCRs: a novel approach for the treatment of CNS disorders," Nature Reviews Drug Discovery, vol. 8, No. 1, Jan. 1, 2009, pp. 41-54.
International Search Report dated May 11, 2017 for International Application No. PCT/EP2017/058422, 2 pages.

* cited by examiner

TETRAHYDROISOQUINOLINE DERIVATIVES

This application is the US national phase under 35 U.S.C. § 371 of international application PCT/EP2017/058422, filed Apr. 7, 2017, which claims priority to European application 16165012.2, filed Apr. 13, 2016.

The invention relates to tetrahydroisoquinoline derivatives and their use in therapy. In particular the present invention relates to pharmacologically active fused heterocyclic tetrahydroisoquinoline derivatives and analogs thereof. More particularly, the present invention relates to substituted 3,4-dihydroisoquinol-2(1H)-yl derivatives and analogs thereof.

The compounds according to the present invention are D1 Positive Allosteric Modulators and accordingly of benefit as pharmaceutical agents for the treatment of diseases in which D1 receptors play a role.

The monoamine dopamine acts via two families of GPCRs to modulate motor function, reward mechanisms, cognitive processes and other physiological functions. Specifically, dopamine is acting upon neurons via D1-like, comprising dopamine D1 and D5, receptors which couple mainly to the $G_s$ G-protein and thereby stimulate cAMP production, and D2-like, which comprise D2, D3 and D4, receptors which couple to $G_{i/q}$ G-proteins and which attenuate cAMP production. These receptors are widely expressed in different brain regions. In particular, D1 receptors are involved in numerous physiological functions and behavioural processes. D1 receptors are, for instance, involved in synaptic plasticity, cognitive function and goal-directed motor functions, but also in reward processes. Due to their role in several physiological/neurological processes, D1 receptors have been implicated in a variety of disorders including cognitive and negative symptoms in schizophrenia, cognitive impairment related to classical antipsychotic therapy, impulsivity, attention disorder with hyperactivity (ADHD), Parkinson's disease and related movement disorders, dystonia, Huntington's disease, dementia with Lewy Body, Alzheimer's disease, age-related cognitive decline, mild cognitive impairment (MCI), drug addiction sleep disorders, apathy.

It has proven difficult to develop orally-bioavailable small molecules targeting D1 receptors. D1 agonists developed so far are generally characterized by a catechol moiety and their clinical use has therefore been limited to invasive therapies. Achieving sufficient selectivity has also been challenging due to the high degree of homology in the ligand binding site between dopamine receptors subtypes (e.g. dopamine D1 and D5). Also, D1 agonists are associated with potentially limiting side effects including but not limited to dyskinesia and hypotension.

There is therefore a need to design new agents that could modulate D1 receptors.

There has been much interest in the identification of allosteric modulators of GPCRs, both as tools to understand receptor mechanisms and as potential therapeutic agents. GPCRs represent the largest family of cell-surface receptors and a large number of marketed drugs directly activate or block signaling pathways mediated by these receptors. However, for some GPCRs (e.g. peptide receptors), it has proven challenging to develop small molecules or to achieve sufficient selectivity due to the high degree of homology in the ligand binding site between subtypes (e.g. dopamine D1 and D5 or D2 and D3). Accordingly, much drug research has shifted to the identification of small molecules which target sites distinct from the orthosteric natural agonist. Ligands which bind to these sites induce a conformational change in the GPCR thereby allosterically modulating the receptor function. Allosteric ligands have a diverse range of activities including the ability to potentiate (positive allosteric modulator, PAM) or attenuate (negative allosteric modulator, NAM) the effects of the endogenous ligand, by affecting affinity and/or efficacy. As well as subtype selectivity, allosteric modulators can present other potential advantages from a drug discovery perspective such as a lack of direct effect or intrinsic efficacy; only potentiating the effect of the native transmitter where and when it is released; reduced propensity for inducing desensitization arising from constant exposure to an agonist as well as reduced propensity to induce target-related side-effects.

The compounds according to the present invention potentiate the effect of D1 agonists or of the endogenous ligand on D1 receptors through an allosteric mechanism, and are therefore D1 positive allosteric modulators (D1 PAM).

The compounds in accordance with the present invention, being D1 PAM, are therefore beneficial in the treatment and/or prevention of diseases and disorders in which D1 receptors play a role. Such diseases include cognitive and negative symptoms in schizophrenia, cognitive impairment related to classical antipsychotic therapy, impulsivity, attention disorder with hyperactivity (ADHD), Parkinson's disease and related movement disorders, dystonia, Huntington's disease, dementia with Lewy Body, Alzheimer's disease, age-related cognitive decline, mild cognitive impairment (MCI), drug addiction, sleep disorders and apathy.

International patent application WO 2013/051869 A1 discloses certain 3,4-dihydro-1H-isoquinolin-2-yl derivatives which are NK2 antagonists.

International patent application WO 2008/109336 A1 discloses certain tetrahydroisoquinoline compounds which are modulators of the histamine H3 receptors.

International patent application WO 2014/193781 A1, published Dec. 4, 2014, discloses certain 3,4-dihydroisoquinolin-2(1H)-yl derivatives useful for the treatment of cognitive impairment associated with Parkinson's disease or Schizophrenia.

Co-pending international patent application WO2016/055482 relates to 1,3-dihydroisoindolin-2(1H)-yl derivatives and analogs thereof which may be useful for the treatment of diseases in which D1 receptors play a role.

Co-pending international patent application WO2016/055479 relates to substituted 3,4-dihydroisoquinolin-2(1H)-yl derivatives and analogs thereof which may be useful for the treatment of diseases in which D1 receptors play a role.

None of the prior art available to date, however, discloses or suggests the precise structural class of fused heterocyclic tetrahydroisoquinoline derivatives as provided by the present invention.

The present invention provides a compound of formula (I), or a pharmaceutically acceptable salt thereof,

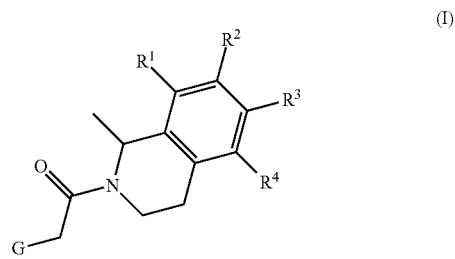

wherein

R$^1$, R$^2$ and R$^3$ represent independently hydrogen, halogen or cyano; or R$^1$, R$^2$ and R$^3$ represent independently C$_{1-6}$ alkyl or C$_{1-6}$ alkoxy, either of which groups may be optionally substituted by one or more substitutents;

R$^4$ represents —N=S(O)R$^a$R$^b$; or R$^4$ represents C$_{1-6}$ alkyl, C$_{1-6}$ alkoxy, C$_{3-8}$ cycloalkyl or C$_{3-7}$heterocycloalkyl, each of these groups which may be optionally substituted by one or more substitutents;

R$^a$ and R$^b$ represent independently C$_{1-6}$ alkyl, which group may be optionally substituted by one or more substitutents; or R$^a$ and R$^b$ are linked together to form with the S atom to which they are attached a C$_{3-7}$ heterocycloalkyl, which group may be optionally substituted by one or more substitutents;

G represents a fused heterocyclic system selected from the groups represented by formula (G$^1$), (G$^2$), (G$^3$), (G$^4$), (G$^5$), and (G$^6$),

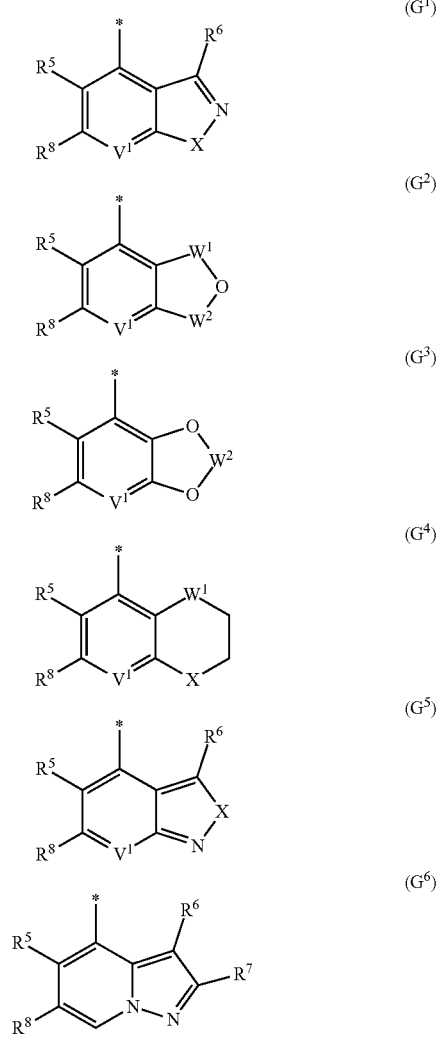

wherein
the asterisk (*) represents the point of attachment of G to the remainder of the molecule;
V$^1$ represents CH or N;
W$^1$ and W$^2$ represent independently CR$^9$R$^{10}$;
X represents O or NR$^{11}$;

R$^5$ represents halogen or cyano; or R$^5$ represents C$_{1-6}$ alkyl or C$_{1-6}$ alkoxy, either of which group may be optionally substituted by one or more substitutents;

R$^6$ and R$^7$ represent independently hydrogen, halogen or cyano; or R$^6$ and R$^7$ represent independently C$_{1-6}$ alkyl or C$_{1-6}$ alkoxy, either of these groups which may be optionally substituted by one or more substituents;

R$^8$ represents hydrogen, halogen or cyano; or R$^8$ represents independently C$_{1-6}$ alkyl, C$_{3-8}$ cycloalkyl or C$_{1-6}$ alkoxy, either of these groups which may be optionally substituted by one or more substituents;

R$^9$ and R$^{10}$ represent independently hydrogen or halogen; or R$^9$ and R$^{10}$ represent independently C$_{1-6}$ alkyl, which group may be optionally substituted by one or more substituents; and R$^{11}$ represents hydrogen; or R$^{11}$ represents C$_{1-6}$ alkyl, which group may be optionally substituted by one or more substitutents.

The present invention also provides a compound of formula (I) as defined above or a pharmaceutically acceptable salt thereof, for use in therapy.

In another aspect, the present invention also provides a compound of formula (I) as defined above, or a pharmaceutically acceptable salt thereof, for use in the treatment and/or prevention of diseases and/or disorders in which D1 receptors play a role.

In another aspect, the present invention provides a compound of formula (I) as defined above, or a pharmaceutically acceptable salt thereof, for use in the treatment and/or prevention of cognitive and negative symptoms in schizophrenia, cognitive impairment related to classical antipsychotic therapy, impulsivity, attention disorder with hyperactivity (ADHD), Parkinson's disease and related movement disorders, dystonia, Huntington's disease, dementia with Lewy Body, Alzheimer's disease, age-related cognitive decline, mild cognitive impairment (MCI), drug addiction, sleep disorders or apathy.

In a particular aspect, the present invention provides a compound of formula (I) as defined above, or a pharmaceutically acceptable salt thereof, for use in the treatment and/or prevention of Parkinson's disease.

In a further aspect, the present invention provides for the use of a compound of formula (I) as defined above, or a pharmaceutically acceptable salt thereof, for the manufacture of a medicament useful for the treatment and/or prevention of diseases and/or disorders in which D1 receptors play a role.

In another further aspect, the present invention provides for the use of a compound of formula (I) as defined above, or a pharmaceutically acceptable salt thereof, for the manufacture of a medicament useful for the treatment and/or prevention of cognitive and negative symptoms in schizophrenia, cognitive impairment related to classical antipsychotic therapy, impulsivity, attention disorder with hyperactivity (ADHD), Parkinson's disease and related movement disorders, dystonia, Huntington's disease; dementia with Lewy Body, Alzheimer's disease, age-related cognitive decline, mild cognitive impairment (MCI), drug addiction, sleep disorders or apathy.

In a particular aspect, the present invention provides for the use of a compound of formula (I) as defined above, or a pharmaceutically acceptable salt thereof, for the manufacture of a medicament useful for the treatment and/or prevention of Parkinson's disease.

The present invention also provides a method for the treatment and/or prevention of disorders for which the administration of D1 positive allosteric modulator is indicated, which comprises administering to a patient in need of such treatment an effective amount of a compound of formula (I) as defined above, or a pharmaceutically acceptable salt thereof.

In another aspect, the present invention provides a method for the treatment and/or prevention of cognitive and negative symptoms in schizophrenia, cognitive impairment related to classical antipsychotic therapy, impulsivity, attention disorder with hyperactivity (ADHD), Parkinson's disease and related movement disorders, dystonia, Huntington's disease, dementia with Lewy Body, Alzheimer's disease, age-related cognitive decline, mild cognitive impairment (MCI), drug addiction, sleep disorders or apathy which comprises administering to a patient in need of such treatment an effective amount of a compound of formula (I) as defined above, or a pharmaceutically acceptable salt thereof.

In a particular aspect, the present invention provides a method for the treatment and/or prevention of Parkinson's disease, which comprises administering to a patient in need of such treatment an effective amount of a compound of formula (I) as defined above, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one or two substituents. Suitable substitutents for each particular groups of compounds formula (I) are further described here after in the present specification.

The present invention includes within its scope salts of the compounds of formula (I) above. For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Compounds according to the present invention may exist in different polymorphic forms. Although not explicitly indicated in the above formula, such forms are intended to be included within the scope of the present invention.

The invention also includes within its scope pro-drug forms of the compounds of formula (I) and its various sub-scopes and sub-groups.

The term "$C_{1-6}$ alkyl" as used herein refers to aliphatic hydrocarbon groups which may be straight or branched and may comprise 1 to 6 carbon atoms in the chain. Suitable alkyl groups which may be present on the compounds of use in the invention include straight-chained and branched $C_{1-4}$ alkyl groups. Illustrative $C_{1-6}$ alkyl goups include methyl and ethyl groups, and straight-chained or branched propyl and butyl and pentyl groups. Suitable alkyl groups include methyl, ethyl, n-propyl, and isopropyl.

The term "$C_{1-6}$ alkoxy" refers to a group of formula —O—R where R is an optionally substituted "$C_{1-6}$ alkyl". Suitable alkoxy groups according to the present invention include methoxy and ethoxy.

The term "(halo)$C_{1-6}$-alkyl", as used herein, refers to a $C_{1-6}$-alkyl as defined here above which is substituted by one or more halogen. Examples of (halo)$C_{1-6}$-alkyl group according to the present invention include fluoromethyl and difluoromethyl.

The term "$C_{3-8}$ cycloalkyl" as used herein refers to monovalent groups of 3 to 8 carbon atoms derived from a saturated monocyclic hydrocarbon. Illustrative $C_{3-8}$ cycloalkyl groups include cyclopropyl, cyclobutyl, cyclopentyl and cyclohexyl.

The term "$C_{3-7}$ heterocycloalkyl" as used herein refers to saturated monocyclic rings containing 3 to 7 carbon atoms and at least one heteroatom selected from oxygen, sulphur and nitrogen. Examples of $C_{3-7}$ heterocycloalkyl groups include oxetanyl, azetidinyl, pyrrolidinyl and piperidinyl.

The term "aryl" as used herein, refers to an unsaturated aromatic carbocyclic group of from 6 to 14 carbon atoms having a single ring (e.g. phenyl) or multiple condensed rings (e.g. naphthyl).

The term "heteroaryl" as used herein represents aromatic carbocyclic groups of from 5 to 14 carbon atoms having a single ring or multiple condensed rings, wherein one or more of the said carbon atoms have been replaced by one or more heteroatoms selected from oxygen, sulphur and nitrogen.

The term amino as used herein refers to a group of formula —$NH_2$.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise.

Some of the compounds of formula (I) may also exist in tautomeric forms. Such forms although not explicity indicated in the above formula are intended to be included within the scope of the present invention. Examples of tautomers include keto ($CH_2C=O$)↔-enol (CH=CHOH) tautomers or amide (NHC=O)↔-hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formula depicted hereinafter, may in fact be present in the form of any of its naturally occurring isotopes, with the most abundant isotope(s) being preferred. Thus, by way of example, each individual hydrogen atom present in formula (I), or in the formula depicted hereinafter, may be present as a $^1H$, $^2H$ (deuterium) or $^3H$ (tritium) atom, preferably $^1H$ or $^2H$. Similarly, by way of example, each individual carbon atom present in formula (I), or in the formulae depicted hereinafter, may be present as a $^{12}C$, $^{13}C$ or $^{14}C$ atom, preferably $^{12}C$.

A particular sub-class of compounds in accordance with the present invention is sub-class of compounds represented by formula (IA),

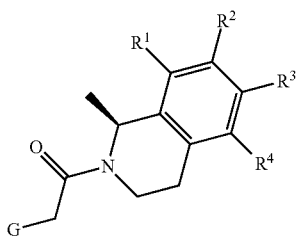
(IA)

wherein $R^1$, $R^2$, $R^3$, $R^4$ and G are as defined here above for compounds of formula (I).

In a first embodiment, $R^1$ represents hydrogen. In a second embodiment, $R^1$ represents halogen. In a first aspect of this embodiment, $R^1$ represents chloro. In a second aspect of this embodiment, $R^1$ represents bromo. In a third aspect of this embodiment, $R^1$ represents fluoro. In a third embodiment, $R^1$ represents cyano. In a fourth embodiment, $R^1$ represents optionally substituted $C_{1-6}$ alkyl. In one aspect of that embodiment, $R^1$ represents optionally substituted methyl. In a fifth embodiment, $R^1$ represents optionally substituted $C_{1-6}$ alkoxy. In one aspect of that embodiment, $R^1$ represents optionally substituted methoxy.

In a first embodiment, $R^2$ represents hydrogen. In a second embodiment, $R^2$ represents halogen. In a first aspect of this embodiment, $R^2$ represents chloro. In a second aspect of this embodiment, $R^2$ represents bromo. In a third aspect of this embodiment, $R^2$ represents fluoro. In a third embodiment, $R^2$ represents cyano. In a fourth embodiment, $R^2$ represents optionally substituted $C_{1-6}$ alkyl. In one aspect of that embodiment, $R^2$ represents optionally substituted methyl. In a fifth embodiment, $R^2$ represents optionally substituted $C_{1-6}$ alkoxy. In one aspect of that embodiment, $R^2$ represents optionally substituted methoxy.

In a first embodiment, $R^3$ represents hydrogen. In a second embodiment, $R^3$ represents halogen. In a first aspect of this embodiment, $R^3$ represents chloro. In a second aspect of this embodiment, $R^3$ represents bromo. In a third aspect of this embodiment, $R^3$ represents fluoro. In a third embodiment, $R^3$ represents cyano. In a fourth embodiment, $R^3$ represents optionally substituted $C_{1-6}$ alkyl. In one aspect of that embodiment, $R^3$ represents optionally substituted methyl. In a fifth embodiment, $R^3$ represents optionally substituted $C_{1-6}$ alkoxy. In one aspect of that embodiment, $R^3$ represents optionally substituted methoxy.

Suitably, $R^1$, $R^2$ and $R^3$ represent independently hydrogen, halogen or cyano; or $R^1$, $R^2$ and $R^3$ represent independently unsubstituted $C_{1-6}$ alkyl or unsubstituted $C_{1-6}$ alkoxy.

Illustratively $R^1$, $R^2$ and $R^3$ represent independently hydrogen.

In a first embodiment, $R^4$ represents $-N=S(O)R^a R^b$. In a second embodiment, $R^4$ represents optionally substituted $C_{1-6}$alkyl. In a first aspect of that embodiment, $R^4$ represents optionally substituted methyl. In a second aspect of that embodiment, $R^4$ represents optionally substituted ethyl. In a third aspect of that embodiment, $R^4$ represents optionally substituted propyl. In a fourth aspect of this embodiment, $R^4$ represents optionally substituted butyl. In a third embodiment, $R^4$ represents optionally substituted $C_{1-6}$ alkoxy. In a first aspect of that embodiment, $R^4$ represents optionally substituted methoxy. In a second aspect of that embodiment, $R^4$ represents optionally substituted ethoxy. In a third aspect of that embodiment, $R^4$ represents optionally substituted propoxy. In a fourth embodiment, $R^4$ represents $C_{3-8}$cycloalkyl. In a first aspect of this embodiment, $R^4$ represents optionally substituted cyclobutyl. In a second aspect of this embodiment, $R^4$ represents optionally substituted cyclopentyl. In a third aspect of this embodiment, $R^4$ represents optionally substituted cyclohexyl. In a fourth aspect, $R^4$ represents optionally substituted cyclopropyl. In a fifth embodiment, $R^4$ represents optionally substituted $C_{3-7}$heterocycloalkyl. In a first aspect of this embodiment, $R^4$ represents optionally substituted azetidinyl. In a second aspect of this embodiment, $R^4$ represents optionally substituted pyrrolidinyl. In a third aspect of this embodiment, $R^4$ represents optionally substituted piperidinyl.

Typically, $R^4$ represents $-N=S(O)R^a R^b$; or $R^4$ represents methyl, ethyl, propyl, butyl, cyclobutyl, cyclopentyl, cyclohexyl, azetidinyl, pyrrolidinyl, piperidinyl, methoxy, ethoxy or propoxy; any of which groups may be optionally substituted by one or more substitutents.

Illustratively, $R^4$ represents ethyl, which may be optionally substituted by one or more substitutents.

Typical examples of optional substituents on $R^4$ include one, two or three substituents independently selected from halogen, hydroxy, amino, (halo)$C_{1-6}$ alkyl and $C_{1-6}$ alkoxy.

Examples of particular substituents on $R^4$ include hydroxy, amino, chloro, fluoro, methyl, fluoromethyl and methoxy.

Illustrative substituents on $R^4$ include hydroxy, fluoro, methyl and fluoromethyl.

In one embodiment, $R^a$ represents optionally substituted $C_{1-6}$ alkyl. In a particular aspect of this embodiment, $R^a$ represents optionally substituted methyl.

Illustratively, $R^a$ represents methyl.

In one embodiment, $R^b$ represents optionally substituted $C_{1-6}$ alkyl. In a particular aspect of this embodiment, $R^b$ represents optionally substituted methyl.

Illustratively, $R^b$ represents methyl.

In another embodiment, $R^a$ and $R^b$ are linked together to form with the S atom to which they are attached an optionally substituted $C_{3-7}$ heterocycloalkyl. In a particular aspect of this embodiment, $R^a$ and $R^b$ are linked together to form with the S atom to which they are attached a tetrahydrothiophenyl. In another particular aspect of this embodiment, $R^a$ and $R^b$ are linked together to form with the S atom to which they are attached an oxathianyl.

Typical substituents on $R^a$ or $R^b$ include halogen, cyano and $C_{1-6}$ alkyl.

Particular values of $R^4$ include (hydroxy)ethyl, (fluoro)(hydroxy)ethyl, (difluoro)(hydroxy)ethyl, (methyl)(hydroxy)(difluoro)ethyl, (methyl)(hydroxy)(fluoro)ethyl, (hydroxy)(fluoromethyl)(fluoro)ethyl, (methyl)(hydroxy)ethyl, (hydroxy)(methyl)propyl, (hydroxy)(methyl)butyl, (hydroxy)cyclobutyl, (hydroxy)azetidinyl, (hydroxy)piperidinyl, methoxy, ethoxy, propoxy, difluoromethoxy, [(dimethyl)oxido-$\lambda^6$-sulfanilidene]amino-, and [oxido-$\lambda^4$-oxathianylidene]amino-, [oxidotetrahydro-1H-1$\lambda^4$-thiophenylidene]amino.

Selected values of $R^4$ include (hydroxy)ethyl, (fluoro)(hydroxy)ethyl, (difluoro)(hydroxy)ethyl, (methyl)(hydroxy)(difluoro)ethyl, (methyl)(hydroxy)(fluoro)ethyl, (hydroxy)(fluoromethyl)(fluoro)ethyl and (methyl)(hydroxy)ethyl.

Particular values of $R^4$ include 1-hydroxy-2,2-difluoroethyl, 1-methyl-1-hydroxy-2,2-difluoroethyl, 1-methyl-1-hydroxy-2-fluoroethyl and 1-hydroxy-1-fluoromethyl-2-fluoroethyl.

Illustrative values of $R^4$ include 1-hydroxy-2,2-difluoroethyl, 1-methyl-1-hydroxy-2,2-difluoroethyl and 1-methyl-1-hydroxy-2-fluoroethyl.

In a particular embodiment according to the present invention, $R^4$ represents 1-methyl-1-hydroxy-2-fluoroethyl.

In a first embodiment, G represents ($G^1$). In a second embodiment, G represents ($G^2$). In a third embodiment, G represents ($G^3$). In a fourth embodiment, G represents ($G^4$). In a fifth embodiment, G represents ($G^5$). In a sixth embodiment, G represents ($G^6$). Suitably, (G) represents a fused heterocycle represented by formula ($G^1$), ($G^5$) or ($G^6$).

In a particular embodiment, G represents ($G^1$) or ($G^5$).

In one embodiment $V^1$ represents N. In another embodiment $V^1$ represents CH.

In one embodiment X represents O. In one embodiment X represents $NR^{11}$.

In a first embodiment, $R^5$ represents halogen. In a first aspect of this embodiment, $R^5$ represents chloro. In a second aspect of this embodiment, $R^5$ represents bromo. In a third aspect of this embodiment, $R^5$ represents fluoro.

In a second embodiment, $R^5$ represents cyano.

In a third embodiment, $R^5$ represents optionally substituted $C_{1-6}$ alkyl. In a first aspect of this embodiment, $R^5$ represents optionally substituted methyl. In a second aspect of this embodiment, $R^5$ represents optionally substituted ethyl.

In a fourth embodiment, $R^5$ represents optionally substituted $C_{1-6}$ alkoxy. In a first aspect of this embodiment, $R^5$ represents optionally substituted methoxy. In a second aspect of this embodiment, $R^5$ represents optionally substituted ethoxy.

In a first embodiment, $R^6$ represents hydrogen. In a second embodiment, $R^6$ represents halogen. In a first aspect of this embodiment, $R^6$ represents chloro. In a second aspect of this embodiment, $R^6$ represents bromo. In a third aspect of this embodiment, $R^6$ represents fluoro.

In a third embodiment, $R^6$ represents cyano.

In a fourth embodiment, $R^6$ represents optionally substituted $C_{1-6}$ alkyl. In a first aspect of this embodiment, $R^6$ represents optionally substituted methyl. In a second aspect of this embodiment, $R^6$ represents optionally substituted ethyl.

In a fifth embodiment, $R^6$ represents optionally substituted $C_{1-6}$ alkoxy. In a first aspect of this embodiment, $R^6$ represents optionally substituted methoxy. In a second aspect of this embodiment, $R^6$ represents optionally substituted ethoxy.

In a first embodiment, $R^7$ represents hydrogen. In a second embodiment, $R^7$ represents halogen. In a first aspect of this embodiment, $R^7$ represents chloro. In a second aspect of this embodiment, $R^7$ represents bromo. In a third aspect of this embodiment, $R^7$ represents fluoro.

In a third embodiment, $R^7$ represents cyano.

In a fourth embodiment, $R^7$ represents optionally substituted $C_{1-6}$ alkyl. In a first aspect of this embodiment, $R^7$ represents optionally substituted methyl. In a second aspect of this embodiment, $R^7$ represents optionally substituted ethyl.

In a fifth embodiment, $R^7$ represents optionally substituted $C_{1-6}$ alkoxy. In a first aspect of this embodiment, $R^7$ represents optionally substituted methoxy. In a second aspect of this embodiment, $R^7$ represents optionally substituted ethoxy.

In a first embodiment, $R^8$ represents hydrogen. In a second embodiment, $R^8$ represents halogen. In a first aspect of this embodiment, $R^8$ represents chloro. In a second aspect of this embodiment, $R^8$ represents bromo. In a third aspect of this embodiment, $R^8$ represents fluoro.

In a third embodiment, $R^8$ represents optionally substituted $C_{1-6}$ alkyl. In a first aspect of this embodiment, $R^8$ represents optionally substituted methyl. In a second aspect of this embodiment, $R^8$ represents optionally substituted ethyl.

In a fourth embodiment, $R^8$ represents optionally substituted $C_{1-6}$ alkoxy. In a first aspect of this embodiment, $R^8$ represents optionally substituted methoxy. In a second aspect of this embodiment, $R^8$ represents optionally substituted ethoxy.

In a fifth embodiment, $R^8$ represents optionally substituted $C_{3-8}$ cycloalkyl. In a first aspect of this embodiment, $R^8$ represents optionally substituted cyclopropyl.

In a sixth embodiment, $R^8$ represents cyano.

In a first embodiment, $R^9$ represents hydrogen. In a second embodiment, $R^9$ represents halogen. In one aspect of this embodiment, $R^9$ represents fluoro.

In a third embodiment, $R^9$ represents optionally substituted $C_{1-6}$ alkyl. In a first aspect of this embodiment, $R^9$ represents optionally substituted methyl. In a second aspect of this embodiment, $R^9$ represents optionally substituted ethyl.

In a first embodiment, $R^{10}$ represents hydrogen. In a second embodiment, $R^{10}$ represents halogen. In one aspect of this embodiment, $R^{10}$ represents fluoro.

In a third embodiment, $R^{10}$ represents optionally substituted $C_{1-6}$ alkyl. In a first aspect of this embodiment, $R^{10}$ represents optionally substituted methyl. In a second aspect of this embodiment, $R^{10}$ represents optionally substituted ethyl.

In a first embodiment, $R^{11}$ represents hydrogen. In a second embodiment, $R^{11}$ represents optionally substituted $C_{1-6}$ alkyl. In one aspect of this embodiment, $R^{11}$ represents optionally substituted methyl.

Optional substituents on $R^5$, $R^6$, $R^7$, $R^8$, $R^9$, $R^{10}$ and $R^{11}$ include one, two or three substituents selected from halogen, cyano, amino, hydroxy, $C_{1-6}$ alkyl and $C_{1-6}$ alkoxy.

Particular values of optional substitutents on $R^5$, $R^6$, $R^7$, $R^8$, $R^9$, $R^{10}$ and $R^{11}$ include chloro, fluoro, cyano, amino, hydroxy, methyl and methoxy.

Typically, $R^5$ represents halogen or cyano; or $R^5$ represents unsubstituted $C_{1-6}$ alkyl or unsubstituted $C_{1-6}$ alkoxy.

Suitable examples of $R^5$ groups according to the present invention include chloro, bromo, fluoro, cyano, methyl and methoxy.

In a particular embodiment, $R^5$ represents halogen.

Illustratively, $R^5$ represents chloro.

Typically, $R^6$ and $R^7$ represent independently hydrogen, halogen or cyano; or $R^6$ and $R^7$ represent independently unsubstituted $C_{1-6}$ alkyl or unsubstituted $C_{1-6}$ alkoxy.

Suitable examples of $R^6$ and $R^7$ groups include hydrogen, chloro, bromo, fluoro, cyano, methyl and methoxy.

In a particular embodiment, $R^6$ represents halogen.

Illustratively, $R^6$ represents chloro.

In a particular embodiment, $R^7$ represents hydrogen.

Typically, $R^8$ represents hydrogen, halogen or cyano; or $R^8$ represents unsubstituted $C_{1-6}$ alkyl, unsubstituted $C_{3-8}$ cycloalkyl or unsubstituted $C_{1-6}$ alkoxy.

Suitably, $R^8$ represents hydrogen, cyano or unsubstituted $C_{3-8}$ cycloalkyl.

Suitable examples of $R^8$ groups include hydrogen, cyano, chloro, bromo, fluoro, methylmethoxy and cyclopropyl Illustratively, $R^8$ represents hydrogen, cyano or cyclopropyl.

Particularly, $R^8$ represents hydrogen.

Typically, $R^9$ and $R^{10}$ represent independently hydrogen or halogen; or $R^9$ and $R^{10}$ represent independently unsubstituted $C_{1-6}$ alkyl. Suitable examples of $R^9$ and $R^{10}$ groups include hydrogen and fluoro.

Typically, $R^{11}$ represents hydrogen or unsusbtituted $C_{1-6}$ alkyl.

Suitable examples of $R^{11}$ include hydrogen and methyl.

In a particular embodiment, $W^1$ represents $CF_2$.

In a particular embodiment, $W^2$ represents $CH_2$.

Suitably, (G) represents a fused heterocycle represented by formula ($G^1$), ($G^5$) or ($G^6$) wherein X represents O or $NR^{11}$;

$V^1$ represents CH or N;

$R^{11}$ represents hydrogen or unsubstituted $C_{1-6}$ alkyl;

$R^5$ and $R^6$ represent independently halogen;

$R^7$ represents hydrogen; and $R^8$ represents hydrogen, cyano or unsubstituted $C_{3-8}$ cycloalkyl.

Illustratively, (G) represents a fused heterocycle represented by formula ($G^{1a}$), ($G^{1b}$), ($G^{1c}$), ($G^{1d}$), ($G^{1e}$), ($G^{5b}$) or ($G^{6a}$).

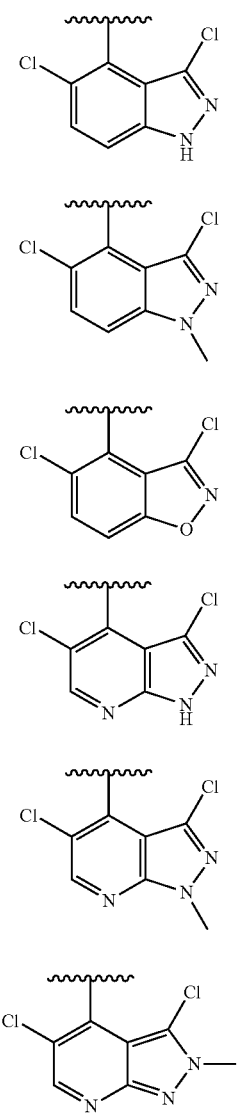

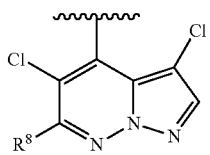

wherein the asterisk (*) represents the point of attachment of G to the remainder of the molecule and $R^8$ represents hydrogen, cyano or cyclopropyl.

In a particular embodiment, (G) represents a fused heterocycle represented by formula ($G^{6a}$) wherein $R^8$ represents hydrogen.

Another particular sub-class of compounds in accordance with the present invention is the sub-class of compounds represented by formula (IB), or a pharmaceutically acceptable salt thereof,

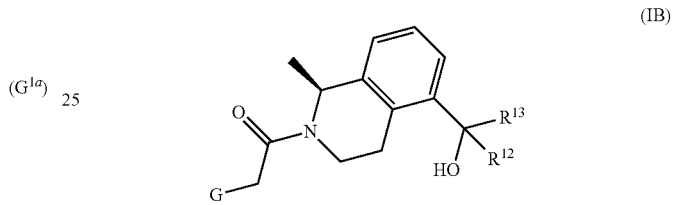

wherein $R^{12}$ and $R^{13}$ represent independently hydrogen or optionally substituted $C_{1-6}$ alkyl; and G is as defined here above.

In one embodiment, $R^{12}$ represents hydrogen. In a particular aspect of this embodiment, $R^{12}$ represents deuterium. In another embodiment, $R^{12}$ represents optionally substituted $C_{1-6}$ alkyl. In one aspect of that embodiment, $R^{12}$ represents optionally substituted methyl.

In one embodiment, $R^{13}$ represents hydrogen. In a particular aspect of this embodiment, $R^{13}$ represents deuterium. In another embodiment, $R^{13}$ represents optionally substituted $C_{1-6}$ alkyl. In one aspect of that embodiment, $R^{13}$ represents optionally substituted methyl.

Optional substitutents on $R^{12}$ and $R^{13}$ include one, two or three substituents selected from halogen, hydroxy, amino and $C_{1-6}$ alkoxy.

Selected values of substitutents on $R^{12}$ and $R^{13}$ include hydroxy, amino, chloro, fluoro, methyl, and methoxy.

Illustratively, $R^{12}$ and $R^{13}$ represent independently hydrogen, deuterium, methyl, fluoromethyl or difluoromethyl.

In a particular embodiment according to the present invention $R^{12}$ represents hydrogen and $R^{13}$ represents difluoromethyl.

In another particular embodiment according to the present invention, $R^{12}$ represents methyl and $R^{13}$ represents fluoromethyl.

In a further particular embodiment according to the present invention, $R^{12}$ represents methyl and $R^{13}$ represents difluoromethyl.

In yet a further particular embodiment according to the present invention, $R^{12}$ represents fluoromethyl and $R^{13}$ represents fluoromethyl.

A further particular sub-class of compounds in accordance with the present invention is the sub-class of compounds represented by formula (IC), or a pharmaceutically acceptable salt thereof,

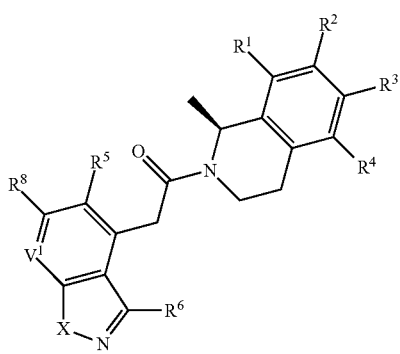

(IC)

wherein X, V$^1$, R$^1$, R$^2$, R$^3$, R$^4$, R$^5$, R$^6$ and R$^8$ are as defined above.

A particular sub-group of compounds of formula (IC) is represented by formula (IC-a),

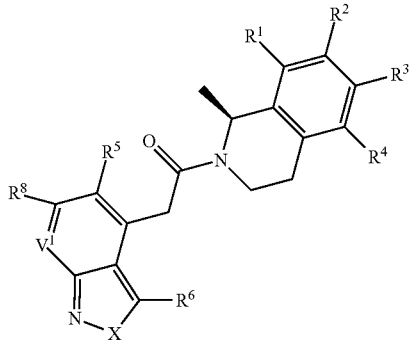

(ID)

wherein X, V$^1$, R$^1$, R$^2$, R$^3$, R$^4$, R$^5$, R$^6$ and R$^8$ are as defined above.

A particular sub-group of compounds of formula (ID) is represented by formula (ID-a),

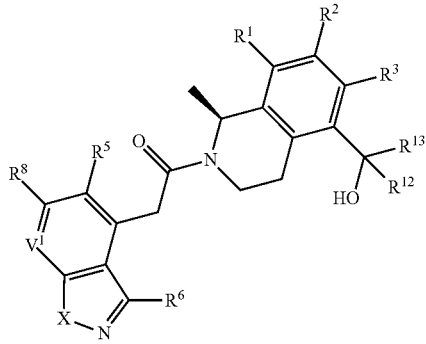

(IC-a)

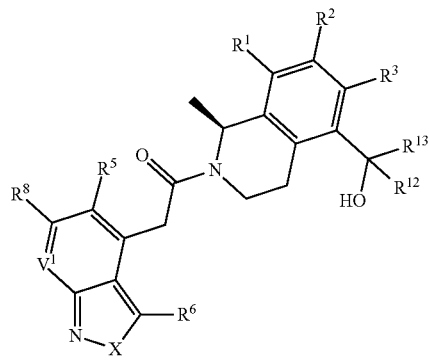

(ID-a)

wherein X, V$^1$, R$^1$, R$^2$, R$^3$, R$^4$, R$^5$, R$^6$, R$^8$, R$^{12}$ and R$^{13}$ are as defined above.

In a particular aspect, the present invention relates to compounds represented by formula (IC-a), wherein X represents O or NR$^{11}$;

V$^1$ represents CH or N;

R$^1$, R$^2$, R$^3$ and R$^8$ represent independently hydrogen;

R$^5$ and R$^6$ represent independently chloro;

R$^{11}$ represents hydrogen or methyl; and

R$^{12}$ and R$^{13}$ represent independently hydrogen, deuterium, methyl, fluoromethyl or difluoromethyl.

In a particular embodiment of this aspect, X represents NR$^{11}$.

Another further particular sub-class of compounds in accordance with the present invention is the sub-class of compounds represented by formula (ID), or a pharmaceutically acceptable salt thereof, wherein X, V$^1$, R$^1$, R$^2$, R$^3$, R$^4$, R$^5$, R$^6$, R$^8$, R$^{12}$ and R$^{13}$ are as defined above.

In a particular aspect, the present invention relates to compounds represented by formula (ID-a), wherein X represents O or NR$^{11}$;

V$^1$ represents CH or N;

R$^1$, R$^2$, R$^3$ and R$^8$ represent independently hydrogen;

R$^5$ and R$^6$ represent independently chloro;

R$^{11}$ represents hydrogen or methyl; and

R$^{12}$ and R$^{13}$ represent independently hydrogen, deuterium, methyl, fluoromethyl or difluoromethyl.

In a particular embodiment of this aspect, X represents NR$^{11}$. In an aspect of this particular embodiment R$^{11}$ represents methyl.

Yet, another further particular subclass of compounds in accordance with the present invention is the sub-class of compounds represented by formula (IE), or a pharmaceutically acceptable salt thereof,

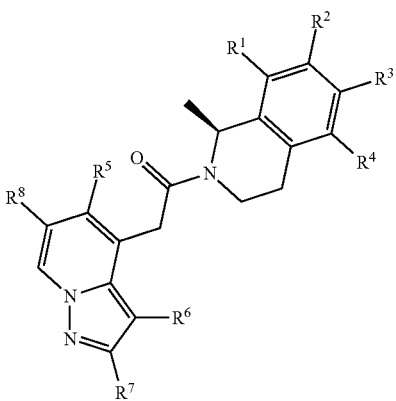

(IE)

wherein R¹, R², R³, R⁴, R⁵, R⁶, R⁷ and R⁸ are as defined above.

A particular sub-group of compounds of formula (IE) is represented by formula (IE-a),

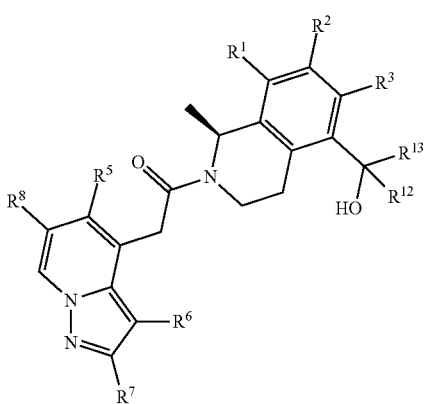

(IE-a)

wherein R¹, R², R³, R⁵, R⁶, R⁷, R⁸, R¹² and R¹³ are as defined above.

In a particular aspect, the present invention relates to compounds represented by formula (IE-a),
Wherein
R¹, R², R³ and R⁷ represent independently hydrogen;
R⁵ and R⁶ represent independently chloro;
R⁸ represents hydrogen, cyano or cyclopropyl; and
R¹² and R¹³ represent independently hydrogen, deuterium, methyl, fluoromethyl or difluoromethyl.

In a particular embodiment according to this aspect of the invention, R⁸ represents hydrogen.

It will be apparent for the person skilled in the art that compounds represented by formula (IB), (IC-a), (ID-a) and (IE-a) wherein R¹² and R¹³ are different may exist in the form of two different stereoisomers wherein the carbon bearing the hydroxy, R¹² and R¹³ groups has an absolute stereochemical configuration of (R) or (S).

Therefore, in the following section, and as will be further apparent from the experimental section, where the name of the compound does not specify a particular stereochemical configuration for said carbon, it is nevertheless intended to encompass both the individual (R) and (S) stereoisomers.

Specific novel compounds in accordance with the present invention include each of the compounds whose preparation is described in the accompanying Examples, and pharmaceutically acceptable salts and solvates thereof, and co-crystals thereof.

Therefore, in a particular aspect, the present invention relates to compounds of formula (I) which are selected from the group consisting of 2-(3,5-dichloro-1,2-benzoxazol-4-yl)-1-[(1S)-5-[(1S)-2,2-difluoro-1-hydroxy-ethyl]-1-methyl-3,4-dihydro-1H-isoquinolin-2-yl]ethanone;

2-(3,5-dichloro-1H-indazol-4-yl)-1-[(1S)-5-[(1R)-2-fluoro-1-hydroxy-1-methyl-ethyl]-1-methyl-3,4-dihydro-1H-isoquinolin-2-yl]ethanone;

2-(3,5-dichloro-1H-indazol-4-yl)-1-[(1S)-5-[(1S)-2-fluoro-1-hydroxy-1-methyl-ethyl]-1-methyl-3,4-dihydro-1H-isoquinolin-2-yl]ethanone;

2-(3,5-dichloro-1H-indazol-4-yl)-1-[(1S)-5-[(1R)-2,2-difluoro-1-hydroxy-ethyl]-1-methyl-3,4-dihydro-1H-isoquinolin-2-yl]ethanone;

2-(3,5-dichloro-1H-indazol-4-yl)-1-[(1S)-5-[(1S)-2,2-difluoro-1-hydroxy-ethyl]-1-methyl-3,4-dihydro-1H-isoquinolin-2-yl]ethanone;

2-(3,5-dichloro-1H-indazol-4-yl)-1-[(1S)-5-[2,2-difluoro-1-hydroxy-1-methyl-ethyl]-1-methyl-3,4-dihydro-1H-isoquinolin-2-yl]ethanone;

2-(3,5-dichloro-2-methyl-indazol-4-yl)-1-[(1S)-5-[(1R)-2,2-difluoro-1-hydroxy-ethyl]-1-methyl-3,4-dihydro-1H-isoquinolin-2-yl]ethanone;

2-(3,5-dichloro-2-methyl-indazol-4-yl)-1-[(1S)-5-[(1S)-2,2-difluoro-1-hydroxy-ethyl]-1-methyl-3,4-dihydro-1H-isoquinolin-2-yl]ethanone;

2-(3,5-dichloro-1-methyl-1H-indazol-4-yl)-1-[(1S)-5-[(1R)-2,2-difluoro-1-hydroxyethyl]-1-methyl-3,4-dihydroisoquinolin-2(1H)-yl]ethanone;

2-(3,5-dichloro-1-methyl-1H-indazol-4-yl)-1-[(1S)-5-[(1S)-2,2-difluoro-1-hydroxyethyl]-1-methyl-3,4-dihydroisoquinolin-2(1H)-yl]ethanone;

2-(3,5-dichloro-2-methyl-indazol-4-yl)-1-[(1S)-5-[2,2-difluoro-1-hydroxy-1-methyl-ethyl]-1-methyl-3,4-dihydro-1H-isoquinolin-2-yl]ethanone;

2-(3,5-dichloro-1H-pyrazolo[3,4-b]pyridin-4-yl)-1-[(1S)-5-[(1S)-2-fluoro-1-hydroxy-1-methyl-ethyl]-1-methyl-3,4-dihydro-1H-isoquinolin-2-yl]ethanone;

2-(3,5-dichloro-1H-pyrazolo[3,4-b]pyridin-4-yl)-1-[(1S)-5-[(1R)-2-fluoro-1-hydroxy-1-methyl-ethyl]-1-methyl-3,4-dihydro-1H-isoquinolin-2-yl]ethanone;

2-(3,5-dichloro-1H-pyrazolo[3,4-b]pyridin-4-yl)-1-[(1S)-5-[2,2-difluoro-1-hydroxy-1-methyl-ethyl]-1-methyl-3,4-dihydro-1H-isoquinolin-2-yl]ethanone;

2-(3,5-dichloro-1H-pyrazolo[3,4-b]pyridin-4-yl)-1-[(1S)-5-[2-fluoro-1-(fluoromethyl)-1-hydroxy-ethyl]-1-methyl-3,4-dihydro-1H-isoquinolin-2-yl]ethanone;

2-(3,5-dichloro-1-methyl-pyrazolo[3,4-b]pyridin-4-yl)-1-[(1S)-5-((1R)-2-fluoro-1-hydroxy-1-methyl-ethyl)-1-methyl-3,4-dihydro-1H-isoquinolin-2-yl]ethanone;

2-(3,5-dichloro-1-methyl-pyrazolo[3,4-b]pyridin-4-yl)-1-[(1S)-5-((1S)-2-fluoro-1-hydroxy-1-methyl-ethyl)-1-methyl-3,4-dihydro-1H-isoquinolin-2-yl]ethanone;

2-(3,5-dichloro-1-methyl-pyrazolo[3,4-b]pyridin-4-yl)-1-[(1S)-5-[2,2-difluoro-1-hydroxy-1-methyl-ethyl]-1-methyl-3,4-dihydro-1H-isoquinolin-2-yl]ethanone;

2-(3,5-dichloro-1-methyl-pyrazolo[3,4-b]pyridin-4-yl)-1-[(1S)-5-[2-fluoro-1-(fluoromethyl)-1-hydroxy-ethyl]-1-methyl-3,4-dihydro-1H-isoquinolin-2-yl]ethanone;

2-(3,5-dichloro-1-methyl-indazol-4-yl)-1-[(1S)-5-[(1R)-2-fluoro-1-hydroxy-1-methyl-ethyl]-1-methyl-3,4-dihydro-1H-isoquinolin-2-yl]ethanone;

2-(3,5-dichloro-1-methyl-indazol-4-yl)-1-[(1S)-5-[(1S)-2-fluoro-1-hydroxy-1-methyl-ethyl]-1-methyl-3,4-dihydro-1H-isoquinolin-2-yl]ethanone;
2-(3,5-dichloro-1-methyl-indazol-4-yl)-1-[(1S)-5-[2,2-difluoro-1-hydroxy-1-methyl-ethyl]-1-methyl-3,4-dihydro-1H-isoquinolin-2-yl]ethanone
2-(3,5-dichloro-1-methyl-indazol-4-yl)-1-[(1S)-5-[2-fluoro-1-(fluoromethyl)-1-hydroxy-ethyl]-1-methyl-3,4-dihydro-1H-isoquinolin-2-yl]ethanone;
2-(3,5-dichloropyrazolo[1,5-a]pyridin-4-yl)-1-[(1S)-5-[(1S)-2-fluoro-1-hydroxy-1-methyl-ethyl]-1-methyl-3,4-dihydro-1H-isoquinolin-2-yl]ethanone;
2-(3,5-dichloropyrazolo[1,5-a]pyridin-4-yl)-1-[(1S)-5-[(1S)-2,2-difluoro-1-hydroxy-ethyl]-1-methyl-3,4-dihydro-1H-isoquinolin-2-yl]ethanone;
2-(3,5-dichloro-6-cyclopropyl-pyrazolo[1,5-a]pyridin-4-yl)-1-[(1S)-5-(2,2-difluoro-1-hydroxy-1-methyl-ethyl)-1-methyl-3,4-dihydro-1H-isoquinolin-2-yl]ethanone; and
3,5-dichloro-4-[2-[(1S)-5-(2,2-difluoro-1-hydroxy-1-methyl-ethyl)-1-methyl-3,4-dihydro-1H-isoquinolin-2-yl]-2-oxo-ethyl]pyrazolo[1,5-a]pyridine-6-carbonitrile.

The compounds in accordance with the present invention are beneficial in the treatment and/or prevention of various human ailments. These include cognitive and negative symptoms in schizophrenia, cognitive impairment related to classical antipsychotic therapy, impulsivity, attention disorder with hyperactivity (ADHD), Parkinson's disease and related movement disorders, dystonia, Huntington's disease, dementia with Lewy Body, Alzheimer's disease, age-related cognitive decline, mild cognitive impairment (MCI), drug addiction, sleep disorders and apathy.

In particular, the compounds according to the present invention are beneficial for the treatment and/or prevention of Parkinson's disease and related movement disorders.

Activity in any of the above-mentioned therapeutic indications or disorders can of course be determined by carrying out suitable clinical trials in a manner known to a person skilled in the relevant art for the particular indication and/or in the design of clinical trials in general.

For treating diseases, compounds of formula (I) or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula (I) or a pharmaceutically acceptable salt thereof in combination with a pharmaceutically acceptable diluent or carrier.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula (I) in compositions for oral administration is at least 0.5% by weight and can be up to 80% by weight with respect to the total weight of the composition.

In accordance with the invention it has also been found that the compounds of formula (I) or the pharmaceutically acceptable salts thereof can be administered alone or in combination with other pharmaceutically active ingredients.

In compositions for parenteral administration, the quantity of compound of formula (I) present is at least 0.5% by weight and can be up to 33% by weight with respect to the total weight of the composition. For the preferred parenteral compositions, the dosage unit is in the range 0.5 mg to 3000 mg of compounds of formula (I).

The daily dose can fall within a wide range of dosage units of compound of formula (I) and is generally in the range 0.5 to 3000 mg. However, it should be understood that the specific doses can be adapted to particular cases depending on the individual requirements, at the physician's discretion.

It will be apparent to the person skilled in the art that there are various synthetic pathways that can lead to the compounds according to the invention. The following processes are aimed at illustrating some of these synthetic pathways but should not be construed in any way as a limitation on how the compounds according to the invention should be made.

Compounds of formula (I) may be prepared by a process involving reacting an intermediate of formula (II) with an intermediate of formula (III),

(II)

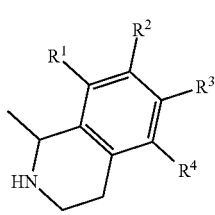

(III)

wherein G, $R^1$, $R^2$, $R^3$ and $R^4$ are as defined here above.

The reaction is conveniently effected in the presence of 1-(3-dimethylaminopropyl)-3-ethylcarbodiimide hydrochloride and 1-hydroxybenzotriazole hydrate, in a suitable solvent e.g. dimethylformamide, with a catalytic amount of 4-methylmorpholine.

Alternatively, the reaction may be effected in the presence of classical coupling agents such as benzotriazolyl derivatives (BOP and the like) or uronium derivatives (HBTU, COMU® and the like) or other reagents known by the person skilled in the art, in the presence of a base such as triethylamine or diisopropylethylamine in a solvent such as N,N-dimethylformamide or dichloromethane.

Compounds of formula (I), wherein (G) represents ($G^1$), X represents $NR^{11}$ and $R^6$ represents chloro, may be prepared by chlorination of compounds of formula (I) wherein $R^6$ represents hydrogen. This reaction may be performed by a chlorinating agent such as N-chlorosuccinimide or trichloroisocyanuric acid in zeolite Y, in a polar solvent such as acetonitrile or THF, at a temperature ranging from room temperature to 70° C.

Compounds of formula (I), wherein (G) represents ($G^1$), X represents $NR^{11}$ and $R^{11}$ represents hydrogen, may be prepared by deprotection of a compound of formula (I) wherein $R^{11}$ represents a protecting group such as a tetrahydropyranyl group. This reaction may be performed according to any method known to the person skilled in the art.

Intermediates of formula (III), may be prepared by a process involving reaction of an intermediate of formula (IIIa),

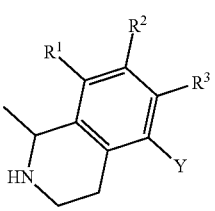

(IIIa)

wherein $R^1$, $R^2$, and $R^3$ are as defined here above; and

Y represents halogen, e.g. bromo.

Some intermediates of formula (III) may be prepared by a process involving coupling of an intermediate of formula (IIIa) with a compound of formula $R^4$—$Y^1$, wherein $Y^1$ represents hydrogen, halogen, or boronic acid derivative, in the presence of a transition metal complex, generally a palladium complex, and a base, according to methods known to the person skilled in the art. The reaction is conveniently effected at elevated temperature in a suitable solvent.

Some of these conditions for particular groups are described hereafter:

(i) When $R^4$ represents —N=S(O)$R^aR^b$, intermediate (IIIa) is reacted with HN=S(O)$R^aR^b$ in the presence of a transition metal complex, formed for example with Pd(II) acetate and 2,2'-bis(diphenylphosphino)1,1'-binaphthyl, in a suitable solvent, e.g. 1,4-dioxane. The reaction is conveniently effected in the presence of a suitable base, e.g. an inorganic base such as cesium carbonate, at elevated temperature.

(ii) When $R^4$ represents $C_{1-6}$alkyl, the reaction is effected in the presence of intermediate (IIIa) is first reacted with a (commercial) vinyl boronic acid/boronate ester in the presence of a transition metal catalyst, e.g. tetrakis(triphenylphosphine)palladium (0), followed by a reduction under pressure of hydrogen, in the presence of a transition metal catalyst, e.g. Pd/C, in a suitable solvent, e.g. ethanol.

(iii) When $R^4$ represents $C_{3-7}$cycloalkyl, intermediate (IIIa) is first reacted with a boronate ester, e.g. pinacol boronate ester, in the presence of a transition metal catalyst, e.g. tetrakis(triphenylphosphine)palladium(0), to afford the corresponding boronate. The latter is subsequently reacted with $R^4$—$Y^1$, wherein $Y^1$ represents halogen, e.g. chloro or bromo, in the presence of a transition metal catalyst, e.g. tetrakis(triphenylphosphine)palladium(0) and an inorganic base, e.g. sodium carbonate.

Intermediates of formula (III) wherein $R^4$ represents $C_{3-7}$heterocycloalkyl linked to the rest of the molecule by a nitrogen atom, may be prepared by a process involving a cross coupling reaction of an intermediate of formula (IIIa) with a compound of formula ($C_{3-7}$heterocycloalkyl)NH, in the presence of a transition metal complex catalyst, e.g. tris(dibenzylideneacetone)dipalladium(0), and a base, e.g. sodium tert-butoxide, in a suitable solvent, e.g. toluene. The reaction is conveniently effected under microwave conditions, at elevated temperature.

Intermediates of formula (III), wherein $R^4$ represents a $C_{1-6}$ alkyl substituted by a hydroxy group, i.e. wherein $R^4$ represents —C(OH)$R^{12}R^{13}$, may be prepared by a process involving reaction of an intermediate of formula (IIIa) as defined above, with an intermediate of formula (IV), wherein $R^{12}$ and $R^{13}$ are as defined for compounds of formula (IA).

(IV)

The reaction is conveniently effected by metal-halogen exchange in the presence of n-BuLi, in a suitable solvent, e.g. tetrahydrofuran, at low temperature, according to methods known to the person skilled in the art.

Alternatively, intermediates of formula (III), wherein $R^4$ represents a $C_{1-6}$ alkyl substituted by a hydroxy group, i.e. wherein $R^4$ represents —C(OH)$R^{12}R^{13}$, may be prepared by a process involving reaction of an intermediate (IIIb),

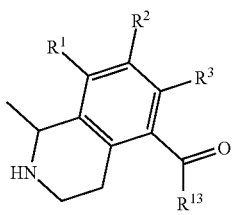

(IIIb)

wherein $R^1$, $R^2$, $R^3$ and $R^{13}$ are as defined here above.

When $R^{12}$ represents hydrogen, the reaction is conveniently effected in the presence of a suitable reducing agent, e.g. lithium borohydride, in a suitable solvent, e.g. dichloromethane, at low temperature.

When $R^{12}$ represents methyl, the reaction may be performed using methylmagnesium halide, e.g. methylmagnesium chloride, in a suitable solvent, e.g. THF, according to methods known to the person skilled in the art.

Intermediates of formula (III), wherein $R^4$ represents a $C_{1-6}$ alkyl substituted by a hydroxy group, i.e. wherein $R^4$ represents —C(OH)$R^{12}R^{13}$, and $R^{12}$ represents deuterium, may be prepared by a process involving reaction of an intermediate of formula (IIIb), as defined here above, with a suitable reducing agent, e.g. sodium borodeuteride, in a suitable solvent, e.g. ethanol, at low temperature, according to methods known to the person skilled in the art.

Compounds of formula (I) wherein $R^4$ represents —C(OH)$R^{12}R^{13}$, and $R^{12}$ represents methyl, may alternatively be prepared by a process involving coupling of an intermediate of formula (II) with an intermediate of formula (IIIb) under conditions analogous to those described here above for the coupling of intermediates of formula (II), with intermediate of formula (III), followed by reaction with methylmagnesium halide, e.g. methylmagnesium chloride, in a suitable solvent, e.g. THF, according to methods known to the person skilled in the art.

Intermediates of formula (IIIb) may be prepared by a process involving reaction of an intermediate represented by formula (IIIa) with an intermediate of formula (IVa),

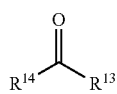

(IVa)

wherein
$R^{14}$ represents $C_{1-6}$alkoxy, e.g. methoxy or ethoxy, or di-($C_{1-6}$alkyl)amino, e.g. dimethylamino; and
$R^{13}$ is as defined here above.

The reaction is conveniently effected by metal-halogen exchange in the presence of n-BuLi, in a suitable solvent, e.g. tetrahydrofuran, at low temperature, according to methods known to the person skilled in the art.

In the above reactions, the amino group of intermediate of formula (IIIa) will generally first be protected with an appropriate protective group, e.g. tert-butoxycarbonyl group, according to methods known to the person skilled in the art, before substitution of Y of intermediate of formula (IIIa) or reduction of the carbonyl moeity of intermediate of formula (IIIb).

Intermediates of formula (IIIa) may be prepared by a process involving reaction of an intermediate of formula (V),

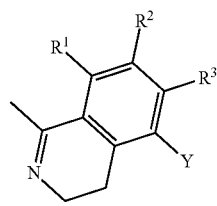

(V)

wherein wherein $R^1$, $R^2$, $R^3$ and Y are as defined here above.

The reaction is conveniently effected in the presence of a suitable reducing agent, e.g. sodium borohydride, in a suitable solvent, e.g. ethanol, at low temperature, according to methods known to the person skilled in the art.

Intermediates of formula (V) may be prepared by a process involving reaction of an intermediate of formula (VI),

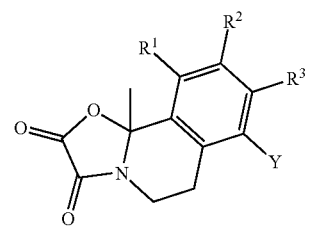

(VI)

wherein wherein $R^1$, $R^2$, $R^3$ and Y are as defined here above.

The reaction is conveniently effected in the presence of oxalyl chloride in a suitable solvent, e.g. dichloromethane, in the presence of a transition metal salt, e.g. iron chloride, at low temperature.

Intermediate of formula (VI) may be prepared by a process involving reaction of commercially available intermediate (VII),

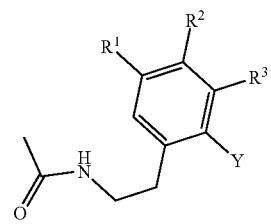

(VII)

wherein $R^1$, $R^2$, $R^3$ and Y are as defined here above.

Intermediate of formula (II) may be prepared by a process involving reaction of an intermediate of formula G-CH$_2$-$R^{15}$ herefater referred to as intermediate of formula (IIa), wherein
$R^{15}$ represents cyano or —COOR$^c$;
$R^c$ represents $C_{1-6}$ alkyl; and
G is as defined hereabove.

When $R^{15}$ represents —COOR$^c$, the reaction is conveniently effected in the presence of a suitable base, e.g. lithium hydroxide, in a suitable solvent, e.g. water, according to methods known to the person skilled in the art.

When $R^{15}$ represents cyano, the reaction is conveniently be effected in the presence of a strong acid, e.g. sulphuric acid, or a strong base, e.g. sodium hydroxide, in a suitable solvent, e.g. polar solvent such as water or ethanol, at elevated temperature.

Intermediate of formula (IIa) may be prepared by a process involving decarboxylation of an intermediate of formula (IIb),

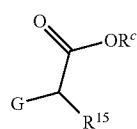

(IIb)

wherein

G, $R^c$ and $R^{15}$ as defined here above.

When $R^{15}$ represesents —COOR$^c$, and $R^c$ is as defined here above, decarboxylation is conveniently effected in the presence of lithium chloride, in a suitable solvent e.g. mixture of water and dimethylsulphoxide, at elevated temperature.

When $R^{15}$ represents cyano, decarboxylation is conveniently effected in the presence of a suitable acid, e.g. trifluoroacetic acid, in a suitable solvent e.g. dichloromethane, at elevated temperature.

Alternatively, intermediates of formula (IIa) and (IIb) may be prepared by a process involving reaction of an intermediate of formula G-Y$^1$, wherein Y$^1$ represents halogen, e.g. fluoro, bromo or iodo, and G is as defined hereabove;

with a compound of formula CHR$^d$R$^{15}$;

wherein

R$^d$ represents respectively hydrogen or M-Y; or —COOR$^c$;

M is a metal, e.g. zinc; and

R$^c$, R$^{15}$ and Y are as defined here above.

When R$^d$ represents hydrogen, the reaction is conveniently effected in the presence of a suitable base, e.g. lithium hydroxide, in a suitable solvent, e.g. water, according to methods known to the person skilled in the art.

When R$^d$ represents —COOR$^c$, the reaction is conveniently effected in the presence of an inorganic base, e.g. cesium carbonate, in a suitable solvent, e.g. dimethylformamide, at elevated temperature.

When R$^d$ represents M-Y, the reaction is conveniently effected in the presence of a transition metal catalyst complex, e.g. tri[(tert-butyl)phosphine]Pd(II), in a suitable solvent, e.g. THF, at elevated temperature.

Alternatively, intermediates of formula (II) may be prepared by a process involving carboxylation of an intermediate of formula G-R$^e$ wherein R$^e$ represents methyl.

The reaction is conveniently effected under pressure of carbon dioxide, in the presence of lithium diisopropylamide and hexamethylphosphoramide, in a suitable solvent, e.g. THF, at low temperature. Yet alternatively, intermediates of formula (II) may be prepared by oxidation of intermediates of formula (IIc)

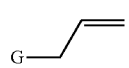

(IIc)

The reaction may be effected with an oxidizing agent, e.g. sodium periodate, in the presence of a transition metal catalyst, e.g. ruthenium (III) chloride, in a suitable solvent, e.g a mixture of acetonitrile, water and carbon tetrachloride.

Preparation of intermediates (IIa), G-Y$^1$, G-R$^e$ and (IIc) will vary depending on the nature of the (G) group.

Intermediates of formula G-Y$^1$ wherein (G) represents (G$^1$) and X represents NR$^{11}$ may be prepared by a process involving reaction of an intermediate of formula (VIII),

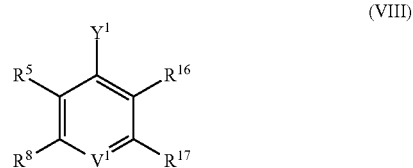

(VIII)

wherein

R$^{16}$ represents C$_{1-6}$ alkyl or formyl;

R$^{17}$ represents amino or halogen;

Y$^1$ represents halogen; and

R$^5$, R$^8$ and V$^1$ are as defined above.

When V$^1$ represents CH, R$^{16}$ represents C$_{1-6}$ alkyl and R$^{17}$ represents amino, the reaction is conveniently effected in the presence of sodium nitrite, in a suitable solvent, e.g. water, in the presence of an acid, e.g. acetic acid.

When V$^1$ represents N, R$^{16}$ represents formyl and R$^{17}$ represents halogen, e.g. chloro, the reaction is conveniently effected in the presence of hydrazine, in a suitable solvent, e.g. water, in the presence of an acid, e.g. p-toluenesulfonic acid. Alternatively, intermediates of formula G-Y$^1$ wherein (G) represents (G$^1$), X represents NR$^{11}$ V$^1$ represents N, R$^6$ represents chloro, and R$^5$ and R$^8$ are as defined above, may be prepared from commercially available 4-chloro azaindazole according to reactions known to the person skilled in the art.

Intermediates of formula (IIa), wherein (G) represents (G$^1$) or (G$^2$) may be prepared by a process involving reaction of an intermediate of formula (IX).

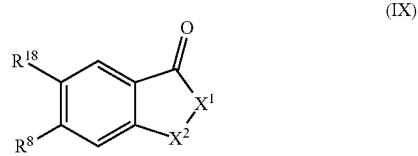

(IX)

wherein

R$^{18}$ represents NO$_2$, amino or halogen;

X$^1$ represents NH or O;

X$^2$ represents CH$_2$ or O; and wherein X$^1$ and X$^2$ cannot represent oxygen at the same time.

Intermediates of formula (IIa), wherein (G) represents (G$^1$), X represents O and R$^6$ represents chloro, may be prepared from intermediate of formula (IX) wherein X$^1$ represents NH and X$^2$ represents O, hereafter referred to as intermediate of formula (IXa). The reaction is conveniently effected in the presence of thionyl chloride, in a suitable solvent, e.g. dimethyl formamide, at eleveated temperature.

Intermediates of formula (IIa), wherein (G) represents (G$^2$), W$^1$ represents CF$_2$ and W$^2$ represents CH$_2$, may be prepared from intermediate of formula (IX) wherein X$^1$ represents O and $X^2$ represents $CH_2$, hereafter referred to as intermediate of formula (IXb). The reaction is conveniently effected in a two steps: (i) by reacting intermediate of formula (IIa) with Lawesson's reagent, in a suitable solvent, e.g. toluene at elevated temperature, according to methods known to the person skilled in the art and (ii) followed by addition of a fluorinating agent, e.g. tetrabutylammonium dihydrogen trifluoride.

Intermediates of formula (IXa) may be prepared by a process involving multi step reaction of an intermediate of formula (X),

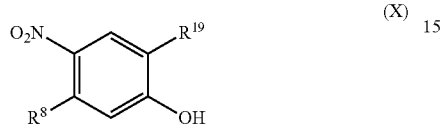

(X)

wherein $R^{19}$ represents —(CO)$R^f$, and $R^f$ represents —OH or —NHOH; and $R^8$ is as defined here above.

In a first step intermediate of formula (X) wherein $R^f$ represents —OH is transformed into corresponding intermediate wherein $R^f$ represents —NHOH, herein after referred to as intermediate of formula (Xa). In a second step, intermediate of formula (Xa) is reacted with 1,1'-carbodimidiazole, in a suitable solvent, e.g. tetrahydrofuran, at elevated temperature.

Intermediates of formula (IIa) wherein (G) represents ($G^5$), wherein X represents O, may be prepared by a process involving reaction of an intermediate of formula (XI),

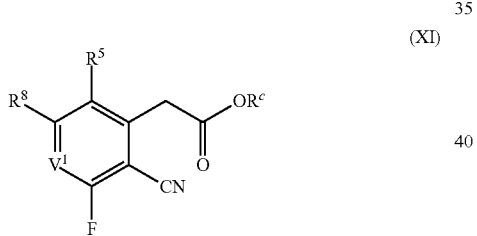

(XI)

wherein $R^5$, $R^8$, $V^1$ and $R^c$ are as defined here above.

The reaction is conveniently effected in the presence of N $H_2OH$, in a suitable solvent, e.g. tetrahydrofuran.

Intermediates of formula G-$R^e$ wherein (G) represents ($G^3$) as defined above, $R^e$ is as defined here above, and $W^2$ represent $CH_2$ may be prepared by a process involving reaction of an intermediate of formula (XII),

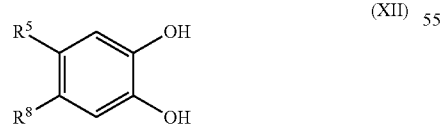

(XII)

wherein $R^5$ and $R^8$ are as defined here above.

Intermediate of formula (XII) is first reacted with $CH_2I_2$ in the presence of a base, e.g. cesium carbonate, in a suitable solvent, e.g. dimethyl formamide, at elevated temperature. Compound ($G^3$)—H, wherein $W^2$ represents $CH_2$, thereby obtained may then be transformed into corresponding compound of formula ($G^3$)-$R^e$ according to standard alkylation methods known to the person skilled in the art, e.g. by reaction with alkyl iodide, in the presence of a suitable base, e.g. n-BuLi, in a suitable solvent, e.g. tetrahydrofuran.

Intermediates of formula G-$R^e$ wherein $R^e$ is as defined here above and (G) represents ($G^6$) as defined here above, may be prepared by a process involving reaction of an intermediate of formula (XIII),

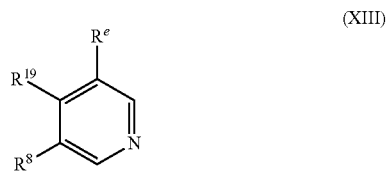

(XIII)

wherein $R^e$, $R^8$ and $R^{19}$ is as defined here above.

When $R^{19}$ represents amino, intermediate of formula (XIII) is reacted (i) with HO—S(O)$_2$—NH$_2$, in a suitable solvent, e.g. water, at elevated temperature, followed by (ii) reaction with methylcarboxyacetylene, in the presence of a base, e.g. potassium carbonate, in a suitable solvent, e.g. dimethylformamide and (iii) decarbalkoxylation at elevated temperature, in the presence of suitable acid, e.g. sulfuric acid.

In the above reactions, the amino group of intermediate of formula (XIII) will generally first be protected with an appropriate protective group, e.g. tert-butoxycarbonyl group, according to methods known to the person skilled in the art.

Intermediates of formula (IIa) wherein (G) represents ($G^4$) may be prepared by a process which involves reaction of an intermediate of formula (XIV),

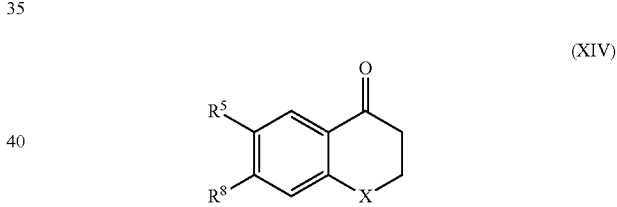

(XIV)

wherein $R^5$, $R^8$ and X are as defined here above.

The reaction may be performed according to analogous conditions to the ones described here above for the synthesis of intermediate of formula (IIa) wherein (G) represents ($G^1$) or ($G^2$) from intermediates of formula (IX).

Alternatively, intermediates of formula (II) wherein (G) represents ($G^6$) may be prepared from intermediates of formula (IIc),

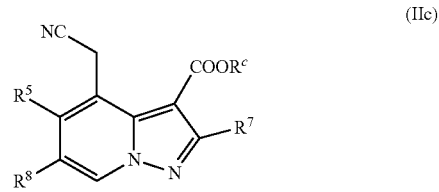

(IIc)

wherein $R^5$, $R^7$, $R^8$ and $R^c$ are as defined above.

Intermediate (IIc) may be prepared from intermediate (XIII), as defined above, wherein $R^{19}$ represents amino and $R^e$ represents methyl, by applying the following sequence of steps:

(i) reacting with O-(2,4-dinitrophenyl)hydroxylamine, in a suitable solvent, e.g. 2-methyltetrahydrofuran,
(ii) subsequent reaction with methylcarboxyacetylene, in the presence of a base, e.g. potassium carbonate, in a suitable solvent, e.g. dimethylformamide,
(iii) halogenation of amino group $R^{19}$ with an halogenating agent such as copper chloride and sodium nitrite, in the presence of an acid such as hydrochloric acid at elevated temperature (Sandmeyer-type reaction), and
(iv) halogenation of $R^e$ and subsequent cyanation according to methods known to the person skilled in the art.

Compounds of formula (I) or intermediates of formula (II) wherein (G) represents ($G^1$), X represents $NR^{11}$ and $R^{11}$ represents hydrogen may be transformed into corresponding compounds of formula (I) or intermediate of formula (II) wherein $R^{11}$ represents $C_{1-6}$ alkyl, by reaction with $C_{1-6}$ alkyl iodide, e.g. methyl iodide, in a suitable solvent, e.g. acetone, according to methods known to the person skilled in the art.

Compounds of formula (I) or intermediates of formula (II) wherein (G) represents ($G^5$), X represents $NR^{11}$, and $R^{11}$ represents hydrogen may be transformed via an analogous process into corresponding compounds of formula (I) or intermediates of formula (II) wherein (G) represents ($G^5$), X represents $NR^{11}$ and $R^{11}$ represents $C_{1-6}$alkyl.

Compounds of formula (I) or intermediates of formula (II) or intermediates of formula (III) comprising an (hetero)aryl-hydrogen moiety may be transformed into the corresponding compound of formula (I), (II) or (III) comprising an (hetero)aryl-chloro or (hetero)aryl-bromo moiety by reaction with respectively N-chloro- or N-bromo-succinimide, according to methods known to the person skilled in the art.

Compounds of formula (I) or intermediates of formula (II) or intermediates of formula (III) comprising an (hetero)aryl-cyano moiety may be prepared from corresponding compounds of formula (I), (II) or (III) comprising an (hetero)aryl-formyl moiety, following a two-step reaction. First step is conveniently effected in the presence of hydroxylamine, in a suitable solvent, e.g. ethanol, according to methods known to the person skilled in the art. The second step is conveniently effected by heating the hydroxyimine obtained as a result of the first step, in a suitable solvent, e.g. acetic acid anhydride.

Compounds of formula (I) or intermediates of formula (II) or intermediates of formula (III) comprising an (hetero)aryl-cyano moiety may alternatively be prepared from corresponding compounds of formula (I), (II) or (III) comprising an (hetero)aryl-formyl moiety in a one step reaction in the presence of ammonium hydroxide and iodine, in a suitable solvent, e.g. THF, according to methods known to the person skilled in the art.

Compounds of formula (I) or intermediates of formula (II) or intermediates of formula (III) comprising an (hetero)aryl-cyano moiety may alternatively be prepared from corresponding compounds of formula (I), (II) or (III) comprising an (hetero)aryl-halogen moiety, by reaction with copper cyanide, in the presence of L-proline, in a suitable solvent, e.g. dimethyl formamide. The reaction is conveniently effected at elevated temperature.

Generally, compounds of formula (I) or intermediates of formula (II) or intermediates of formula (III) comprising an (hetero)aryl-halogen moiety may be prepared from corresponding compounds of formula (I), (II) or (III) comprising an (hetero)aryl-amino moiety, according to methods known to the person skilled in the art.

Compounds of formula (I) or intermediates of formula (II) or intermediates of formula (III) comprising an (hetero)aryl-chloride, (hetero)aryl-bromide, or (hetero)aryl-iodide moiety may be prepared from corresponding compounds of formula (I), (II) or (III) comprising an (hetero)aryl-amino moiety, by reaction with respectively copper chloride, copper bromide or potassium iodide. The reaction is conveniently effected in the presence of sodium nitrite, in a suitable solvent, e.g. acetone, according to methods known to the skilled in the art.

Compounds of formula (I) or intermediates of formula (II) or intermediates of formula (III) comprising an (hetero)aryl-fluoro moiety may be prepared from corresponding compounds of formula (I), (II) or (III), comprising an (hetero)aryl-amino moiety, by reaction with trifluoroborate diethylether, in the presence of tert-butyl nitroxide in a suitable solvent, e.g. tetrahydrofuran, according to methods known to the person skilled in the art.

Compounds of formula (I) or intermediates of formula (II) or intermediates of formula (III) comprising an (hetero)aryl-difluoromethoxy moiety may be prepared from corresponding compounds of formula (I), (II) or (III), comprising an (hetero)aryl-hydroxy moiety, by reaction with diethyl(bromodifluoromethyl)phosphonate, in the presence of a base, e.g. aqueous potassium hydroxide, in a suitable solvent, e.g. acetonitrile.

Compounds of formula (I) or intermediates of formula (II) or intermediates of formula (III) comprising an (hetero)aryl-difluoromethoxy moiety may be prepared from corresponding compounds of formula (I), (II) or (III), comprising an (hetero)aryl-hydroxy moiety, by reaction with ethyl chlorodifluoroacetate, in the presence of a suitable base, e.g. sodium carbonate, in a suitable solvent, e.g. acetonitrile.

Compounds of formula (I) or intermediates of formula (II) or intermediates of formula (III) comprising an (hetero)aryl-$C_{1-6}$alkoxy moiety may be prepared from corresponding compounds of formula (I), (II) or (III), comprising an (hetero)aryl-hydroxy moiety, by reaction with corresponding $C_{1-6}$alkyl-halide, in the presence of a base, e.g. potassium carbonate, in a suitable solvent, e.g. acetonitrile, at elevated temperature.

Compounds of formula (I) or intermediates of formula (II) or intermediates of formula (III) comprising an (hetero)aryl-hydroxy moiety may be prepared from corresponding compounds of formula (I), (II) or (III), comprising an (hetero)aryl-amino moiety. The reaction is conveniently effected with sodium nitrite, in the presence of water, according to methods known to the person skilled in the art.

Compounds of formula (I) or intermediates of formula (II) or intermediates of formula (III) comprising an (hetero)aryl-amino moiety may be prepared from corresponding compounds of formula (I), (II) or (III), comprising an (hetero)aryl-nitro moiety, by reaction with iron metal, in the presence of ammonium chloride, at elevated temperature, according to methods known to the person skilled in the art.

Compounds of formula (I) or intermediates of formula (II) or intermediates of formula (III) comprising an (hetero)aryl-nitro moiety may be prepared from corresponding compounds of formula (I), (II) or (III), comprising an (hetero)aryl-hydrogen moiety, by reaction with nitric acid in the presence of sulphuric acid, according to methods known to the person skilled in the art.

Where a mixture of products is obtained from any of the processes described above for the preparation of compounds or intermediates according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) or of intermediates (II) or (III) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC or chiral SFC Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention. Alternatively the non desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

EXPERIMENTAL SECTION

Abbreviations/Recurrent Reagents
Ac: acetyl
ACN: Acetonitrile
AlBN: Azobisisobutyronitrile
Brine: Saturated aqueous sodium chloride solution
nBu: n-butyl
tBu: tert-butyl
Bz: benzoyl
dba: dibenzylideneacetonate
DCM: Dichloromethane
DHP: Dihydropyrane
DMF: N,N-Dimethylformamide
DMSO: Dimethylsulfoxide
dppf: 1,1'-Bis(diphenylphosphino)ferrocene
$EC_{20/50}$: concentration which produces 20%/50% of the maximum response
Erel: relative efficacy
ES$^+$: Electrospray Positive Ionisation
Et: Ethyl
EtOH: Ethanol
Et$_2$O: Diethyl ether
EtOAc: Ethyl acetate
h: Hour
HEPES: 4-(2-hydroxyethyl)-1-piperazineethanesulfonic acid
HMPA: hexamethylphosphoramide
HPLC: High Pressure Liquid Chromatography
HTRF: homogenous time-resolved fluorescence
LC: Liquid Chromatography
LCMS: Liquid Chromatography Mass Spectrometry
LDA: Lithium diisopropylamide
MeOH: Methanol
min.: minutes
NCS: N-Chlorosuccinimide
NBS: N-Bromosuccinimide
NMR: Nuclear magnetic resonance
iPrOH: isopropanol
PTSA: p-toluenesulfonic acid
rt: room temperature
SFC: Supercritical Fluid Chromatography
TEA: Triethylamine
THF: Tetrahydrofuran
TLC: Thin Layer Chromatography
cAMP: cyclic adenosinemonophosphate
Analytical Methods All reactions involving air or moisture-sensitive reagents were performed under a nitrogen or argon atmosphere using dried solvents and glassware. Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling). Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography, HPLC or mass spectrometry analyses.

HPLC analyses are performed using an Agilent 1100 series HPLC system mounted with a Waters XBridge MS C18, 5 pm, 150×4.6 mm column. The gradient runs from 100% solvent A (water/ACN/ammonium formate solution 85/5/10 (v/v/v)) to 100% solvent B (water/ACN/ammonium formate solution 5/85/10 (v/v/v) in 6 min. with a hold at 100% B of 5 minutes. The flow rate is set at 8 mL/min during 6 min. then increased at 3 mL/min during 2 min. with a hold at 3 mL/min during 3 minutes. A split of 1/25 is used just before API source. The chromatography is carried out at 45° C. The ammonium formate solution (pH~8.5) is prepared by dissolution of ammonium formate (630 mg) in water (1 L) and addition of ammonium hydroxide 30% (500 μL).

It will be apparent to the one skilled in the art that different retention times (RT) may be obtained for LC data if different analytical conditions are used.

Mass spectrometric measurements in LCMS mode are performed as follows:

For Basic Elution, Analyses are Performed Using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an basic elution. The reverse phase separation is carried out at 45° C. on a Waters Acquity UPLC BEHC18 1.7 μm (2.1×50 mm) column for basic elution. Gradient elution is done with water/ACN/ammonium formate (95/5/63 mg/L) (solvent A) and ACN/water/ammonium formate (95/5/63 mg/L) (solvent B). Injection volume: 1 µL. Full flow in MS.

| Basic program "4 min" | | | |
|---|---|---|---|
| Time (min) | A (%) | B (%) | Flow (mL/min) |
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |

| Basic program "10 min" | | | |
|---|---|---|---|
| Time (min) | A (%) | B (%) | Flow (mL/min) |
| 0 | 99 | 1 | 0.4 |
| 0.8 | 99 | 1 | 0.4 |
| 5.3 | 0 | 100 | 0.4 |
| 5.35 | 0 | 100 | 0.5 |
| 7.30 | 0 | 100 | 0.5 |

For Acidic Elution, Analyses are Performed Using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an acidic elution. The reverse phase separation is carried out at 45° C. on a Waters Acquity UPLC HSS T3 1.8 µm (2.1×50 mm) column for acidic elution. Gradient elution is done with water/ACN/TFA (95/5/0.5 mL/L) (solvent A) and ACN (solvent B). Injection volume: 1 µL. Full flow in MS.

| Acidic program "4 min" | | | |
|---|---|---|---|
| Time (min) | A (%) | B (%) | Flow (mL/min) |
| 0 | 99 | 1 | 0.4 |
| 0.3 | 99 | 1 | 0.4 |
| 3.2 | 5 | 95 | 0.4 |
| 3.25 | 5 | 95 | 0.5 |
| 4 | 5 | 95 | 0.5 |

| Acidic program "10 min" | | | |
|---|---|---|---|
| Time (min) | A (%) | B (%) | Flow (mL/min) |
| 0 | 99 | 1 | 0.4 |
| 0.8 | 99 | 1 | 0.4 |
| 5.3 | 5 | 95 | 0.4 |
| 5.35 | 5 | 95 | 0.5 |
| 7.30 | 5 | 95 | 0.5 |

Some reaction mixtures could be treated using Isolute® separator phase cartridges (from Biotage), acidic columns or catch and release SPE (Solid Phase Extraction) cartridges. Crude materials could be purified by normal phase chromatography, (acidic or basic) reverse phase chromatography, chiral separation or recrystallization.

Normal reverse phase chromatography are performed using silica gel columns (100:200 mesh silica gel or Puriflash®-50SIHC-JP columns from Interchim).

Preparative Reverse Phase Chromatography are Performed as Follows:

LCMS purification (Basic mode, LCMS prep) using a SQD or QM Waters triple quadrupole mass spectrometer is used for LCMS purification. This spectrometer is equipped with an ESI source and a Prep LC controller Waters quaternary pump with diode array detector (210 to 400 nm).

MS Parameters:

ESI capillary voltage 3 kV. Cone and Extractor voltage 10. Source block temperature 120° C. Desolvation temperature 300° C. Cone gaz flow 30 L/h (Nitrogen), Desolvation Gas flow 650 L/h. Data are acquired in a full MS scan from m/z 100 to 700 in positive mode with an acidic or a basic elution.

LC Parameters:

The reverse phase separation is carried out at rt on a XBridge prep OBD C18 column (5 µm, 30×50 mm) (basic elution). Gradient elution is done with Water (solvent A), ACN (solvent B), Ammonium bicarbonate in water 8 g/L+ 500 µL/L $NH_4OH$ 30% (solvent C) (pH~8.5). HPLC flow rate: 35 mL/min to 60 mL/min, injection volume: 1 mL. The splitting ratio is set at +/−1/6000 to MS.

| Time (min) | A (%) | B (%) | C (%) | Flow (mL/min) |
|---|---|---|---|---|
| 0 | 85 | 5 | 10 | 35 |
| 1 | 85 | 5 | 10 | 35 |
| 7 | 5 | 85 | 10 | 35 |
| 9 | 5 | 95 | 0 | 60 |
| 12 | 5 | 95 | 0 | 60 |
| 12.5 | 85 | 5 | 10 | 35 |
| 16 | 85 | 5 | 10 | 35 |

Preparative Chiral Chromatographic separations are performed on using liquid phase chromatography or supercritical fluid chromatography (SFC) instruments with various mixtures of lower alcohols and $C_5$ to $C_8$ linear, branched or cyclic alkanes at 360 mL/min. Solvent mixtures as well as columns are described in individual procedures.

Products were generally dried under vacuum before final analyses and submission to biological testing.

NMR spectra are recorded on a BRUKER AVANCEIII 400 MHz-Ultrashield NMR Spectrometer fitted with a Windows 7 Professional workstation running Topspin 3.2 software and a 5 mm Double Resonance Broadband Probe (PABBI 1H/19F-BB Z-GRD Z82021/0075) or a 1 mm Triple Resonance Probe (PATXI 1H/D-13C/15N Z-GRD Z868301/004). The compounds were studied in DMSO-$d_6$, $CDCl_3$ or MeOH-$d_4$ solution at a probe temperature of 300 K and at a concentration of 10 mg/mL. The instrument is locked on the deuterium signal of DMSO-$d_6$, $CDCl_3$ or MeOH-$d_4$. Chemical shifts are given in ppm downfield from TMS (tetramethylsilane) taken as internal standard.

NOMENCLATURE

Compounds in the following section follow the IUPAC naming convetion and were named with the assistance of Biovia Draw 2016.

INTERMEDIATES

A. Synthesis of Intermediates of Formula (II)

A.1. Synthesis of 2-(5-chloro-1H-indazol-4-yl)acetic Acid a7

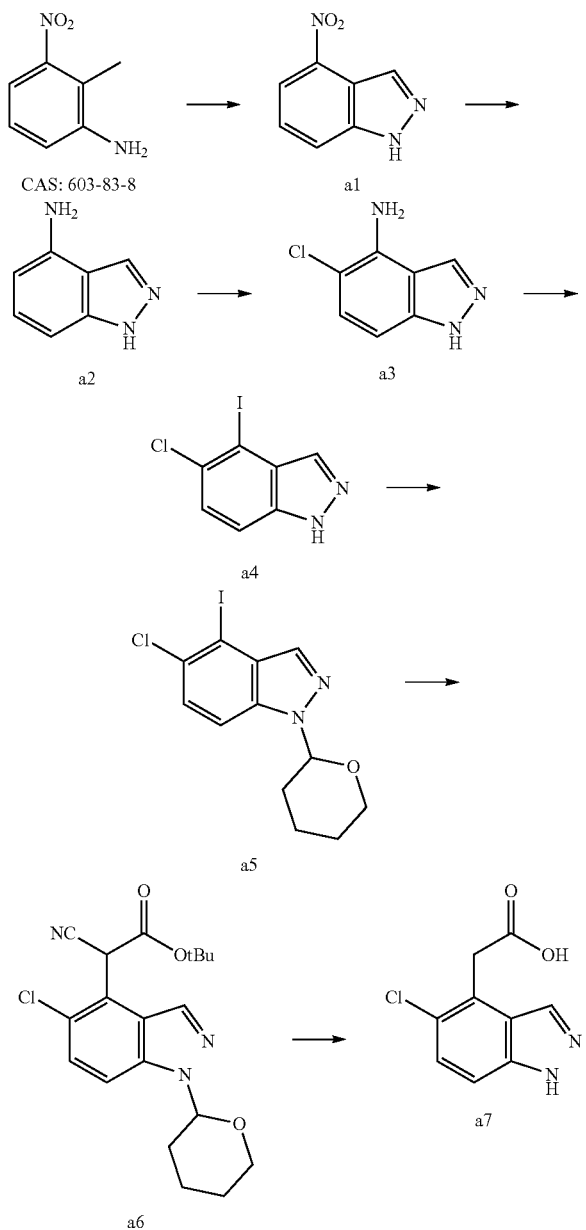

A.1.1. Synthesis of 4-nitro-1H-indazole a1

To a solution of 2-methyl-3-nitroaniline (50 g, 328 mmol) in AcOH (700 mL), a solution of $NaNO_2$ (45.4 g, 657 mmol) in water (100 mL) was added at 0° C. The reaction was stirred at rt for 48 h. Progress of reaction was monitored by TLC. After completion, the reaction mixture was poured onto ice water and filtered. The filtrate was washed with water and dried under vacuum to afford 45 g of 4-nitro-1H-indazole a1.

Yield: 84%.

$^1$H NMR (400 MHz, DMSO-$d_6$) δ 8.53 (s, 1H), 8.15 (d, J=8.03 Hz, 1H), 8.09 (d, J=8.03 Hz, 1H), 7.60 (t, J=8.03 Hz, 2H).

A.1.2. Synthesis of 1H-indazol-4-amine a2

To a solution of 4-nitro-1H-indazole a1 (20 g, 122 mmol) in EtOH (1 L), Pd/C (8 g) was added and the reaction mixture was stirred at rt for 6 h in an autoclave under hydrogen pressure. Progress of reaction was monitored by TLC. After completion, the reaction mixture was filtered through Celite® and the filtrate was evaporated under reduced pressure. The crude product was washed with $Et_2O$ to afford 14 g of 1H-indazol-4-amine a2.

Yield: 86%.

$^1$H NMR (400 MHz, DMSO-$d_6$) δ 12.60 (brs, 1H), 8.07 (s, 1H), 6.97 (dd, J=7.94, 7.50 Hz, 1H), 6.60 (d, J=7.94 Hz, 1H), 6.11 (d, J=7.50 Hz, 1H), 5.69 (brs, 2H).

A.1.3. Synthesis of 5-chloro-1H-indazol-4-amine a3

To a solution of 1H-indazol-4-amine a2 (10 g, 75.10 mmol) in THF (600 mL), $H_2SO_4$ (1.34 mL, 7.51 mmol) was added at −78° C. and stirred at same temperature for 5 min followed by addition of NCS (10 g, 75.18 mmol) solution in THF (100 mL) at same temperature. The reaction was stirred at −78° C. for 2 h. Progress of reaction was monitored by TLC. After completion of reaction, $Na_2CO_3$ was added at −78° C. and allowed to warm up to rt. The reaction was diluted with water and extracted with EtOAc. The organic layer was washed with brine, dried over $Na_2SO_4$ and concentrated under vacuum. The crude product was purified by column chromatography using 30% EtOAc in n-hexanes as eluent to afford 10 g of 5-chloro-1H-indazol-4-amine a3.

Yield: 79%

LCMS (ES$^+$): 168 (M+H)$^+$ $^1$H NMR (400 MHz, DMSO-$d_6$) δ 12.82 (brs, 1H), 8.13-8.23 (m, 1H), 7.08 (d, J=8.32 Hz, 1H), 6.66 (d, J=8.79 Hz, 1H), 5.95 (s, 2H).

A.1.4. Synthesis of 5-chloro-4-iodo-1H-indazole a4

To a solution of 5-chloro-1H-indazol-4-amine a3 (50 g, 299 mmol) in a 6N aqueous solution of HCl (3.3 L) at 0° C., a solution of $NaNO_2$ (31 g, 448 mmol) in water (1 L) was added. The reaction mixture was stirred at 0° C. for 30 min, then a solution of KI (99.26 g, 598 mmol) in water (1 L) was added dropwise at 0° C. The reaction mixture was stirred at rt for 1 h. Progress of reaction was monitored by TLC. After completion, EtOAc was added. The organic layer was washed with an aqueous saturated solution of sodium bicarbonate, dried over $Na_2SO_4$ and concentrated under vacuum. The crude product was purified by column chromatography using 10% EtOAc in n-hexanes as eluent to afford 30 g of 5-chloro-4-iodo-1H-indazole a4.

Yield: 36%.

LCMS (ES$^+$): 279 (M+H)$^+$.

$^1$H NMR (400 MHz, DMSO-$d_6$) δ 13.44-13.66 (m, 1H), 7.88 (s, 1H), 7.56-7.64 (m, 1H), 7.44-7.50 (m, 1H).

A.1.5. Synthesis of 5-chloro-4-iodo-1-tetrahydropyran-2-yl-indazole a5

To a solution of 5-chloro-4-iodo-1H-indazole a4 (30 g, 107 mmol) in chloroform (600 mL), PTSA (4.1 g, 21.5 mmol) was added followed by addition of DHP (27 g, 321 mmol) at 0° C. The reaction was stirred at rt for 16 h. Progress of reaction was monitored by TLC. After completion, the reaction was evaporated under vacuum. The residue was dissolved in EtOAc and successively washed with water, an aqueous saturated solution of sodium bicarbonate and water. The organic layer was dried over $Na_2SO_4$ and concentrated under vacuum. The crude residue was purified by column chromatography using 6% EtOAc in n-hexanes as eluent to afford 28 g of 5-chloro-4-iodo-1-tetrahydropyran-2-yl-indazole a5.

Yield: 72%.

LCMS (ES+): 362 (M+H)+.

A.1.6. Synthesis of tert-butyl 2-(5-chloro-1-tetrahydropyran-2-yl-indazol-4-yl)-2-cyano-acetate a6

To a solution of 5-chloro-4-iodo-1-tetrahydropyran-2-yl-indazole a5 (11 g, 30.38 mmol) in DMF (150 mL), CuI (1.27 g, 6.68 mmol), $Cs_2CO_3$ (24.76 g, 75.95 mmol) and tert-butyl 2-cyanoacetate (8.57 g, 60.77 mmol) were added and the reaction was heated at 80° C. for 16 h. Progress of reaction was monitored by TLC. After completion, cold water was added and mixture was extracted with EtOAc. The organic layer was washed with brine, dried over $Na_2SO_4$ and concentrated under vacuum. The crude compound was purified by column chromatography using 5% EtOAc in n-hexanes as eluent to afford 8 g of tert-butyl 2-(5-chloro-1-tetrahydropyran-2-yl-indazol-4-yl)-2-cyano-acetate a6.

Yield: 70%.

LCMS (ES+): 376 (M+H)+.

$^1$H NMR (400 MHz, DMSO-$d_6$) δ 8.35 (d, J=1.75 Hz, 1H), 7.88 (d, J=8.77 Hz, 1H), 7.58 (d, J=8.77 Hz, 1H), 6.33 (d, J=2.63 Hz, 1H), 5.92 (d, J=9.65 Hz, 1H), 3.83-3.94 (m, 1H), 3.71-3.82 (m, 1H), 2.29-2.46 (m, 1H), 1.63-1.84 (m, 2H), 1.44 (m, 3H), 1.40 (s, 9H).

A.1.7. Synthesis of 2-(5-chloro-1H-indazol-4-yl)acetic Acid a7

A stirred solution of tert-butyl 2-(5-chloro-1-tetrahydropyran-2-yl-indazol-4-yl)-2-cyano-acetate a6 (7 g, 18.67 mmol) in a 6N aqueous solution of HCl (70 mL) was heated at 95° C. for 16 h. Progress of reaction was monitored by TLC. After completion, the reaction was basified with an aqueous saturated solution of sodium bicarbonate and washed with EtOAc. The aqueous layer was acidified with a 6N aqueous solution of HCl up to pH5 and extracted with EtOAc. The organic layer was dried over $Na_2SO_4$ and concentrated under vacuum. The residue was triturated with $Et_2O$ to afford 2 g of 2-(5-chloro-1H-indazol-4-yl)acetic acid a7.

Yield: 51%.

LCMS (ES+): 211 (M+H)+.

$^1$H NMR (400 MHz, DMSO-$d_6$) δ 13.21 (brs, 1H), 12.54 (brs, 1H), 8.20 (s, 1H), 7.48 (d, J=8.79 Hz, 1H), 7.36 (d, J=8.79 Hz, 1H), 4.02 (s, 2H).

A.2. Synthesis of 2-(5-chloro-2-methyl-indazol-4-yl)acetic Acid a10

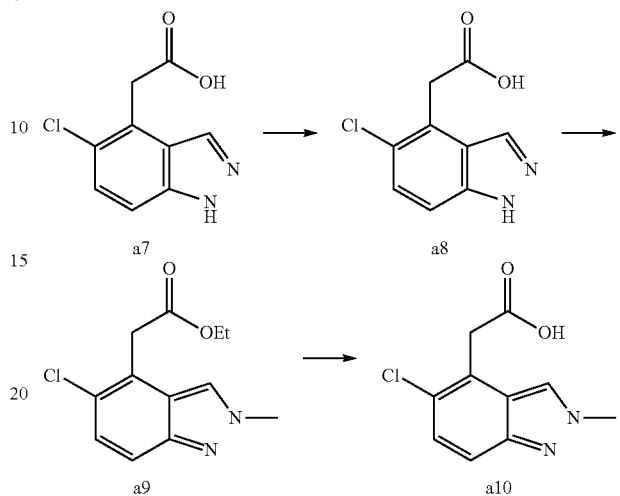

A.2.1. Synthesis of ethyl 5-chloro-1H-indazole-4-carboxylate a8

Thionyl chloride (1.1 mL, 10 mmol) was added dropwise at 0° C. to a solution of 5-chloro-1H-indazole-4-carboxylic acid a7 (1 g, 4.76 mmol) in EtOH (5 mL) was stirred at 40° C. for 4 h. Progress of reaction was monitored by LCMS. After completion, the reaction mixture was concentrated under vacuum to afford 1.39 g of ethyl 5-chloro-1H-indazole-4-carboxylate a8, which was used in next step without any further purification.

Yield (crude): quantitative. LCMS (ES+): 239/241 (M+H)+.

A.2.2. Synthesis of ethyl 2-(5-chloro-2-methyl-indazol-4-yl)acetate a9

Trimethyloxonium tetrafluoroborate (203 µL, 3.15 mmol) was added at rt to a solution of ethyl 5-chloro-1H-indazole-4-carboxylate a8 (409 mg, 1.49 mmol) in DCM (1 mL) was stirred overnight at rt. Progress of reaction was monitored by LCMS. After completion, the reaction mixture was concentrated under vacuum. The residue was purified by column chromatography using 5% EtOH in DCM (+0.5% $NH_4OH$) as eluent to afford 379 mg of ethyl 2-(5-chloro-2-methyl-indazol-4-yl)acetate a9.

Yield (crude): quantitative.

LCMS (ES+): 253/255 (M+H)+.

$^1$H NMR (400 MHz, DMSO-$d_6$) δ8.44 (s, 1H), 7.56 (d, J=9.1 Hz, 1H), 7.24 (d, J=9.0 Hz, 1H), 4.19 4.05 (m, 5H), 4.01 (s, 2H), 1.18 (t, J=7.1 Hz, 3H).

A.2.3. Synthesis of 2-(5-chloro-2-methyl-indazol-4-yl)acetic Acid a10

Lithium hydroxide monohydrate (96 mg, 2.24 mmol) was added at rt to a solution of ethyl 2-(5-chloro-2-methyl-indazol-4-yl)acetate a9 (379 mg, 1.50 mmol) in THF/water (1:1, 10 mL). The reaction mixture was stirred overnight at rt, then quenched with water (20 mL) and extracted with EtOAc (20 mL). The organic layer was acidified with a 1N aqueous solution of HCl, extracted with EtOAc (3×30 mL) dried over Na$_2$SO$_4$ and concentrated under vacuum to afford 262 mg of 2-(5-chloro-2-methyl-indazol-4-yl)acetic acid a10 as a white solid, which was used in next step without any further purification.

Yield (crude): 78%.

LCMS (ES$^+$): 225/227 (M+H)$^+$.

A.3. Synthesis of 2-(5-chloro-1-methyl-indazol-4-yl)acetic Acid a11

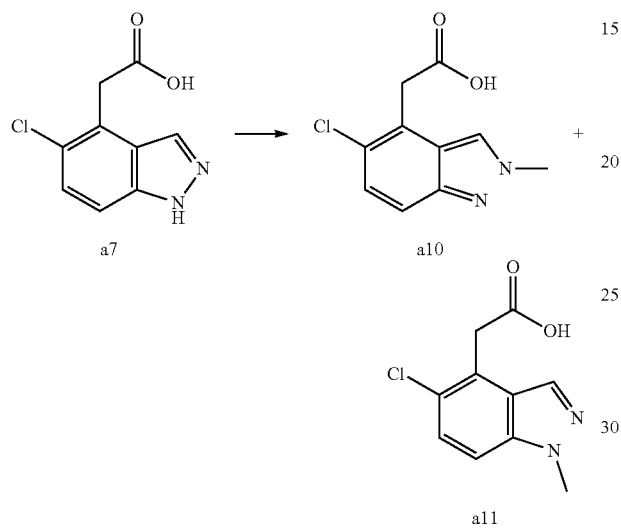

Potassium hydroxyde (1.61 g, 28.5 mmol) was added to a solution of 5-chloro-1H-indazole-4-carboxylic acid a7 (1.00 g, 4.75 mmol) in acetone (15 mL) was stirred at rt. After 30 min at rt, iodomethane (0.9 mL, 14.25 mmol) was added and the reaction mixture was stirred at the same temperature for a few days. Progress of reaction was monitored by LCMS. After completion, the reaction mixture was quenched with water (2×20 mL) and extracted with EtOAc (20 mL). The organic layer was acidified with a 1N aqueous solution of HCl, extracted with EtOAc (3×30 mL), dried over Na$_2$SO$_4$ and concentrated under vacuum to afford 856 mg of a ~1:1 mixture of 2-(5-chloro-2-methyl-indazol-4-yl) acetic Acid a10 and 2-(5-chloro-1-methyl-indazol-4-yl)acetic acid a11 as a brown solid, which was used in next step without any further purification.

Yield (crude): 80%.

LCMS (ES$^+$): 225/227 (M+H)$^+$.

A.4. Synthesis of 2-(3,5-dichloro-1,2-benzoxazol-4-yl)acetic Acid a18

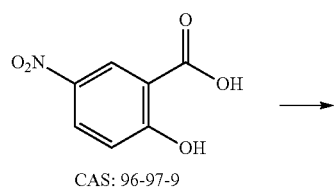

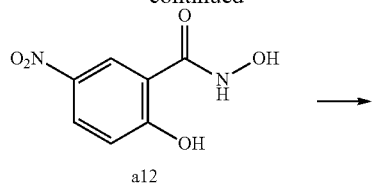

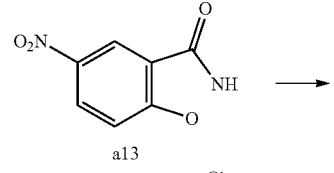

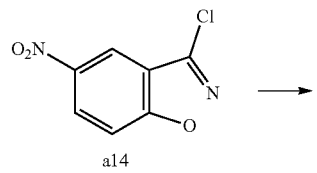

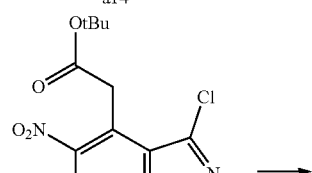

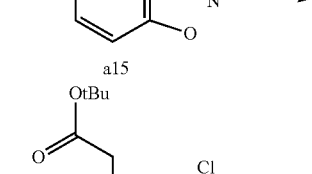

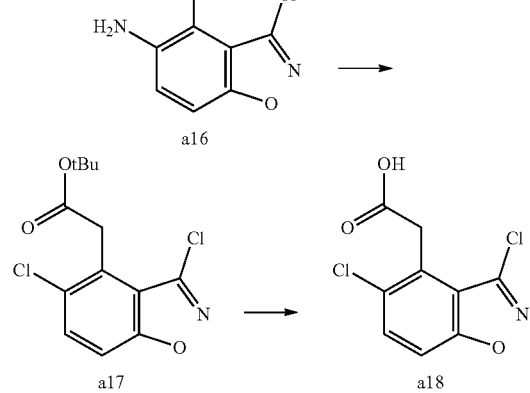

A.4.1. Synthesis of 2-hydroxy-5-nitro-benzenecarbohydroxamic Acid a12

Catalytic DMF (4 drops) was added at rt to a solution of 5-nitrosalicylic acid (commercial, 5.00 g, 27.3 mmol) in thionyl chloride (50 mL). The reaction mixture was heated at reflux for 4 h, then concentrated under vacuum. The residue was taken up in dioxane (20 mL) and a solution of 50% hydroxylamine in water (10 mL, 164 mmol) was added at 0° C. The reaction mixture was then stirred at rt and diluted with Et$_2$O. The obtained precipitate was filtered off and rinsed with Et$_2$O to afford 7.13 g of 2-hydroxy-5-nitro-benzenecarbohydroxamic acid a12, which was used in next step without any further purification.

Yield (crude): quantitative.

A.4.2. Synthesis of 5-nitro-1,2-benzoxazol-3-one a13

A solution of 2-hydroxy-5-nitro-benzenecarbohydroxamic acid a12 (3.00 g, 15.1 mmol) in THF (60 mL) was heated at reflux, then a solution of 1,1'-carbodiimidazole (4.91 g, 30.3 mmol) in THF (40 mL) was added at reflux. The reaction mixture was heated at reflux overnight, then concentrated under vacuum. The residue was taken up with water, then the mixture was acidified to pH1 with concentrated HCl and filtered. The filtrate was diluted with EtOAc and water. The organic layer was extracted with an aqueous saturated solution of NaHCO$_3$. The aqueous layer was then acidified to pH2 with concentrated HCl. The resulting precipitate was filtered off to afford 788 mg of 5-nitro-1,2-benzoxazol-3-one a13.

Yield: 29%.

$^1$H NMR (400 MHz, DMSO-d$_6$) δ 13.04 (s, 1H), 8.73 (d, J=2.4 Hz, 1H), 8.46 (dd, J=9.2, 2.4 Hz, 1H), 7.81 (d, J=9.2 Hz, 1H).

A.4.3. Synthesis of 3-chloro-5-nitro-1,2-benzoxazole a14

A solution of 5-nitro-1,2-benzoxazol-3-one a13 (1.45 g, 8.05 mmol) in phosphoryl chloride (12 mL, 0.13 mmol) was heated at 150° C. for 2 days. The reaction mixture was neutralized with an aqueous saturated solution of NaHCO$_3$, then solid K$_2$CO$_3$, and extracted with DCM. The organic layer was dried over MgSO$_4$ and concentrated under vacuum to yield 1.3 g of 3-chloro-5-nitro-1,2-benzoxazole a14.

Yield (crude): 82%.

GC-MS: 199 (M$^+$)

$^1$H NMR (400 MHz, DMSO-d$_6$) δ 8.82 (d, J=2.3 Hz, 1H), 8.66 (dd, J=9.2, 2.3 Hz, 1H), 8.18 (d, J=9.3 Hz, 1H).

A.4.4. Synthesis of tert-butyl 2-(3-chloro-5-nitro-1,2-benzoxazol-4-yl)acetate a15 tert-Butyl chloroacetate (1.07 mL, 0.28 mmol) and a solution of 3-chloro-5-nitro-1,2-benzoxazole a14 (1.31 g, 6.61 mmol) in DMSO (20 mL) were added to a solution of tea-BuOK (4.37 g, 38.98 mmol) in DMSO (20 mL). The reaction mixture was stirred at rt for 2 h, then brine was added. The mixture was extracted with EtOAc. The organic layer was washed thrice with brine, dried over MgSO$_4$ and concentrated under vacuum to afford 1.31 g of tert-butyl 2-(3-chloro-5-nitro-1,2-benzoxazol-4-yl)acetate a15.

Yield (crude): 63.5%.

GC-MS: 257 (M-tBu)$^+$ $^1$H NMR (400 MHz, DMSO-d$_6$) δ 8.41 (d, J=9.2 Hz, 1H), 8.05 (d, J=9.2 Hz, 1H), 4.34 (s, 2H), 1.40 (s, 9H).

A.4.5. Synthesis of tert-butyl 2-(5-amino-3-chloro-1,2-benzoxazol-4-yl)acetate a16 tert-Butyl 2-(3-chloro-5-nitro-1,2-benzoxazol-4-yl)acetate a15 (1.31 g, 4.20 mmol) and iron (1.17 g, 20.98 mmol) in a mixture EtOH/1N aqHCl (4:1, 50 mL) and the reaction mixture was stirred at rt for 2 h. The mixture was filtered and concentrated under vacuum. The residue was purified by column chromatography using from 0 to 1% MeOH in DCM as eluent to yield 677 mg of tert-butyl 2-(5-amino-3-chloro-1,2-benzoxazol-4-yl)acetate a16.

Yield: 57%.

LCMS (ES$^+$): 227/229 (M-tBu+H)$^+$.

A.4.6. Synthesis of tert-butyl 2-(3,5-dichloro-1,2-benzoxazol-4-yl)acetate a17

A solution of concentrated HCl (330 µL, 3.84 mmol) was added to a solution of tert-butyl 2-(5-amino-3-chloro-1,2-benzoxazol-4-yl)acetate a16 (434 mg, 1.53 mmol) in acetone (10 mL). The reaction, mixture was cooled down to 0° C., then a solution of sodium nitrite (127 mg, 1.84 mmol) in water (800 µL). The mixture was stirred at 0° C. for 10 min, then a solution of copper(I) chloride (304 mg, 3.07 mmol) in water (1 mL) was added. The reaction mixture was stirred at rt overnight, then concentrated under vacuum to afford 270 mg of tert-butyl 2-(3,5-dichloro-1,2-benzoxazol-4-yl)acetate a17, which was used in next step without any further purification.

A.4.7. Synthesis of 2-(3,5-dichloro-1,2-benzoxazol-4-yl)acetic Acid a18 tert-Butyl 2-(5-amino-3-chloro-1,2-benzoxazol-4-yl)acetate a17 (270 mg, 0.89 mmol) was dissolved in a 1N solution of HCl in dioxane (8 mL). The reaction mixture was stirred at rt for 3 h, then concentrated under vacuum to yield 270 mg of 2-(3,5-dichloro-1,2-benzoxazol-4-yl)acetic acid a18, which was used in next step without any further purification.

Yield (crude): 72% over 2 steps.

A.5. Synthesis of 2-(5-chloro-1-tetrahydropyran-2-yl-pyrazolo[3,4-b]pyridin-4-yl)acetic Acid a45

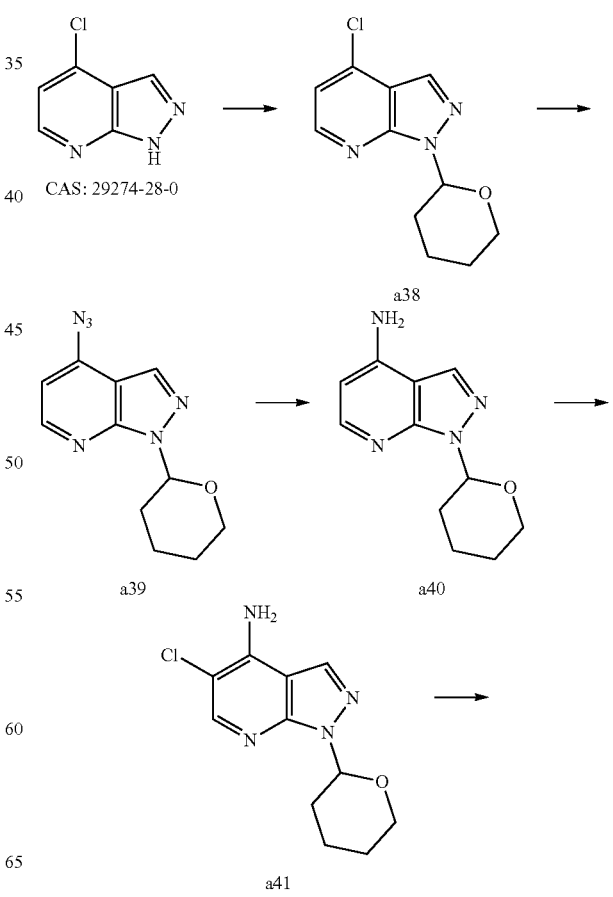

CAS: 29274-28-0 a38 a39 a40 a41

-continued

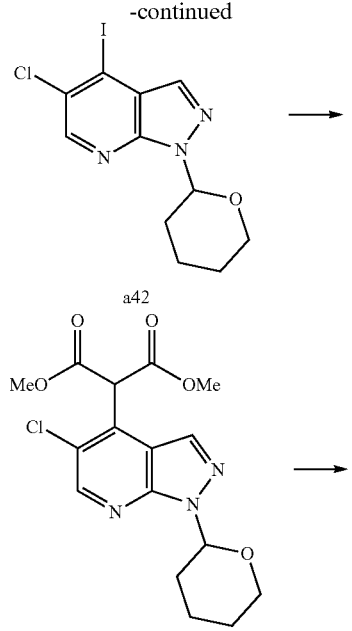

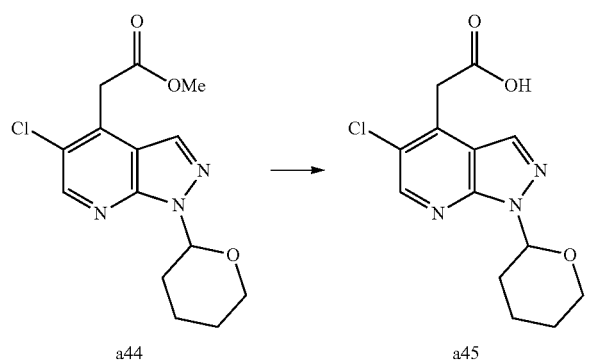 [SMILES: COC(=O)Cc1c(Cl)cnc2c1cnn2C1CCCCO1 ; O=C(O)Cc1c(Cl)cnc2c1cnn2C1CCCCO1]

A.5.1. Synthesis of 4-chloro-1-tetrahydropyran-2-yl-pyrazolo[3,4-b]pyridine a38

To a solution of 4-chloro-1H-pyrazolo[3,4-b]pyridine (5 g, 32.5 mmol) in DCM (50 mL) was added PTSA.H$_2$O (6.19 g, 32.5 mmol) and DHP (8.77 mL, 97.5 mmol) at 0° C. The reaction mixture was stirred at rt for 16 h. Progress of the reaction was monitored by TLC and LCMS. After completion, the reaction mixture was quenched with an aqueous saturated solution of NaHCO$_3$ (150 mL) and extracted with DCM (3×100 mL). The organic layer was dried over anhydrous Na$_2$SO$_4$ and concentrated under vacuum. The crude residue was purified by column chromatography using 20% EtOAc in n-hexanes as eluent to afford 4.45 g of 4-chloro-1-(tetrahydro-2H-pyran-2-yl)-1H-pyrazolo[3,4-b]pyridine a38 as a white solid.

Yield: 58%.

LCMS (ES$^+$): 238.0 (M+H)$^+$, 99% purity.

$^1$H NMR (400 MHz, DMSO-d$_6$) δ 8.55 (d, J=8 Hz, 1H), 8.37 (s, 1H), 7.46 (d, J=4.9 Hz, 1H), 6.04 (dd, J=10.3 Hz, 2.45 Hz, 1H), 3.89-4.02 (m, 1H), 3.64-3.77 (m, 1H), 1.98-2.11 (m, 1H), 1.89-1.97 (m, 1H), 1.73-1.84 (m, 1H), 1.54-1.62 (m, 3H).

A.5.2. Synthesis of 4-azido-1-tetrahydropyran-2-yl-pyrazolo[3,4-b]pyridine a39

To a solution of 4-chloro-1-(tetrahydro-2H-pyran-2-yl)-1H-pyrazolo[3,4-b]pyridine a38 (4.40 g, 18.5 mmol) in DMF (60 mL) was added NaN$_3$ (3.39 g, 52.2 mmol) and the reaction mixture was heated at 100° C. for 16 h. Progress of the reaction was monitored by TLC. After completion, the reaction mixture was diluted with water (250 mL) and extracted with EtOAc (3×70 mL). The organic layer was washed with brine (3×120 mL), dried over anhydrous Na$_2$SO$_4$ and concentrated under vacuum to afford 3.44 g of 4-azido-1-(tetrahydro-2H-pyran-2-yl)-1H-pyrazolo[3,4-b]pyridine a39 as a brown semi solid.

Yield: 76%.

LCMS (ES$^+$): 245.0 (M+H)$^+$, 79% purity.

$^1$H NMR (400 MHz, DMSO-d$_6$) δ 8.50 (d, J=5.37 Hz, 1H), 8.21 (s, 1H), 7.12 (d, J=5.38 Hz, 1H), 6.01 (dd, J=10.27, 2.45 Hz, 1H), 3.94 (m, 1H), 3.63-3.76 (m, 2H), 1.97-2.09 (m, 2H), 1.84-1.96 (m, 1H), 1.66-1.83 (m, 2H).

A.5.3. Synthesis of 1-tetrahydropyran-2-ylpyrazolo[3,4-b]pyridin-4-amine a40

To a solution of 4-azido-1-(tetrahydro-2H-pyran-2-yl)-1H-pyrazolo[3,4-b]pyridine a39 (3.4 g, 13.9 mmol) in MeOH (44 mL) was added Pd/C (0.18 g) and the reaction mixture was stirred at rt for 5 h under pressure of hydrogen. Progress of the reaction was monitored by TLC and LCMS. After completion, the reaction mixture was filtered through Celite® and the filtrate was concentrated under vacuum. The crude residue was purified by column chromatography using 2% MeOH in DCM as eluent to afford 2.49 g of 1-(tetrahydro-2H-pyran-2-yl)-1H-pyrazolo[3,4-b]pyridin-4-amine a40 as a brown solid.

Yield: 82%.

LCMS (ES$^+$): 219.0 (M+H)$^+$, 96% purity.

$^1$H NMR (400 MHz, DMSO-d$_6$) δ 8.11 (s, 1H), 7.92 (d, J=5.38 Hz, 1H), 6.87 (s, 2H), 6.19 (d, J=5.38 Hz, 1H), 5.84 (dd, J=10.27, 1.96 Hz, 1H), 3.88-3.96 (m, 1H), 3.59-3.68 (m, 1H), 1.98-2.04 (m, 1H), 1.69-1.84 (m, 3H), 1.50-1.58 (m, 2H).

A.5.4. Synthesis of 5-chloro-1-tetrahydropyran-2-yl-pyrazolo[3,4-b]pyridin-4-amine a41

To a solution of 1-(tetrahydro-2H-pyran-2-yl)-1H-pyrazolo[3,4-b]pyridin-4-amine a40 (2.49 g, 11.4 mmol) in DCM (30 mL) was added NCS (1.51 g, 11.4 mmol) at 0° C. and the reaction mixture was stirred at rt for 2 h. Progress of the reaction was monitored by TLC and LCMS. After completion, the reaction mixture was quenched with an aqueous saturated solution of NaHCO$_3$ (150 mL) and extracted with DCM (3×60 mL). The organic layer was dried over anhydrous Na$_2$SO$_4$ and concentrated under vacuum. The crude obtained was purified by column chromatography using 2% MeOH in DCM as eluent to afford 2.7 g of 5-chloro-1-(tetrahydro-2H-pyran-2-yl)-1H-pyrazolo[3,4-b]pyridin-4-amine a41 as a yellow solid.

Yield: 93%.

LCMS (ES$^+$): 253.0 (M+H)$^+$, 99% purity.

$^1$H NMR (400 MHz, DMSO-d$_6$) δ 8.21 (s, 1H), 8.07 (s, 1H), 7.20 (brs, 2H), 5.83 (dd, J=10.5, 2.2 Hz, 1H), 3.88-3.94 (m, 1H), 3.59-3.66 (m, 1H), 2.36-2.46 (m, 1H), 1.96-2.04 (m, 1H), 1.66-1.87 (m, 2H), 1.52-1.58 (m, 2H).

A.5.5. Synthesis of 5-chloro-4-iodo-1-tetrahydropyran-2-yl-pyrazolo[3,4-b]pyridine a42

A stirred solution of CuI (4.70 g, 21.4 mmol) in CH₃CN (56 mL) was heated at 50° C. followed by addition of tBuONO (6.19 mL, 53.5 mmol) at 50° C. The reaction mixture was stirred at 50° C. for 30 min. 5-Chloro-1-(tetrahydro-2H-pyran-2-yl)-1H-pyrazolo[3,4-b]pyridin-4-amine a41 (2.70 g, 10.7 mmol) was added at 50° C. and the reaction mixture was heated at 80° C. for 2 h. Progress of the reaction was monitored by TLC. After completion, the reaction mixture was quenched with an aqueous saturated solution of NaHCO₃ (500 mL) and extracted with EtOAc (3×500 mL). The organic layer was dried over anhydrous Na₂SO₄ and concentrated under vacuum. The crude residue was purified by column chromatography using 1% MeOH in DCM as eluent to afford 2.6 g of 5-chloro-4-iodo-1-(tetrahydro-2H-pyran-2-yl)-1H-pyrazolo[3,4-b]pyridine a42 as a yellow solid.

Yield: 67%.

LCMS (ES⁺): 364.0 (M+H)⁺, 98.9% purity.

¹H NMR (400 MHz, DMSO-d₆) δ 8.56 (s, 1H), 8.06 (s, 1H), 5.96 (dd, J=10.03, 2.20 Hz, 1H), 3.90-3.96 (m, 1H), 3.64-3.70 (m, 1H), 2.39-2.44 (m, 1H), 2.00-2.14 (m, 1H), 1.86-1.92 (m, 1H), 1.72-1.84 (m, 1H), 1.52-1.60 (m, 2H).

A.5.6. Synthesis of dimethyl 2-(5-chloro-1-tetrahydropyran-2-yl-pyrazolo[3,4-b]pyridin-4-yl)propanedioate a43

To a solution of 5-chloro-4-iodo-1-tetrahydropyran-2-yl-pyrazolo[3,4-b]pyridine a42 (120 g, 330.6 mmol) and Cs₂CO₃ (215.07 g, 660.10 mmol) in DMSO (1.2 L) was added dimethylmalonate (52.33 g, 396.06 mmol), then the reaction mixture was stirred at 100° C. for 5 h. Progress of the reaction was monitored by LCMS. After completion, the reaction mixture was filtered, then water (2.4 L) was added to the filtrate. The organic layer was extracted with EtOAc (2×2.4 L), dried and concentrated under vacuum to afford 360 g of crude di methyl 2-(5-chloro-1-tetrahydropyran-2-yl-pyrazolo[3,4-b]pyridin-4-yl)propanedioate a43 as a yellow oil, which was used in the next step without further purification.

A.5.7. Synthesis of methyl 2-(5-chloro-1-tetrahydropyran-2-yl-pyrazolo[3,4-b]pyridin-4-yl)acetate a44

To a solution of dimethyl 2-(5-chloro-1-tetrahydropyran-2-yl-pyrazolo[3,4-b]pyridin-4-yl)propanedioate a43 (330.6 mmol) in DMSO (1200 mL) were added LiCl (27.66 g, 652.56 mmol) and water (120 mL), then the reaction mixture was stirred at 100° C. for 16 h. Progress of the reaction was monitored by HPLC. After completion, the reaction mixture was filtered, then water (2.4 L) was added to the filtrate. The organic layer was extracted with EtOAc (2×2.4 L), dried and concentrated under vacuum. The crude residue was purified by column chromatography using from 5% to 50% EtOAc in petroleum ether, then the product was washed with a solution of petroleum ether and EtOAc (6:1, 1.4 L) to afford 140 g of methyl 2-(5-chloro-1-tetrahydropyran-2-yl-pyrazolo[3,4-b]pyridin-4-yl)acetate a44 as a white solid.

Yield: quantitative.

¹H NMR (400 MHz, CD₃OD) δ 8.53 (s, 1H), 8.22 (s, 1H), 6.08-6.05 (dd, J=10.4 Hz, 1H), 4.21 (s, 2H), 4.06-4.02 (m, 1H), 3.83-3.80 (m, 1H), 3.71 (s, 3H), 2.65-2.56 (m, 1H), 2.12 (m, 1H), 1.97-1.93 (m, 1H), 1.85-1.65 (m, 3H).

A.5.8. Synthesis of 2-(5-chloro-1-tetrahydropyran-2-yl-pyrazolo[3,4-b]pyridin-4-yl)acetic acid a45

To a solution of a44 (1.2 g, 3.9 mmol) in THF/water (14:2 mL) was added lithium hydroxide monohydrate (250 mg, 5.8 mmol). The reaction mixture was stirred at rt for 1 h, then concentrated under vacuum to afford 1.26 g of 2-(5-chloro-1-methyl-pyrazolo[3,4-b]pyridin-4-yl)acetic acid a45, which was used in next step without further purification.

Yield (crude): quantitative.

LCMS (ES⁺): 296.0/298.0 (M+H)⁺.

A.6. Synthesis of 2-(5-chloropyrazolo[1,5-a]pyridin-4-yl) acetic Acid a48

A.6.1. Synthesis of methyl 2-(5-chloro-1H-pyrazolo[3,4-b]pyridin-4-yl)acetate a46

To a stirred solution of methyl 2-(5-chloro-1-tetrahydropyran-2-yl-pyrazolo[3,4-b]pyridin-4-yl)acetate a44 (3.0 g, 9.7 mmol) in DCM (60 mL) at rt was added a 4N solution of HCl in dioxane (12 mL, 48 mmol). The reaction mixture was stirred at rt for 22 h, then concentrated under vacuum. The crude residue was purified by column chromatography using from 50% MeOH in DCM to 100% MeOH as eluent to afford 1.63 g of methyl 2-(5-chloro-1H-pyrazolo[3,4-b]pyridin-4-yl)acetate a46 as an off-white solid.

Yield: 75%.

LCMS (ES$^+$): 226.2/228.2 (M+H)$^+$.

$^1$H NMR (300 MHz, DMSO-d$_6$) δ 13.89 (s, 1H), 8.54 (s, 1H), 8.32 (s, 1H), 4.23 (s, 2H), 3.65 (s, 3H).

A.6.2. Synthesis of methyl 2-(5-chloro-1-methyl-pyrazolo[3,4-b]pyridin-4-yl)acetate a47

To a solution of methyl 2-(5-chloro-1H-pyrazolo[3,4-b]pyridin-4-yl)acetate a46 (1.52 g, 6.74 mmol) in DMF (10 mL) stirred under nitrogen were added iodomethane (0.5 mL, 8 mmol) and K$_2$CO$_3$ (1.4 g, 10 mmol). The reaction mixture was stirred at rt for 23 h, then quenched with an aqueous saturated solution of NH$_4$Cl (70 mL) and extracted with EtOAc (2×70 mL). The organic layer was successively washed with water (3×70 mL), brine (70 mL), then dried over anhydrous Na$_2$SO$_4$ and concentrated under vacuum. The crude residue was purified by column chromatography using from 0% to 100% EtOAc in iso-hexane, followed by 1% to 20% MeOH in EtOAc to yield 692 mg of methyl 2-(5-chloro-1-methyl-pyrazolo[3,4-b]pyridin-4-yl)acetate a47 as a colourless oil which crystallised out to a white solid.

Yield: 43%.

LCMS (ES$^+$): 240.2/242.2 (M+H)$^+$.

$^1$H NMR (300 MHz, CDCl$_3$) δ 8.50 (s, 1H), 7.99 (s, 1H), 4.14 (s, 3H), 4.08 (s, 2H), 3.73 (s, 3H).

A.6.3. Synthesis of 2-(5-chloro-1-methyl-pyrazolo[3,4-b]pyridin-4-yl)acetic Acid a48

To a solution of methyl 2-(5-chloro-1-methyl-pyrazolo[3,4-b]pyridin-4-yl)acetate a47 (300 mg, 1.25 mmol) in THF/water (6:2 mL) was added lithium hydroxide monohydrate (59 mg, 1.38 mmol). The reaction mixture was stirred at rt for 1 h, tehn concentrated under vacuum to afford 282 mg of 2-(5-chloro-1-methyl-pyrazolo[3,4-b]pyridin-4-yl)acetic acid a48, which was used in next step without further purification. Yield(crude): quantitative.

LCMS (ES$^+$): 225.9/227.9 (M+H)$^+$.

A.7. Synthesis of 2-(3,5-dichloropyrazolo[1,5-a]pyridin-4-yl)acetic Acid a56b

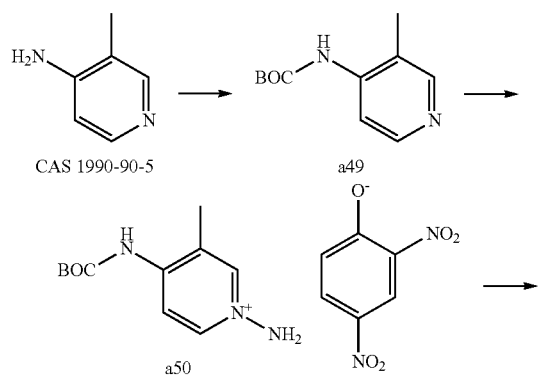

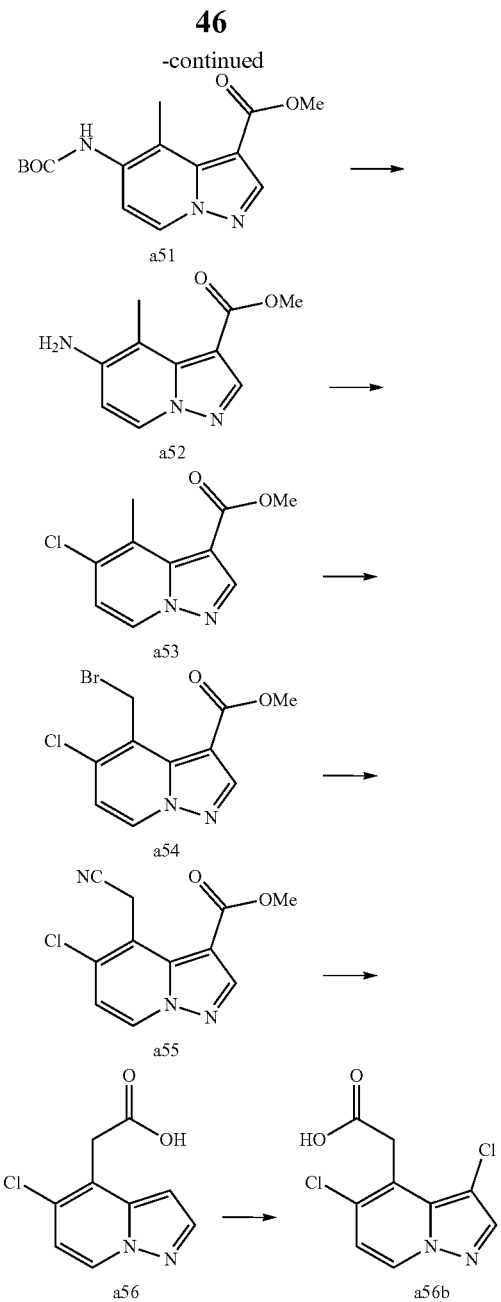

A.7.1. Synthesis of tert-butyl N-(3-methyl-4-pyridyl) a49

To a solution of 3-methylpyridin-4-amine (10 g, 92.6 mmol) in THF (100 mL) was added TEA (14 g, 138 mmol) and DMAP (1.12 g, 9.25 mmol) followed by addition of (Boc)$_2$O (22.2 g, 101 mmol) at 0° C. The reaction mixture was stirred at rt for 16 h. Progress of the reaction was monitored by TLC and LCMS. After completion, the reaction mixture was concentrated under vacuum. The residue was diluted with water (50 mL) and extracted with DCM (3×70 mL). The organic layer was separated, dried over anhydrous Na$_2$SO$_4$ and concentrated under vacuum to afford 16.2 g of tert-butyl N-(3-methylpyridin-4-yl)carbamate a49, which was used in next step without further purification.

LCMS (ES$^+$): 209 (M+H)$^+$, 96% purity.

¹H NMR (400 MHz, DMSO-d$_6$) δ 8.76 (s, 1H), 8.22-8.26 (m, 2H), 7.62-7.66 (m, 1H), 2.18 (s, 3H), 1.48 (s, 9H).

A.7.2. Synthesis of tert-butyl N-(1-amino-3-methyl-4-pyridyl)carbamate; 2,4-dinitrophenolate a50

To a solution of tert-butyl N-(3-methylpyridin-4-yl)carbamate a49 (10 g, 48 mmol) in 2-methyltetrahydrofuran (60 mL) was added O-(2,4-dinitrophenyl)hydroxylamine (9.51 g, 48 mmol). The reaction mixture was heated at 40° C. for 5 h, then stirred at rt for 16 h. Progress of the reaction was monitored by TLC. After completion, the reaction mixture was concentrated under vacuum. The crude obtained was purified by triturating with Et$_2$O (20 mL) and dried under vacuum to afford 18.6 g of tert-butyl N-(1-amino-3-methyl-4-pyridyl)carbamate; 2,4-dinitrophenolate a50 as a brown solid.

Yield: 95% (2 steps).

¹H NMR (400 MHz, DMSO-d$_6$) δ 9.71 (s, 1H), 8.59 (d, J=3.4 Hz, 1H), 8.47-8.54 (m, 2H), 8.34 (d, J=7.3 Hz, 1H), 7.75-7.81 (m, 3H), 6.32 (d, J=9.8 Hz, 1H), 2.30 (s, 3H), 1.52 (s, 9H).

A.7.3. Synthesis of methyl 5-(tert-butoxycarbonylamino)-4-methyl-pyrazolo[1,5-a]pyridine-3-carboxylate a51

To a solution of tert-butyl N-(1-amino-3-methyl-4-pyridyl)carbamate; 2,4-dinitrophenolate a50 (9 g, 22.1 mmol) and methyl prop-2-ynoate (3.72 g, 44.3 mmol) in DMF (50 mL) was added K$_2$CO$_3$ (7.64 g, 55.4 mmol) and the reaction mixture was stirred at rt for 16 h. Progress of the reaction was monitored by TLC. After completion, the reaction mixture was poured onto ice water (100 mL) and extracted with EtOAc (3×50 mL). The organic layer was separated, dried over anhydrous Na$_2$SO$_4$ and concentrated under vacuum. The crude obtained was purified by column chromatography using from 0 to 15% EtOAc in hexanes as eluent to afford 2.08 g of methyl 5-((tert-butoxycarbonyl)amino)-4-methylpyrazolo[1,5-a]pyridine-3-carboxylate a51 as a light yellow solid.

Yield: 31%.

¹H NMR (400 MHz, DMSO-d$_6$) δ 9.11 (s, 1H), 8.61 (d, J=7.3 Hz, 1H), 8.37 (s, 1H), 7.20-7.28 (m, 1H), 3.77 (s, 3H), 2.57 (s, 3H), 1.49 (s, 9H).

A.7.4. Synthesis of methyl 5-amino-4-methyl-pyrazolo[1,5-a]pyridine-3-carboxylate a52

To a solution of methyl 5-((tert-butoxycarbonyl)amino)-4-methylpyrazolo[1,5-a]pyridine-3-carboxylate a51 (4 g, 13.1 mmol) in DCM (20 mL) was added TFA (15 mL) at 0° C. The reaction mixture was stirred at 0° C. for 10 min, then at rt for 16 h. Progress of the reaction was monitored by TLC and LCMS. After completion, the reaction mixture was concentrated under vacuum. The residue was diluted with water (30 mL), basified with an aqueous saturated solution of NaHCO$_3$ (20 mL) and extracted with DCM (3×50 mL). The organic layer was separated, dried over anhydrous Na$_2$SO$_4$ and concentrated under vacuum. The crude obtained was purified by column chromatography using from 0 to 30% EtOAc in hexanes as eluent to afford 2.08 g of methyl 5-amino-4-methylpyrazolo[1,5-a]pyridine-3-carboxylate a52 as a light yellow solid.

Yield: 77%.

LCMS (ES⁺): 206 (M+H)⁺, 86% purity.

¹H NMR (400 MHz, DMSO-d$_6$) δ 8.31 (d, J=7.3 Hz, 1H), 8.13 (s, 1H), 6.55-6.64 (m, 1H), 5.94 (s, 2H), 3.71 (s, 3H), 2.48 (s, 3H).

A.7.5. Synthesis of methyl 5-chloro-4-methyl-pyrazolo[1,5-a]pyridine-3-carboxylate a53

To a solution of methyl 5-amino-4-methylpyrazolo[1,5-a]pyridine-3-carboxylate a52 (1.8 g, 8.78 mmol) in concentrated HCl (15 mL) was added at 0° C. a solution of CuCl (2.17 g, 21.9 mmol) in concentrated HCl (10 mL). The reaction mixture was stirred at 0° C. for 10 min, then a solution of NaNO$_2$ (0.78 g, 11.4 mmol) in water (25 mL) was added. The reaction mixture was heated at 80° C. for 3 h. Progress of the reaction was monitored by TLC and LCMS. After completion, the reaction mixture was quenched with a 2N aqueous solution of NaOH (up to pH 5) and extracted with EtOAc (3×30 mL). The organic layer was separated, dried over anhydrous Na$_2$SO$_4$ and concentrated under vacuum. The crude obtained was purified by column chromatography using 0 to 8% EtOAc in hexanes to afford 1.36 g of methyl 5-chloro-4-methylpyrazolo[1,5-a]pyridine-3-carboxylate a53 as a light yellow solid.

Yield: 69%.

LCMS (ES⁺): 225 (M+H)⁺, 71% purity.

¹H NMR (400 MHz, DMSO-d$_6$) δ 8.74 (d, J=7.3 Hz, 1H), 8.48 (s, 1H), 7.20-7.29 (m, 1H), 3.80 (s, 3H), 2.81 (s, 3H).

A.7.6. Synthesis of methyl 4-(bromomethyl)-5-chloro-pyrazolo[1,5-a]pyridine-3-carboxylate a54

To a solution of methyl 5-chloro-4-methylpyrazolo[1,5-a]pyridine-3-carboxylate a53 (0.50 g, 2.23 mmol) in CCl$_4$ (15 mL) was added NBS (0.43 g, 2.45 mmol) followed by addition of Bz$_2$O$_2$ (0.05 g, 0.22 mmol). The reaction mixture was heated at 70° C. for 8 h. Progress of the reaction was monitored by TLC and LCMS. After completion, the reaction mixture was concentrated under vacuum. The crude obtained was purified by column chromatography using 0 to 7% EtOAc in hexanes as eluent to afford 0.62 g of methyl 4-(bromomethyl)-5-chloropyrazolo[1,5-a]pyridine-3-carboxylate a54 as off-white solid.

Yield: 92%.

LCMS (ES⁺): 303 (M+H)⁺, 89% purity.

¹H NMR (400 MHz, DMSO-d$_6$) δ 8.91-8.97 (m, 1H), 8.60 (s, 1H), 7.34 (d, J=7.3 Hz, 1H), 5.55 (brs, 2H), 3.84 (s, 3H).

A.7.7. Synthesis of methyl 5-chloro-4-(cyanomethyl)pyrazolo[1,5-a]pyridine-3-carboxylate a55

To a solution of methyl 4-(bromomethyl)-5-chloropyrazolo[1,5-a]pyridine-3-carboxylate a54 (0.62 g, 2.04 mmol) in CH$_3$CN (10 mL) were added TMSCN (0.30 g, 3.06 mmol) and TBAF (3.00 mL, 3.06 mmol). The reaction mixture was stirred at rt for 1 h. Progress of the reaction was monitored by TLC and LCMS. After completion, the reaction mixture was concentrated under vacuum. The crude obtained was purified by column chromatography using 0 to 6% EtOAc in hexanes as eluent to afford 0.49 g of methyl 5-chloro-4-(cyanomethyl)pyrazolo[1,5-a]pyridine-3-carboxylate a55 as a white solid.

Yield: 96%.

LCMS (ES⁺): 250 (M+H)⁺, 98% purity.

¹H NMR (400 MHz, DMSO-d$_6$) δ 8.95 (brs, 1H), 8.59 (s, 1H), 7.37 (d, J=7.3 Hz, 1H), 4.77 (s, 2H), 3.84 (s, 3H).

A.7.8. Synthesis of 2-(5-chloropyrazolo[1,5-a]pyridin-4-yl)acetic Acid a56

To a solution of methyl 5-chloro-4-(cyanomethyl)pyrazolo[1,5-a]pyridine-3-carboxylate a55 (0.49 g, 1.96 mmol) in water (8 mL) was added concentrated H$_2$SO$_4$ (8 mL) and the reaction mixture was heated at 100° C. for 16 h. Progress of the reaction was monitored by TLC and LCMS. After completion, the reaction mixture was poured onto ice water (15 mL), basified with a 2N aqueous solution of NaOH (15 mL) and extracted with a solution of 10% MeOH in DCM (3×50 mL). The organic layer was separated, dried over anhydrous Na$_2$SO$_4$ and concentrated under vacuum. The crude obtained was purified by triturating with a solution of 10% Et$_2$O in hexanes (3×20 mL) to afford 0.37 g of 2-(5-chloropyrazolo[1,5-a]pyridin-4-yl) acetic acid a56 as off-white solid.

Yield: 90%.
LCMS (ES$^+$): 211 (M+H)$^+$, 96.5% purity.
$^1$H NMR (400 MHz, DMSO-d$_6$) δ 12.55-12.84 (m, 1H), 8.62-8.71 (m, 1H), 8.03 (d, J=2.0 Hz, 1H), 6.96 (d, J=7.3 Hz, 1H), 6.76 (d, J=1.47 Hz, 1H), 3.93 (s, 2H).

A.7.9. Synthesis of 2-(3,5-dichloropyrazolo[1,5-a]pyridin-4-yl)acetic Acid a56b A mixture of 2-(5-chloropyrazolo[1,5-a]pyridin-4-yl) acetic acid a56 (230 mg, 1.09 mmol), trichloroisocyanuric acid (84 mg, 0.36 mmol) and zeolite Y, hydrogen (40 mg) in ACN (5 mL) was stirred at 80° C. for 18 h. The reaction mixture was filtered and the filtrate was concentrated under vacuum. The crude residue was purified by reverse phase chromatography (Acidic mode, prep LCMS) to afford 45 mg of 2-(3,5-dichloropyrazolo[1,5-a]pyridin-4-yl)acetic acid a56b.

Yield: 17%.
LCMS (ES$^+$): 245.0/247.0/249.0 (M+H)$^+$.

A.8. Synthesis of 2-(6-bromo-5-chloro-pyrazolo[1,5-a]pyridin-4-yl)acetic Acid a61

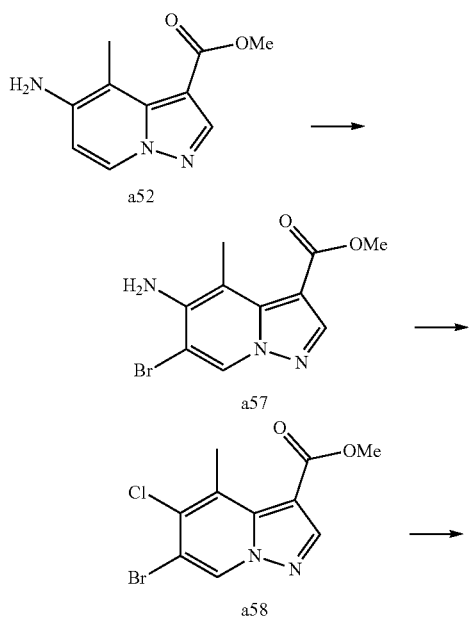

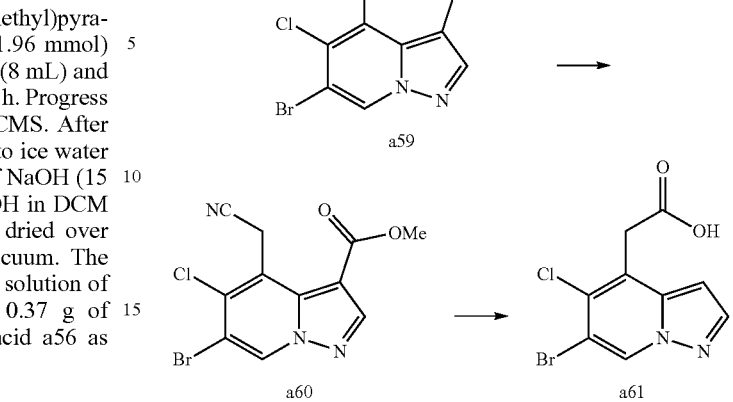

A.8.1. Synthesis of methyl 5-amino-6-bromo-4-methyl-pyrazolo[1,5-a]pyridine-3-carboxylate a57

To a solution of methyl 5-amino-4-methyl-pyrazolo[1,5-a]pyridine-3-carboxylate a52 (2.7 g, 13.2 mmol) in DCM (30 mL) was added NBS (2.34 g, 13.2 mmol) at 0° C. The reaction mixture was stirred at 0° C. for 2 h, then at rt for 16 h. Progress of the reaction was monitored by TLC and LCMS. After completion, the reaction mixture was concentrated under vacuum. The residue was diluted with water (30 mL) and extracted with EtOAc (3×50 mL). The organic layer was dried over anhydrous Na$_2$SO$_4$ and concentrated under vacuum. The crude residue was purified by column chromatography using 15% EtOAc in hexanes as eluent to afford 3 g of methyl 5-amino-6-bromo-4-methylpyrazolo[1,5-a]pyridine-3-carboxylate a57 as an off-white solid.

Yield: 80%.
LCMS (ES$^+$): 284.0 (M+H)$^+$, 97% purity.
$^1$H NMR (400 MHz, DMSO-d$_6$) δ 8.92 (s, 1H), 8.19 (s, 1H), 5.95 (s, 2H), 3.71 (s, 3H), 2.59 (s, 3H).

A.8.2. Synthesis of methyl 6-bromo-5-chloro-4-methyl-pyrazolo[1,5-a]pyridine-3-carboxylate a58

To a solution of methyl 5-amino-6-bromo-4-methylpyrazolo[1,5-a]pyridine-3-carboxylate a57 (2.80 g, 9.86 mmol) in concentrated HCl (15 mL) was added NaNO$_2$ (0.74 g, 10.8 mmol) at 0° C. The reaction mixture was stirred at 0° C. for 30 min., then a solution of CuCl (1.17 g, 11.8 mmol) in water (5 mL) was added dropwise. The reaction mixture was stirred at rt for 3 h. Progress of the reaction was monitored by TLC and LCMS. After completion, the reaction mixture was quenched with ice water (20 mL) and extracted with EtOAc (3×50 mL). The organic layer was dried over anhydrous Na$_2$SO$_4$ and concentrated under vacuum. The crude residue was purified by column chromatography using 15% EtOAc in hexanes as eluent to afford 2.4 g of methyl 6-bromo-5-chloro-4-methylpyrazolo[1,5-a]pyridine-3-carboxylate a58 as an off-white solid.

Yield: 80%.
$^1$H NMR (400 MHz, DMSO-d$_6$) δ 9.35 (s, 1H), 8.51 (s, 1H), 3.81 (s, 3H), 2.91 (s, 3H).

A.8.3. Synthesis of methyl 6-bromo-4-(bromomethyl)-5-chloro-pyrazolo[1,5-a]pyridine-3-carboxylate a59

To a solution of methyl 6-bromo-5-chloro-4-methylpyrazolo[1,5-a]pyridine-3-carboxylate a58 (2.35 g, 7.74 mmol)

in CCl₄ (30 mL) was added NBS (1.52 g, 8.52 mmol) followed by addition of AIBN (0.13 g, 0.77 mmol). The reaction mixture was heated at 60° C. for 10 h. Progress of the reaction was monitored by TLC and LCMS. After completion, the reaction mixture was concentrated under vacuum. The residue was diluted with water (20 mL) and extracted with EtOAc (3×30 mL). The organic layer was dried over anhydrous Na₂SO₄ and concentrated under vacuum to afford 2.2 g of methyl 6-bromo-4-(bromomethyl)-5-chloropyrazolo[1,5-a]pyridine-3-carboxylate a59 as an off-white solid, which was used in next step without any further purification.

Yield (crude): 74%.

LCMS (ES⁺): 382 (M+H)⁺, 80% purity.

¹H NMR (400 MHz, DMSO-d₆) δ 9.54 (s, 1H), 8.63 (s, 1H), 3.85 (s, 3H), 2.56 (s, 2H).

A.8.4. Synthesis of methyl 6-bromo-5-chloro-4-(cyanomethyl)pyrazolo[1,5-a]pyridine-3-carboxylate a60

To a solution of methyl 6-bromo-4-(bromomethyl)-5-chloropyrazolo[1,5-a]pyridine-3-carboxylate a59 (2.10 g, 5.49 mmol) in CH₃CN (20 mL) was added a 1N solution of TBAF in THF (1.73 g, 5.49 mmol), followed by addition of TMSCN (0.55 g, 5.49 mmol). The reaction mixture was stirred at rt for 3 h. Progress of the reaction was monitored by TLC and LCMS. After completion, the reaction mixture was quenched with an aqueous saturated solution of NaHCO₃ (10 mL) and extracted with DCM (3×20 mL). The organic layer was dried over anhydrous Na₂SO₄ and concentrated under vacuum to afford 1.45 g of methyl 6-bromo-5-chloro-4-(cyanomethyl)pyrazolo[1,5-a]pyridine-3-carboxylate a60 as an off-white solid, which was used in next step without any further purification.

Yield(crude): 80%.

LCMS (ES⁺): 328 (M+H)⁺, 44% purity.

A.8.5. Synthesis of 2-(6-bromo-5-chloro-pyrazolo[1,5-a]pyridin-4-yl)acetic Acid a61

A stirred solution of methyl 6-bromo-5-chloro-4-(cyanomethyl)pyrazolo[1,5-a]pyridine-3-carboxylate a60 (1.10 g, 3.35 mmol) in concentrated H₂SO₄ (12 mL) and water (4 mL) was heated at 110° C. for 16 h. Progress of the reaction was monitored by TLC and LCMS. After completion, the reaction mixture was quenched up to pH 5 with a 2N solution of NaOH and extracted with a solution of 10% MeOH in DCM (3×20 mL). The organic layer was dried over anhydrous Na₂SO₄ and concentrated under vacuum. The crude obtained was purified by column chromatography using from 0 to 6% MeOH in DCM as eluent to afford 0.41 g of 2-(6-bromo-5-chloropyrazolo[1,5-a]pyridin-4-yl) acetic acid a61 as an off-white solid.

Yield: 42%.

LCMS (ES⁺): 289 (M+H)⁺, 96% purity.

¹H NMR (400 MHz, DMSO-d₆) δ 12.84 (brs, 1H), 9.22 (s, 1H), 8.05 (d, J=2.45 Hz, 1H), 6.83 (d, J=1.96 Hz, 1H), 3.98 (s, 2H).

B. Synthesis of Intermediates of Formula (III)

B.1. Synthesis of (1R)-1-fluoro-2-[(1S)-1-methyl-1,2,3,4-tetrahydroisoguinolin-5-yl]propan-2-ol hydrochloride a24-(R,S) and (1S)-1-fluoro-2-[(1S)-1-methyl-1,2,3,4-tetrahydroisoguinolin-5-yl]propan-2-ol hydrochloride a24-(S,S)

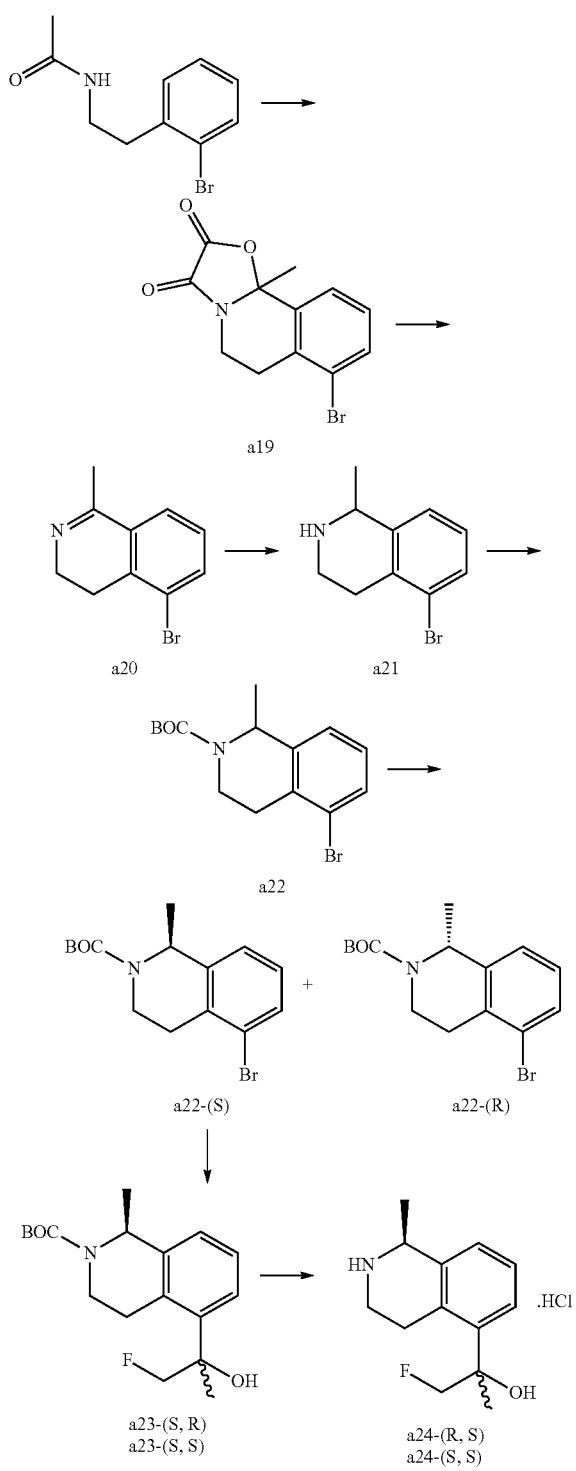

2.1.1. Synthesis of 7-bromo-10b-methyl-6,10b-dihydro-5H-[1,3]oxazolo[2,3-a]isoguinoline-2,3-dione a19

To a solution of N-[2-(2-bromophenyl)ethyl]acetamide (commercial, 106.5 g, 439.8 mmol) in DCM (1.5 L) was added dropwise at 0° C. oxalyl chloride (72 mL, 792.3 mmol). The mixture was stirred at 0° C. for 2 h, then allowed to warm to rt and stirred for 3 h. The reaction mixture was then cooled to 0° C. and ferric chloride (86 g, 530.2 mmol) was added in 2 portions. The reaction mixture was allowed to warm to rt, stirred overnight at rt, diluted with DCM (2.5 L) and then quenched at 0° C. with a 12M concentrated solution of ammonia (200 mL). The organic layer was dried over $Na_2SO_4$, filtered and concentrated under vacuum to yield 108 g of 7-bromo-10b-methyl-6,10b-dihydro-5H-[1,3]oxazolo[2,3-a]isoquinoline-2,3-dione a19 as a brown solid, which was used in next step without any further purification.

Yield (crude): 83%.
LCMS (ES$^+$): 296/298 (M+H)$^+$.

2.1.2. Synthesis of 5-bromo-1-methyl-3,4-dihydroisoquinoline a20

To a suspension of 7-bromo-10b-methyl-6,10b-dihydro-5H-[1,3]oxazolo[2,3-a]isoquinoline-2,3-dione a19 (108 g, 364.72 mmol) in MeOH (1.5 L) was added dropwise at rt sulfuric acid (75 mL). The reaction mixture was stirred overnight at 65° C., then quenched at 0° C. with a 15M concentrated solution of ammonia (300 mL). The mixture was concentrated under vacuum and water (300 mL) was added. The aqueous layer was extracted 6 times with DCM (1 L). The organic layer was dried over $MgSO_4$, filtered and concentrated under vacuum to afford 86.44 g of 5-bromo-1-methyl-3,4-dihydroisoquinoline a20 as a brown solid, which was used in next step without any further purification.

Yield (crude): 95%.
HPLC (Basic Mode): RT 4.75 min, 87% purity.

2.1.3. Synthesis of 5-bromo-1-methyl-1,2,3,4-tetrahydroisoquinoline a21

To a solution of 5-bromo-1-methyl-3,4-dihydroisoquinoline a20 (86.44 g, 347.1 mmol) in EtOH (2 L) was added at 0° C. sodium borohydride (13.2 g, 349 mmol) portionwise (13*1 g). The mixture was stirred at 0° C. for 2 h, then a 5N aqueous solution of HCl solution (250 mL) was added at 0° C. The reaction mixture was stirred overnight at rt, then EtOH was concentrated under vacuum. DCM (1 L) was added and the mixture was quenched at 0° C. with a 6M concentrated solution of ammonia (400 mL). The organic layer was extracted twice with DCM (500 mL), dried over $MgSO_4$, filtered and concentrated under vacuum to afford 83 g of 5-bromo-1-methyl-1,2,3,4-tetrahydroisoquinoline a21 as a brown solid, which was used in next step without any further purification.

Yield (crude): 85%.
HPLC (Basic Mode): RT 4.53 min, 80% purity.

2.1.4. Synthesis of tert-butyl 5-bromo-1-methyl-3,4-dihydroisoquinoline-2(1H)-carboxylate a22, a22-S and a22-R To a solution of 5-bromo-1-methyl-1,2,3,4-tetrahydroisoquinoline a21 (78 g, 276 mmol) in DCM (1 L) was added TEA (160 mL, 1136 mmol) at 0° C. A solution of di-tert-butyl dicarbonate (65 g, 294.8 mmol) in DCM (250 mL) was then added dropwise at 0° C. The reaction mixture was stirred overnight at rt and quenched with water (100 mL). The organic layer was dried over $MgSO_4$, filtered and concentrated under vacuum. The residue was triturated twice in a mixture of MeOH/n-hexanes (1:2, 450 mL) to yield 63 g of tert-butyl 5-bromo-1-methyl-3,4-dihydroisoquinoline-2(1H)-carboxylate a22 (Yield: 70%, HPLC (Basic Mode): RT 6.59 min, 98% purity) as a white solid.

Chiral separation (SFC, Whelko 01(R,R), 50*227 mm, 360 mL/min, 220 nm, 25° C., eluent: from 20% iPrOH) of racemate tert-butyl 5-bromo-1-methyl-3,4-dihydroisoquinoline-2(1H)-carboxylate a22 afforded:

25.1 g of tert-butyl (1S)-5-bromo-1-methyl-3,4-dihydroisoquinoline-2(1H)-carboxylate a22-(S) as a solid.
Yield: 40%.
HPLC (Basic Mode): RT 6.59 min, 91% purity.
Chiral analysis (LC, Whelko-01 (R,R), 250*4.6 mm, 1 mL/min, 220 nm, 30° C., eluent: iPrOH/n-heptane/DEA 50/50/0.1) RT 4.86 min, 97.7% ee.

29.3 g of tert-butyl (1R)-5-bromo-1-methyl-3,4-dihydroisoquinoline-2(1H)-carboxylate a22-(R) as a solid.
Yield: 46%.
HPLC (Basic Mode): RT 6.59 min, 98% purity.
Chiral analysis (LC, Whelko-01 (R,R), 250*4.6 mm, 1 mL/min, 220 nm, 30° C., eluent: iPrOH/n-heptane/DEA 50/50/0.1) RT 5.62 min, 92.4% ee.

2.1.5. Synthesis of tert-butyl (1S)-5-[(1R)-2-fluoro-1-hydroxy-1-methyl-ethyl]-1-methyl-3,4-dihydro-1H-isoquinoline-2-carboxylate a23-(S,R) and tert-butyl (1S)-5-[(1S)-2-fluoro-1-hydroxy-1-methyl-ethyl]-1-methyl-3,4-dihydro-1H-isoquinoline-2-carboxylate a23-(S,S)

tert-Butyl (1S)-5-bromo-1-methyl-3,4-dihydro-1H-isoquinoline-2-carboxylate a22-(S) (7 g, 21.45 mmol) was dissolved in dry tetrahydrofuran (107 mL) at −78° C. n-BuLi (26.8 mL, 32.93 mmol) was added dropwise and the mixture was stirred at −78° C. for 10 min. Fluoroacetone (4.78 mL, 64.2 mmol) was added and the mixture was stirred at rt for 1 h. The reaction mixture was quenched with a 1N aqueous solution of HCl (350 mL), then extracted thrice with dichloromethane. The organic layer was dried over $MgSO_4$, filtered and concentrated under vacuum. The residue was purified by reverse phase chromatography (basic mode, standard LC). Chiral separation (LC, chiralpak IC, 80*380 mm, 300 mL/min, 220 nm, 30° C., eluent: 10% iPrOH in heptane) afforded:

1.137 g of tert-butyl (1S)-5-[(1R)-2-fluoro-1-hydroxy-1-methyl-ethyl]-1-methyl-3,4-dihydro-1H-isoquinoline-2-carboxylate a23-(S,R) as a beige solid.
Yield: 20%
LCMS (ES$^+$): 268.0 (M-tBu+H)$^+$.
Chiral analysis (LC, Whelko-01 (R,R), 150*4.6 mm, 1.5 mL/min, 220 nm, 30° C., eluent: iPrOH/n-heptane/DEA 10/90/0.1): RT 2.37 min, 100% ee.

1.074 g of tert-butyl (1S)-5-[(1S)-2-fluoro-1-hydroxy-1-methyl-ethyl]-1-methyl-3,4-dihydro-1H-isoquinoline-2-carboxylate a23-(S,S) as a beige solid.
Yield: 19%
LCMS (ES$^+$): 268.0 (M-tBu+H)$^+$.
Chiral analysis (LC, Whelko-01 (R,R), 150*4.6 mm, 1.5 mL/min, 220 nm, 30° C., eluent: iPrOH/n-heptane/DEA 10/90/0.1): RT 2.72 min, 100% ee.

2.1.6. Synthesis of (1R)-1-fluoro-2-[(1S)-1-methyl-1,2,3,4-tetrahydroisoquinolin-5-yl]propan-2-ol hydrochloride a24-(R,S) and (1S)-1-fluoro-2-[(1S)-1-methyl-1,2,3,4-tetrahydroisoquinolin-5-yl]propan-2-ol hydrochloride a24-(S,S)

tert-Butyl (1S)-5-[(1R)-2-fluoro-1-hydroxy-1-methyl-ethyl]-1-methyl-3,4-dihydro-1H-isoquinoline-2-carboxylate a23-(S,R) (1.137 g, 3.516 mmol) was dissolved in dioxane (18 ml) at rt. A 4N solution of HCl in dioxane (8.8 mL, 35 mmol) was added. The mixture was stirred at rt overnight. The reaction mixture was concentrated under vacuum to yield 950 mg of (1R)-1-fluoro-2-[(1S)-1-methyl-1,2,3,4-tetrahydroisoquinolin-5-yl]propan-2-ol hydrochloride a24-(R,S) as a beige solid.
Yield(crude): quantitative.
LCMS (ES+): 224.0 (M+H)+.

(1S)-1-fluoro-2-[(1S)-1-methyl-1,2,3,4-tetrahydroisoquinolin-5-yl]propan-2-ol hydrochloride a24-(S,S)

Compound a24-(S,S) may be synthetized according to the same method using tert-butyl (1S)-5-[(1S)-2-fluoro-1-hydroxy-1-methyl-ethyl]-1-methyl-3,4-dihydro-1H-isoquinoline-2-carboxylate a23-(S,S) as starting material.
Yield(crude): quantitative.
LCMS (ES+): 224 (M+H)+.

B.2. Synthesis of (1R)-2,2-difluoro-1-[(1S)-1-methyl-1,2,3,4-tetrahydroisoquinolin-5-yl]ethanol hydrochloride a27-R,S and (1S)-2,2-difluoro-1-[(1S)-1-methyl-1,2,3,4-tetrahydroisoquinolin-5-yl]ethanol hydrochloride a27-S,S

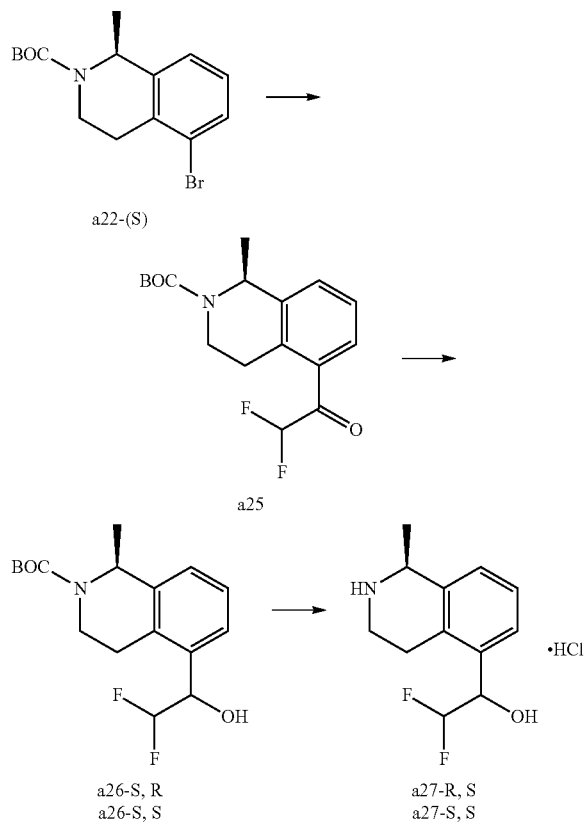

2.2.1. Synthesis of tert-butyl (1S)-5-(2,2-difluoro-acetyl)-1-methyl-3,4-dihydro-1H-isoquinoline-2-carboxylate a25

A solution of tert-butyl (1S)-5-bromo-1-methyl-3,4-dihydro-1H-isoquinoline-2-carboxylate a22-(S) (38 g, 116.5 mmol) in dry THF (0.2 M solution) and a commercial solution of n-BuLi in n-hexanes (1.6 M, 130 mmol, 1.1 equiv.) were pumped at respectively 2.25 ml/min and 0.375 ml/min and were mixed in a glass microchip cooled at −40° C. The mixed flow stream was pumped throught the reaction zone 1 of the microchip and was then combined with a solution of ethyl difluoroacetate (54 mL, 498 mmol, 4.3 equiv) in dry THF (2.4 M) pumped at 0.75 mL/min. The resulting stream was then passed through the reaction zone 2 of the microchip at −40° C. Finally, the global flow stream exiting the reactor was collected and quenched at rt with an aqueous saturated solution of ammonium chloride (350 mL). When all the feed solutions were consumed, a 2 layer reaction mixture was obtained. The aqueous layer was separated from the organic layer, and then extracted twice with EtOAc (400 mL). The organic layer was washed with brine, dried over sodium sulfate and concentrated under vacuum. Purification by normal phase column chromatography using from 10% of EtOAc in heptane as eluent afforded 22.7 g of tert-butyl (1S)-5-(2,2-difluoroacetyl)-1-methyl-3,4-dihydro-1H-isoquinoline-2-carboxylate a25 as a colorless oil.
Yield: 57%.
LCMS (ES+): 270.0 (M-tBu+H)+, 94.6% purity.

2.2.2. Synthesis of tert-butyl (1S)-5-[(1R)-2,2-difluoro-1-hydroxy-ethyl]-1-methyl-3,4-dihydro-1H-isoquinoline-2-carboxylate a26-S,R and tert-butyl (1S)-5-[(1S)-2,2-difluoro-1-hydroxy-ethyl]-1-methyl-3,4-dihydro-1H-isoquinoline-2-carboxylate a26-S,S To a solution of tert-butyl (1S)-5-(2,2-difluoroacetyl)-1-methyl-3,4-dihydro-1H-isoquinoline-2-carboxylate a25 (90.6 g, 278 mmol) in DCM (1 L) was added lithium borohydride (13 g, 596 mmol) at 0° C. The mixture was stirred at 0° C. and then allowed to warm up slowly to rt for 2 h. The mixture was quenched slowly with water (100 mL) and a 0.5N aqueous solution of HCl (1.8 L). The mixture was stirred overnight at rt, then the organic layer was separated, dried over MgSO4, filtered and concentrated under vacuum to yield 91.3 g of racemic tert-butyl (1S)-5-(2,2-difluoro-1-hydroxy-ethyl)-1-methyl-3,4-dihydro-1H-isoquinoline-2-carboxylate a26 as a white solid.
Chiral Separation (SFC, Lux-Cell-2, 50*257 mm, 360 mL/min, 220 nm, 30° C., eluent: 7% iPrOH) of 103 g of racemate material a26 afforded:
50 g of tert-butyl (1S)-5-[(1R)-2,2-difluoro-1-hydroxy-ethyl]-1-methyl-3,4-dihydro-1H-isoquinoline-2-carboxylate a26-S,R.
Yield: 48%
LCMS (ES+): 272.0 (M-tBu+H)+
Chiral analysis (LC, OD, 150*4.6 mm, 1.5 mL/min, 220 nm, 30° C., eluent: EtOH/n-heptane/DEA 10/90/0.1): RT 2.11 min, 99.6% ee.
52.7 g of tert-butyl (1S)-5-[(1S)-2,2-difluoro-1-hydroxy-ethyl]-1-methyl-3,4-dihydro-1H-isoquinoline-2-carboxylate a26-S,S.
Yield: 51%
LCMS (ES+): 272.0 (M-tBu+H)+

2.2.3. Synthesis of (1R)-2,2-difluoro-1-[(1S)-1-methyl-1,2,3,4-tetrahydroisoquinolin-5-yl]ethanol hydrochloride a27-R,S and (1S)-2,2-difluoro-1-[(1S)-1-methyl-1,2,3,4-tetrahydroisoquinolin-5-yl]ethanol hydrochloride a27-S,S To a solution of tert-butyl (1S)-5-[(1R)-2,2-difluoro-1-hydroxy-ethyl]-1-methyl-3,4-dihydro-1H-isoquinoline-2-carboxylate a26-S,R (50 g, 152.7 mmol) in 1,4-dioxane (500 mL) was added dropwise a 4N solution of HCl in dioxane (100 mL, 400 mmol) at 0° C. The reaction mixture was allowed to stir overnight at rt, then concentrated under vacuum. The resulting precipitate was filtered off and dried under vacuum to afford 34 g of (1R)-2,2-difluoro-1-[(1S)-1-methyl-1,2,3,4-tetrahydroisoquinolin-5-yl]ethanol hydrochloride a27-R,S, a was directly used in the next reaction without further purification.

Yield (crude): quantitative.
LCMS (ES+): 228.0 (M+H)+

(1S)-2,2-difluoro-1-[(1S)-1-methyl-1,2,3,4-tetrahydroisoquinolin-5-yl]ethanol hydrochloride a27-S,S Compound a27-S,S may be synthetized according to the same method using tert-butyl (1S)-5-[(1S)-2,2-difluoro-1-hydroxy-ethyl]-1-methyl-3,4-dihydro-1H-isoquinoline-2-carboxylate a26-S,S as starting material.
Yield(crude): quantitative.
LCMS (ES+): 228.0 (M+H)+

B.3. Synthesis of 1,1-difluoro-2-[(1S)-1-methyl-1,2,3,4-tetrahydroisoquinolin-5-yl]propan-2-ol hydrochloride isomers a29-A and a29-B

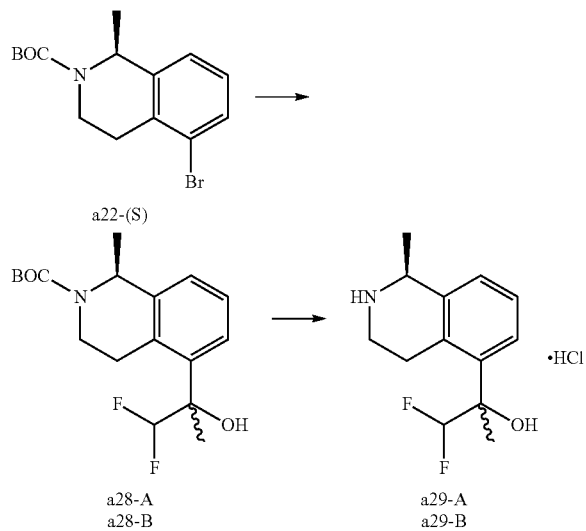

a22-(S)

a28-A
a28-B a29-A
a29-B

2.3.1. Synthesis of tert-butyl (1S)-5-(2,2-difluoro-1-hydroxy-1-methyl-ethyl)-1-methyl-3,4-dihydro-1H-isoquinoline-2-carboxylate isomers a28-A and a28-B tert-Butyl (1S)-5-bromo-1-methyl-3,4-dihydro-1H-isoquinoline-2-carboxylate a22-(S) (1 g, 3.066 mmol) was dissolved in THF (20 mL) at −78° C. nBuLi (2.7 M, 2.3 mL, 6.1 mmol) was added dropwise followed by the 1,1-difluoroacetone (766 µL, 9.2 mmol). The reaction mixture was stirred at rt for 1 h, then quenched with water and extracted twice with DCM. The organic layer was dried over MgSO4 and concentrated under vacuum. The residue was purified by reverse phase chromatography (Basic mode, standard LC) to yield 286 mg of racemate tert-butyl (1S)-5-(2,2-difluoro-1-hydroxy-1-methyl-ethyl)-1-methyl-3,4-dihydro-1H-isoquinoline-2-carboxylate a28 (Yield: 27%, LCMS (ES+): 242 (M-tBu+H)+/286 (M+H)+).

Chiral separation (LC, Chiralpak IC, 76*380 mm, 200 mL/min, 220 nm, 30° C., eluent: 10% iPrOH in heptane) of 2.5 g of crude racemate a28 afforded:

1.6 g of tert-butyl (1S)-5-(2,2-difluoro-1-hydroxy-1-methyl-ethyl)-1-methyl-3,4-dihydro-1H-isoquinoline-2-carboxylate isomer A a28-A.

Chiral analysis (LC, IC, 150*4.6 mm, 1.5 mL/min, 220 nm, 30° C., eluent: iPrOH/n-heptane/DEA 10/90/0.1): RT 2.83 min, 100% ee.

$^1$H NMR (400 MHz, CDCl$_3$) δ 7.21 (d, J=8.0 Hz, 1H), 7.12 (td, J=7.7, 1.5 Hz, 1H), 7.05 (dd, J=7.5, 2.4 Hz, 1H), 5.91 (t, J=55.3 Hz, 1H), 5.03 (d, J=38.5 Hz, 1H), 3.81-3.29 (m, 2H), 3.19 (s, 2H), 2.20 (s, 1H), 1.67 (d, J=1.7 Hz, 3H), 1.42 (d, J=2.0 Hz, 9H), 1.36 (d, J=6.8 Hz, 3H).

900 mg of tert-butyl (1S)-5-(2,2-difluoro-1-hydroxy-1-methyl-ethyl)-1-methyl-3,4-dihydro-1H-isoquinoline-2-carboxylate isomer B a28-B Chiral analysis (LC, IC, 150*4.6 mm, 1.5 mL/min, 220 nm, 30° C., eluent: iPrOH/n-heptane/DEA 10/90/0.1): RT 4.97 min, 100% ee.

$^1$H NMR (400 MHz, CDCl$_3$) δ 7.19 (s, 2H), 7.12 (t, J=7.7 Hz, 1H), 7.05 (d, J=7.5 Hz, 1H), 5.94 (d, J=55.5 Hz, 1H), 5.05 (d, J=49.1 Hz, 1H), 3.68 (d, J=67.1 Hz, 1H), 3.47-3.17 (m, 2H), 3.07 (s, 1H), 2.22 (s, 1H), 1.65 (d, J=1.7 Hz, 3H), 1.42 (s, 9H), 1.37 (d, J=6.8 Hz, 3H).

2.3.2. Synthesis of 1,1-difluoro-2-[(1S)-1-methyl-1,2,3,4-tetrahydroisoquinolin-5-yl]propan-2-ol hydrochloride isomers a29-A and a29-B To a solution of tert-butyl(1S)-5-[(2,2-difluoro-1-hydroxy-1-methyl-ethyl]-1-methyl-3,4-dihydro-1H-isoquinoline-2-carboxylate isomer A a28-A (948 mg, 2.78 mmol) in 1,4-dioxane (15 mL) was added dropwise a 4N solution of HCl in dioxane (7 mL, 28 mmol) at 0° C. The reaction mixture was stirred at rt for 36 h, then concentrated under vacuum to yield 760 mg of 1,1-difluoro-2-[(1S)-1-methyl-1,2,3,4-tetrahydroisoquinolin-5-yl]propan-2-ol hydrochloride isomer A a29-A as a white solid.

Yield (crude): quantitative.
LCMS (ES+): 242.0 (M+H)+.

1,1-difluoro-2-[(1S)-1-methyl-1,2,3,4-tetrahydroisoquinolin-5-yl]propan-2-ol hydrochloride isomer B a29-B Compound a29-B may be synthetized according to the same method using tert-Butyl(1S)-5-[(2,2-difluoro-1-hydroxy-1-methyl-ethyl]-1-methyl-3,4-dihydro-1H-isoquinoline-2-carboxylate isomer B a28-B as starting material.

Yield (crude): quantitative.
LCMS (ES+): 242.0 (M+H)+.

B.4. Synthesis of 1,3-difluoro-2-[(1S)-1-methyl-1,2,3,4-tetrahydroisoquinolin-5-yl]propan-2-ol hydrochloride a63

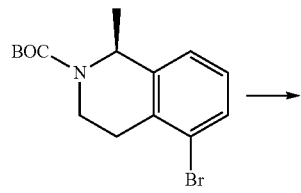

a22-(S)

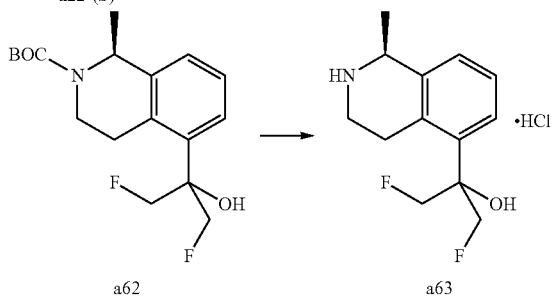

a62         a63

2.4.1. Synthesis of tert-butyl (1S)-5-[2-fluoro-1-(fluoromethyl)-1-hydroxy-ethyl]-1-methyl-3,4-dihydro-1H-isoquinoline-2-carboxylate a62

Tert-butyl (1S)-5-bromo-1-methyl-3,4-dihydro-1H-isoquinoline-2-carboxylate a22-(S) (2 g, 6.131 mmol) was dissolved in dry tetrahydrofuran (30 mL) at −78° C. N-Butyllithium (7.66 mL, 12.3 mmol) was added dropwise and the mixture was stirred at −78° C. for 10 min. Difluoroacetone (1.35 mL, 18.4 mmol) was added and the mixture was stirred at rt for 1 h. The reaction mixture was quenched with a 1N aqueous solution of HCl (50 mL), then extracted thrice with dichloromethane. The organic layer was dried over MgSO₄, filtered and concentrated under vacuum. The residue was purified by reverse phase chromatography (basic mode, standard LC) to yield 983 mg of tert-butyl (1S)-5-[2-fluoro-1-(fluoromethyl)-1-hydroxy-ethyl]-1-methyl-3,4-dihydro-1H-isoquinoline-2-carboxylate a62 as a yellow oil.
Yield: 47%.
LCMS (ES⁺): 286.0 (M-tBu+H)⁺

EXAMPLES

C. Synthesis of Compounds of Formula (I)

C.1. Method A. Synthesis of 2-(chloro-1H-indazol-4-yl)-1-[(1S)-5-[2-fluoro-1-hydroxy-1-methyl-ethyl]-1-methyl-3,4-dihydro-1H-isoquinolin-2-yl]ethanone a30-(S,R)

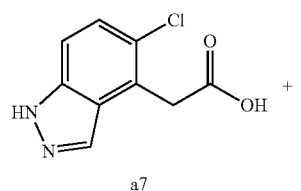

a7    +

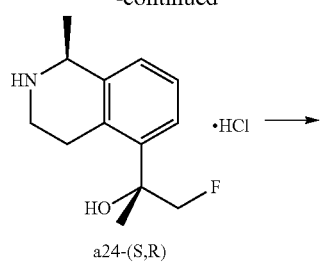

a24-(S,R)

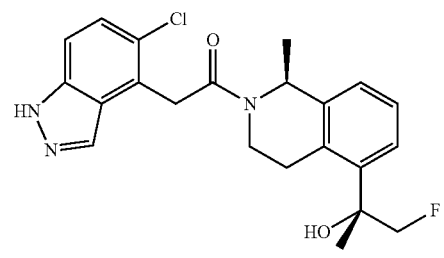

a30-(S,R)

(1R)-1-fluoro-2-[(1S)-1-methyl-1,2,3,4-tetrahydroisoquinolin-5-yl]propan-2-ol hydrochloride a24-(R,S) (100 mg, 0.38 mmol) and 2-(5-chloro-1H-indazol-4-yl)acetic acid a7 (81 mg, 0.38 mmol) were dissolved in ACN (4 mL) at rt, then 1-(3-dimethylaminopropyl))-3-ethylcarbodiimide hydrochloride (98 mg, 0.50 mmol) and 1-hydroxybenzotriazole hydrate (18 mg, 0.12 mmol) were added. The reaction mixture was stirred at rt for 15 min, then cooled to 0° C. before 4-methylmorpholine (0.13 mL, 0.12 mmol) was added. The mixture was stirred at rt overnight, then concentrated under vacuum. The residue was quenched with water and extracted twice with EtOAc. The organic layer was successively washed with an aqueous saturated solution of NaHCO₃, a 1N aqueous solution of HCl and water, then dried over MgSO₄ and concentrated under vacuum to yield 75 mg of 2-(chloro-1H-indazol-4-yl)-1-[(1S)-5-[(1R)-2-fluoro-1-hydroxy-1-methyl-ethyl]-1-methyl-3,4-dihydro-1H-isoquinolin-2-yl]ethanone a30-(S,R) as a colorless oil.

Yield (crude): 47%.
LCMS (ES⁺): 416.0/418.0 (M+H)⁺.

The following compounds may be synthesized according a method analogous to Method A. When commercially available, starting material are identified by their CAS Register Numbers.

| No | Acids II | Amines III | Conditions, Time | Purification conditions | Yield (%) | |
|---|---|---|---|---|---|---|
| a30-(S,S) | a7 | a24-(S,S) | rt, overnight | — | 48 | (crude) |
| a31 | a7 | a27-R,S | rt, overnight | — | 38 | (crude) |
| a32 | a7 | a27-S,S | rt, overnight | — | 45 | (crude) |
| a33-A | a7 | a29-A | rt, overnight | — | 100 | (crude) |
| a33-B | a7 | a29-B | rt, overnight | — | 100 | (crude) |
| a34 | a10 | a27-R,S | rt, overnight | — | 44 | |
| a35 | a10 | a27-S,S | rt, overnight | — | 47 | |
| a36 | a10/a11 | a27-R,S | rt, overnight | Basic RP-LCMS | 20 | |
| a37 | a10/a11 | a27-S,S | rt, overnight | Basic RP-LCMS | 24 | |
| 1 | a18 | a27-S,S | 2 h | Basic RP-LCMS, then NP using 0 to 20% MeOH in DCM | 3 | |
| 29 | a56b | a24-S,S | rt, overnight | Basic RP-LCMS | 58 | |
| a76 | a56 | a27-S,S | 3 h | Basic RP-LCMS | 55 | |

2-(3,5-dichloro-1H-indazol-4-yl)-1-[(1S)-5-[(1S)-2-fluoro-1-hydroxy-1-methyl-ethyl]-1-methyl-3,4-dihydro-1H-isoquinolin-2-yl]ethanone a30-(S,S)

LCMS (ES$^+$): 416.0/418.0 (M+H)$^+$, 89.5% purity 2-(5-chloro-1H-indazol-4-yl)-1-[(1S)-5-[(1R)-2,2-difluoro-1-hydroxy-ethyl]-1-methyl-3,4-dihydro-1H-isoquinolin-2-yl]ethanone a31

LCMS (ES$^+$): 420.0/422.0 (M+H)$^+$.

2-(5-chloro-1H-indazol-4-yl)-1-[(1S)-5-[(1S)-2,2-difluoro-1-hydroxy-ethyl]-1-methyl-3,4-dihydro-1H-isoquinolin-2-yl]ethanone a32

LCMS (ES$^+$): 420.0/422.0 (M+H)$^+$.

2-(5-chloro-1H-indazol-4-yl)-1-[(1S)-5-[2,2-difluoro-1-hydroxy-1-methyl-ethyl]-1-methyl-3,4-dihydro-1H-isoquinolin-2-yl]ethanone isomer A a33-A LCMS (ES$^+$): 434.0/436.0 (M+H)$^+$, 94% purity.

2-(5-chloro-1H-indazol-4-yl)-1-[(1S)-5-[2,2-difluoro-1-hydroxy-1-methyl-ethyl]-1-methyl-3,4-dihydro-1H-isoquinolin-2-yl]ethanone isomer B a33-B LCMS (ES$^+$): 434.0/436.0 (M+H)$^+$, 94% purity.

2-(5-chloro-2-methyl-indazol-4-yl)-1-[(1S)-5-[(1R)-2,2-difluoro-1-hydroxy-ethyl]-1-methyl-3,4-dihydro-1H-isoquinolin-2-yl]ethanone a34

LCMS (ES$^+$): 434.0/436.0 (M+H)$^+$.

2-(5-chloro-2-methyl-indazol-4-yl)-1-[(1S)-5-[(1S)-2,2-difluoro-1-hydroxy-ethyl]-1-methyl-3,4-dihydro-1H-isoquinolin-2-yl]ethanone a35

LCMS (ES$^+$): 434.0/436.0 (M+H)$^+$.

2-(5-chloro-1-methyl-indazol-4-yl)-1-[(1S)-5-[(1R)-2,2-difluoro-1-hydroxy-ethyl]-1-methyl-3,4-dihydro-1H-isoquinolin-2-yl]ethanone a36

LCMS (ES$^+$): 434.0/436.0 (M+H)$^+$.
$^1$H NMR (400 MHz, DMSO-d$_6$) δ 8.11 (d, J=7.0 Hz, 1H), 7.57 (dd, J=8.9, 2.5 Hz, 1H), 7.44-7.32 (m, 2H), 7.32-7.18 (m, 2H), 6.10 (d, J=4.7 Hz, 1H), 5.75 (s, 1H), 5.42 (dq, J=13.8, 6.7 Hz, 1H), 4.41-4.23 (m, 1H), 4.20 (d, J=12.8 Hz, 1H), 4.20-4.06 (m, 1H), 4.03 (s, 3H), 3.61 (ddd, J=14.0, 9.7, 4.9 Hz, 1H), 3.16-2.84 (m, 2H), 1.57 (d, J=6.6 Hz, 1H), 1.38 (d, J=6.8 Hz, 2H).

2-(5-chloro-1-methyl-indazol-4-yl)-1-[(1S)-5-[(1S)-2,2-difluoro-1-hydroxy-ethyl]-1-methyl-3,4-dihydro-1H-isoquinolin-2-yl]ethanone a37

LCMS (ES$^+$): 434.0/436.0 (M+H)$^+$.
$^1$H NMR (400 MHz, DMSO-d$_6$) δ 8.10 (s, 1H), 7.56 (dd, J=8.8, 2.3 Hz, 1H), 7.45-7.35 (m, 2H), 7.34-7.18 (m, 2H), 6.21-6.11 (m, OH), 6.12 (s, 1H), 6.04 (d, J=4.3 Hz, OH), 5.75 (s, 1H), 5.51-5.35 (m, 1H), 4.98 (s, 1H), 4.36-4.09 (m, 3H), 4.03 (s, 3H), 3.55 (ddd, J=14.1, 10.9, 4.0 Hz, 1H), 3.10-2.78 (m, 2H), 1.57 (d, J=6.7 Hz, 1H), 1.38 (d, J=6.7 Hz, 2H).

2-(3,5-dichloro-1,2-benzoxazol-4-yl)-1-[(1S)-5-[(1S)-2,2-difluoro-1-hydroxy-ethyl]-1-methyl-3,4-dihydro-1H-isoquinolin-2-yl]ethanone 1

LCMS (ES$^+$): 455.0/457.0/459.0 (M+H)$^+$, 98.9% purity.

2-(3,5-dichloropyrazolo[1,5-a]pyridin-4-yl)-1-[(1S)-5-[(1S)-2-fluoro-1-hydroxy-1-methyl-ethyl]-1-methyl-3,4-dihydro-1H-isoquinolin-2-yl]ethanone 29

LCMS (ES$^+$): 450.0/452.0/454.0 (M+H)+, 95.5% purity.
$^1$H NMR (400 MHz, DMSO-d$_6$) δ 8.65 (dd, J=7.4, 1.6 Hz, 1H), 8.14 (s, 1H), 7.36-7.10 (m, 3H), 7.04 (d, J=7.4 Hz, 1H), 5.53 5.29 (m, 2H), 4.69-4.16 (m, 4H), 4.10-3.65 (m, 2H), 3.58-3.40 (m, 1H), 1.72-1.30 (m, 6H).

2-(5-chloropyrazolo[1,5-a]pyridin-4-yl)-1-[(1S)-5-[(1S)-2,2-difluoro-1-hydroxy-ethyl]-1-methyl-3,4-dihydro-1H-isoquinolin-2-yl]ethanone a76

LCMS (ES⁺): 420/422 (M+H)⁺.

C.2. Method B. Synthesis of 2-(3,5-dichloro-1H-indazol-4-yl)-1-[(1S)-5-[(1R)-2-fluoro-1-hydroxy-1-methyl-ethyl]-1-methyl-3,4-dihydro-1H-isoquinolin-2-yl]ethanone 2

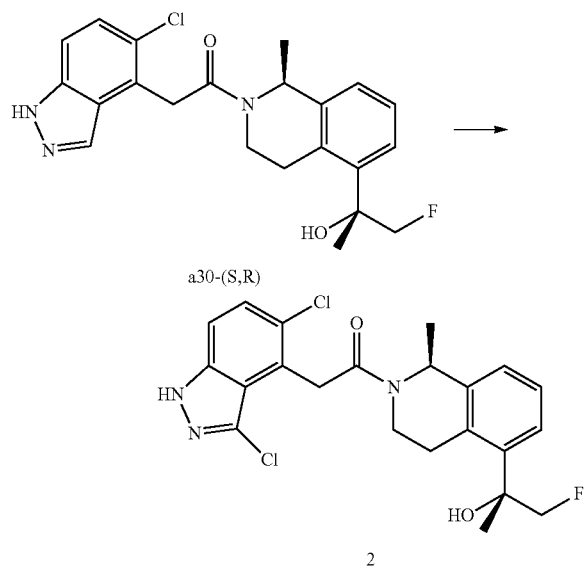

2-(5-Chloro-1H-indazol-4-yl)-1-[(1S)-5-[(1R)-2-fluoro-1-hydroxy-1-methyl-ethyl]-1-methyl-3,4-dihydro-1H-isoquinolin-2-yl]ethanone a30-(S,R) (75 mg, 0.1803 mmol) was dissolved in THF (2 mL) at rt and NCS (30 mg, 0.2157 mmol) was added. The reaction mixture was stirred at rt for 4 h, then concentrated under vacuum. The residue was purified by reverse phase chromatography (Basic mode, LCMS prep) to yield 26 mg of 2-(3,5-dichloro-1H-indazol-4-yl)-1-[(1S)-5-[(1R)-2-fluoro-1-hydroxy-1-methyl-ethyl]-1-methyl-3,4-dihydro-1H-isoquinolin-2-yl]ethanone 2 as a white solid.

Yield: 32%.

LCMS (ES⁺): 450.0/452.0/454.0 (M+H)⁺, 100% purity.

The following compounds may be synthesized according a method analogous to Method B. When commercially available, starting material are identified by their CAS Register Numbers.

| No | Starting material | Conditions, Time | Purification conditions | Yield (%) |
|---|---|---|---|---|
| 3 | a30-(S,S) | rt for 4 h, then reflux for 4 h | Basic mode, LCMS prep | 36 |
| 4 | a31 | rt for 4 h | Basic mode, LCMS prep | 19 |
| 5 | a32 | rt for 4 h | Basic mode, LCMS prep | 26 |
| 6 | a33-A | rt, overnight | Trituration in Et₂O | 99 |
| 7 | a33-B | rt, overnight | Trituration in Et₂O | 99 |
| 8 | a34 | rt, overnight | Basic mode, LCMS prep | 34 |
| 9 | a35 | 70° C. for 4 h | Basic mode, LCMS prep | 34 |
| 10 | a36 | 70° C. for 4 h | Basic mode, LCMS prep | 29 |
| 11 | a37 | 70° C. for 4 h | Basic mode, LCMS prep | 30 |
| a78 | a77 | rt, overnight | — | 81 (crude) |

2-(3,5-dichloro-1H-indazol-4-yl)-1-[(1S)-5-[(1S)-2-fluoro-1-hydroxy-1-methyl-ethyl]-1-methyl-3,4-dihydro-1H-isoquinolin-2-yl]ethanone 3

LCMS (ES⁺): 450.0/452.0/454.0 (M+H)⁺, 100% purity.

2-(3,5-dichloro-1H-indazol-4-yl)-1-[(1S)-5-[(1R)-2,2-difluoro-1-hydroxy-ethyl]-1-methyl-3,4-dihydro-1H-isoquinolin-2-yl]ethanone 4

LCMS (ES⁺): 454.0/456.0/458.0 (M+H)⁺, 100% purity.

2-(3,5-dichloro-1H-indazol-4-yl)-1-[(1S)-5-[(1S)-2,2-difluoro-1-hydroxy-ethyl]-1-methyl-3,4-dihydro-1H-isoquinolin-2-yl]ethanone 5

LCMS (ES⁺): 454.0/456.0/458.0 (M+H)⁺, 100% purity.

2-(3,5-dichloro-1H-indazol-4-yl)-1-[(1S)-5-[2,2-difluoro-1-hydroxy-1-methyl-ethyl]-1-methyl-3,4-dihydro-1H-isoquinolin-2-yl]ethanone isomer A 6

LCMS (ES⁺): 468.0/470.0/472.0 (M+H)⁺, 96.4% purity.

2-(3,5-dichloro-1H-indazol-4-yl)-1-[(1S)-5-[2,2-difluoro-1-hydroxy-1-methyl-ethyl]-1-methyl-3,4-dihydro-1H-isoquinolin-2-yl]ethanone isomer B 7

LCMS (ES⁺): 468.0/470.0/472.0 (M+H)⁺, 96.5% purity.

2-(3,5-dichloro-2-methyl-indazol-4-yl)-1-[(1S)-5-[(1R)-2,2-difluoro-1-hydroxy-ethyl]-1-methyl-3,4-dihydro-1H-isoquinolin-2-yl]ethanone 8

LCMS (ES⁺): 468.0/470.0/472.0 (M+H)⁺, 99.2% purity.

2-(3,5-dichloro-2-methyl-indazol-4-yl)-1-[(1S)-5-[(1S)-2,2-difluoro-1-hydroxy-ethyl]-1-methyl-3,4-dihydro-1H-isoquinolin-2-yl]ethanone 9

LCMS (ES⁺): 468.0/470.0/472.0 (M+H)⁺, 99.1% purity.

2-(3,5-dichloro-1-methyl-indazol-4-yl)-1-[(1S)-5-[(1R)-2,2-difluoro-1-hydroxy-ethyl]-1-methyl-3,4-dihydro-1H-isoquinolin-2-yl]ethanone 10

LCMS (ES⁺): 468.0/470.0/472.0 (M+H)⁺, 92.1% purity.
¹H NMR (400 MHz, DMSO-d₆) δ 7.55 (d, J=9.1 Hz, 1H), 7.53-7.34 (m, 1H), 7.34-7.19 (m, 3H), 6.11 (dd, J=7.2, 5.1 Hz, 1H), 5.45 (dq, J=13.6, 6.7 Hz, 1H), 4.98 (dd, J=10.8, 5.6 Hz, 1H), 4.38 (dd, J=18.6, 16.8 Hz, 1H), 4.28-4.15 (m, 1H), 4.08 (d, J=2.6 Hz, 3H), 3.67 (ddd, J=13.9, 9.7, 4.8 Hz, 1H), 3.20-2.94 (m, 2H), 1.63 (d, J=6.6 Hz, 1H), 1.39 (d, J=6.8 Hz, 2H).

2-(3,5-dichloro-1-methyl-indazol-4-yl)-1-[(1S)-5-[(1S)-2,2-difluoro-1-hydroxy-ethyl]-1-methyl-3,4-dihydro-1H-isoquinolin-2-yl]ethanone 11

LCMS (ES+): 468.0/470.0/472.0 (M+H)+, 99.2% purity.
1H NMR (400 MHz, DMSO-d6) δ 7.55 (d, J=9.1 Hz, 1H), 7.42 (ddd, J=9.3, 6.3, 2.7 Hz, 1H), 7.35-7.19 (m, 3H), 6.14 (s, 1H), 6.05 (t, J=4.9 Hz, 0H), 5.45 (q, J=6.6 Hz, 1H), 5.01 (d, J=11.5 Hz, 1H), 4.48-4.30 (m, 1H), 4.30-4.17 (m, 2H), 4.07 (d, J=3.1 Hz, 3H), 3.61 (ddd, J=14.1, 10.8, 4.2 Hz, 1H), 3.14-2.88 (m, 2H), 1.63 (d, J=6.6 Hz, 1H), 1.40 (d, J=6.8 Hz, 2H).

2-(6-bromo-3,5-dichloro-pyrazolo[1,5-a]pyridin-4-yl)-1-[(1S)-5-(2,2-difluoro-1-hydroxy-1-methyl-ethyl)-1-methyl-3,4-dihydro-1H-isoquinolin-2-yl]ethanone isomer A a78

LCMS (ES+): 547.0/549.0/551.0 (M+H)+, 92.7% purity.

C.3. Method C. Synthesis of 2-(3,5-dichloro-2-methyl-indazol-4-yl)-1-[(1S)-5-[2,2-difluoro-1-hydroxy-1-methyl-ethyl]-1-methyl-3,4-dihydro-1H-isoquinolin-2-yl]ethanone isomer A 12 and isomer B 13

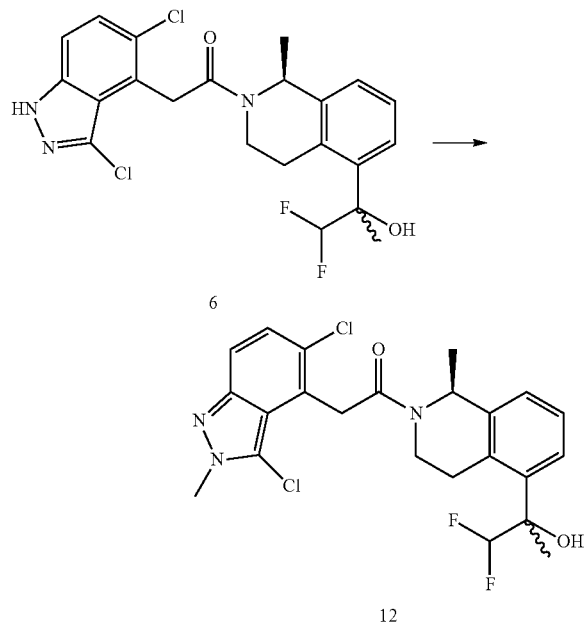

Trimethyloxonium tetrafluoroborate (33 mg, 0.21 mmol) was added to a solution of 2-(3,5-dichloro-1H-indazol-4-yl)-1-[(1S)-5-[2,2-difluoro-1-hydroxy-1-methyl-ethyl]-1-methyl-3,4-dihydro-1H-isoquinolin-2-yl]ethanone isomer A 6 (100 mg, 0.21 mmol) in DCM (1 mL) at rt. The reaction mixture was stirred at rt for 1 h, then diluted with DCM (5 mL) and washed with water (2 mL). The organic layer was dried over MgSO4 and concentrated under vacuum. The residue was purified by reverse phase chromatography (Basic mode, LCMS prep) to yield 30 mg of 2-(3,5-dichloro-2-methyl-indazol-4-yl)-1-[(1S)-5-[2,2-difluoro-1-hydroxy-1-methyl-ethyl]-1-methyl-3,4-dihydro-1H-isoquinolin-2-yl]ethanone isomer A 12 as a white solid. Yield: 29%
LCMS (ES+): 482.0/484.0/486.0 (M+H)+, 89.4% purity 2-(3,5-dichloro-2-methyl-indazol-4-yl)-1-[(1S)-5-[2,2-difluoro-1-hydroxy-1-methyl-ethyl]-1-methyl-3,4-dihydro-1H-isoquinolin-2-yl]ethanone isomer B13

Compound 13 may be synthesized according to the same method using 2-(3,5-dichloro-1H-indazol-4-yl)-1-[(1S)-5-[2,2-difluoro-1-hydroxy-1-methyl-ethyl]-1-methyl-3,4-dihydro-1H-isoquinolin-2-yl]ethanone isomer B 7 as starting material.
Yield: 34%
LCMS (ES+): 482.0/484.0/486.0 (M+H)+, 96.1% purity C.4. Method A2. Synthesis of 2-(5-chloro-1-tetrahydropyran-2-yl-pyrazolo[3,4-b]pyridin-4-yl)-1-[(1S)-5-[(1S)-2-fluoro-1-hydroxy-1-methyl-ethyl]-1-methyl-3,4-dihydro-1H-isoquinolin-2-yl]ethanone a67-(S,S)

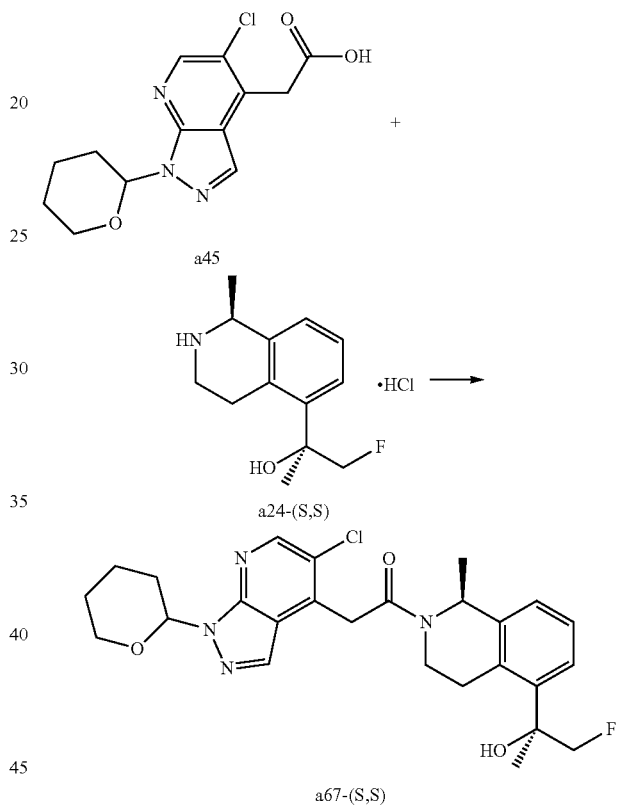

(1S)-1-fluoro-2-[(1S)-1-methyl-1,2,3,4-tetrahydroisoquinolin-5-yl]propan-2-ol hydrochloride a24-(S,S) (645 mg, 2.45 mmol) and 2-(5-chloro-1-tetrahydropyran-2-yl-pyrazolo[3,4-b]pyridin-4-yl)acetic acid a45 (734 mg, 2.45 mmol) and HBTU (1130 mg, 2.95 mmol) were dissolved in DMF (6 mL) at rt, then DIPEA (982 mg, 7.366 mmol) was added. The reaction mixture was stirred at rt for 2 h. The reaction mixture was quenched with water and extracted twice with EtOAc. The organic layer was washed three times with brine, then dried over MgSO4 and concentrated under vacuum. The residue was purified by column chromatography from 40 to 100% EtOAc in heptane as eluent to yield 946 mg of 2-(5-chloro-1-tetrahydropyran-2-yl-pyrazolo[3,4-b]pyridin-4-yl)-1-[(1S)-5-[(1S)-2-fluoro-1-hydroxy-1-methyl-ethyl]-1-methyl-3,4-dihydro-1H-isoquinolin-2-yl]ethanone a67-(S,S).
Yield (crude): 77%.
LCMS (ES+): 501.2/503.2 (M+H)+.
The following compounds may be synthesized according a method analogous to Method A2. When commercially available, starting material are identified by their CAS Register Numbers.

| No | Acids II | Amines III | Conditions, Time | Purification conditions | Yield (%) |
|---|---|---|---|---|---|
| a67-(S,R) | a45 | a24-(S,R) | rt, 2 h | NP using 0 to 15% MeOH in DCM | 95 |
| a68-A | a45 | a29-A | rt, 2 h | NP using 40 to 100% EtOAc in heptane | 96 |
| a68-B | a45 | a29-B | rt, 2 h | NP using 40 to 100% EtOAc in heptane | 88 |
| a69 | a45 | a63 | rt, 2 h | NP using 40 to 100% EtOAc in heptane | 85 |
| a70-(S,R) | a48 | a24-(S,R) | rt, 2 h | NP using 40 to 100% EtOAc in heptane, then Basic mode standard LC | quantitative |
| a70-(S,S) | a48 | a24-(S,S) | rt, 2 h | NP using 40 to 100% EtOAc in heptane | quantitative |
| a71-A | a48 | a29-A | rt, 2 h | NP using 40 to 100% EtOAc in heptane | 74 |
| a71-B | a48 | a29-B | rt, 2 h | NP using 40 to 100% EtOAc in heptane | 73 |
| a72 | a48 | a63 | rt, 2 h | NP using 40 to 100% EtOAc in heptane | 77 |
| a73-(S,R) | a11 | a24-(S,R) | rt, 2 h | NP using 40 to 100% EtOAc in heptane | 80 |
| a73-(S,S) | a11 | a24-(S,S) | rt, 2 h | NP using 40 to 100% EtOAc in heptane | 83 |
| a74-A | a11 | a29-A | rt, 2 h | Basic mode, LCMS prep | 71 |
| a74-B | a11 | a29-B | rt, 2 h | Basic mode, LCMS prep | 56 |
| a75 | a11 | a63 | rt, 2 h | Basic mode, LCMS prep | 71 |
| a77 | a61 | a29-A | rt, overnight | — | 97 |

2-(5-chloro-1-tetrahydropyran-2-yl-pyrazolo[3,4-b]pyridin-4-yl)-1-[(1S)-5-[(1R)-2-fluoro-1-hydroxy-1-methyl-ethyl]-1-methyl-3,4-dihydro-1H-isoquinolin-2-yl]ethanone a67-(S,R)

LCMS (ES$^+$): 501.1/503.1 (M+H)$^+$.

2-(5-chloro-1-tetrahydropyran-2-yl-pyrazolo[3,4-b]pyridin-4-yl)-1-[(1S)-5-(2,2-difluoro-1-hydroxy-1-methyl-ethyl)-1-methyl-3,4-dihydro-1H-isoquinolin-2-yl]ethanone isomer A a68-A

LCMS (ES$^+$): 519.1/521.1 (M+H)$^+$.

2-(5-chloro-1-tetrahydropyran-2-yl-pyrazolo[3,4-b]pyridin-4-yl)-1-[(1S)-5-(2,2-difluoro-1-hydroxy-1-methyl-ethyl)-1-methyl-3,4-dihydro-1H-isoquinolin-2-yl]ethanone isomer B a68-B

LCMS (ES$^+$): 519.1/521.1 (M+H)$^+$.

2-(5-chloro-1-tetrahydropyran-2-yl-pyrazolo[3,4-b]pyridin-4-yl)-1-[(1S)-5-[2-fluoro-1-(fluoromethyl)-1-hydroxy-ethyl]-1-methyl-3,4-dihydro-1H-isoquinolin-2-yl]ethanone a69

LCMS (ES$^+$): 519.1/521.1 (M+H)$^+$.

2-(5-chloro-1-methyl-pyrazolo[3,4-b]pyridin-4-yl)-1-[(1S)-5-((1R)-2-fluoro-1-hydroxy-1-methyl-ethyl)-1-methyl-3,4-dihydro-1H-isoquinolin-2-yl]ethanone a70-(S,R)

LCMS (ES$^+$): 431.1/433.1 (M+H)$^+$.

2-(5-chloro-1-methyl-pyrazolo[3,4-b]pyridin-4-yl)-1-[(1S)-5-((1S)-2-fluoro-1-hydroxy-1-methyl-ethyl)-1-methyl-3,4-dihydro-1H-isoquinolin-2-yl]ethanone a70-(S,S)

LCMS (ES$^+$): 431.1/433.1 (M+H)$^+$.

2-(5-chloro-1-methyl-pyrazolo[3,4-b]pyridin-4-yl)-1-[(1S)-5-(2,2-difluoro-1-hydroxy-1-methyl-ethyl)-1-methyl-3,4-dihydro-1H-isoquinolin-2-yl]ethanone isomer A a71-A

LCMS (ES$^+$): 449.1/451.1 (M+H)$^+$.

2-(5-chloro-1-methyl-pyrazolo[3,4-b]pyridin-4-yl)-1-[(1S)-5-(2,2-difluoro-1-hydroxy-1-methyl-ethyl)-1-methyl-3,4-dihydro-1H-isoquinolin-2-yl]ethanone isomer B a71-B

LCMS (ES$^+$): 449.1/451.1 (M+H)$^+$.

2-(5-chloro-1-methyl-pyrazolo[3,4-b]pyridin-4-yl)-1-[(1S)-5-[2-fluoro-1-(fluoromethyl)-1-hydroxy-ethyl]-1-methyl-3,4-dihydro-1H-isoquinolin-2-yl]ethanone a72

LCMS (ES$^+$): 449.1/451.1 (M+H)$^+$.

2-(5-chloro-1-methyl-indazol-4-yl)-1-[(1S)-5-((1R)-2-fluoro-1-hydroxy-1-methyl-ethyl)-1-methyl-3,4-dihydro-1H-isoquinolin-2-yl]ethanone a73-(S,R)

LCMS (ES$^+$): 430.1/432.1 (M+H)$^+$.

2-(5-chloro-1-methyl-indazol-4-yl)-1-[(1S)-5-((1S)-2-fluoro-1-hydroxy-1-methyl-ethyl)-1-methyl-3,4-dihydro-1H-isoquinolin-2-yl]ethanone a73-(S,S)

LCMS (ES$^+$): 430.1/432.1 (M+H)$^+$.

2-(5-chloro-1-methyl-indazol-4-yl)-1-[(1S)-5-((2,2-difluoro-1-hydroxy-1-methyl-ethyl)-1-methyl-3,4-dihydro-1H-isoquinolin-2-yl]ethanone isomer A a74-A

LCMS (ES$^+$): 448.0/450.0 (M+H)$^+$.

2-(5-chloro-1-methyl-indazol-4-yl)-1-[(1S)-5-((2,2-difluoro-1-hydroxy-1-methyl-ethyl)-1-methyl-3,4-dihydro-1H-isoquinolin-2-yl]ethanone isomer B a74-B

LCMS (ES+): 448.0/450.0 (M+H)+.

2-(5-chloro-1-methyl-indazol-4-yl)-1-[(1S)-5-[2-fluoro-1-(fluoromethyl)-1-hydroxy-ethyl]-1-methyl-3,4-dihydro-1H-isoquinolin-2-yl]ethanone a75

LCMS (ES+): 448.0/450.0 (M+H)+.

2-(6-bromo-5-chloro-pyrazolo[1,5-a]pyridin-4-yl)-1-[(1S)-5-(2,2-difluoro-1-hydroxy-1-methyl-ethyl)-1-methyl-3,4-dihydro-1H-isoquinolin-2-yl]ethanone isomer A a77

LCMS (ES+): 512.0/514.0/516.0 (M+H)+.

C.5. Method B2. Synthesis of 2-(3,5-dichloro-1H-pyrazolo[3,4-b]pyridin-4-yl)-1-[(1S)-5-[(1S)-2-fluoro-1-hydroxy-1-methyl-ethyl]-1-methyl-3,4-dihydro-1H-isoquinolin-2-yl]ethanone 14

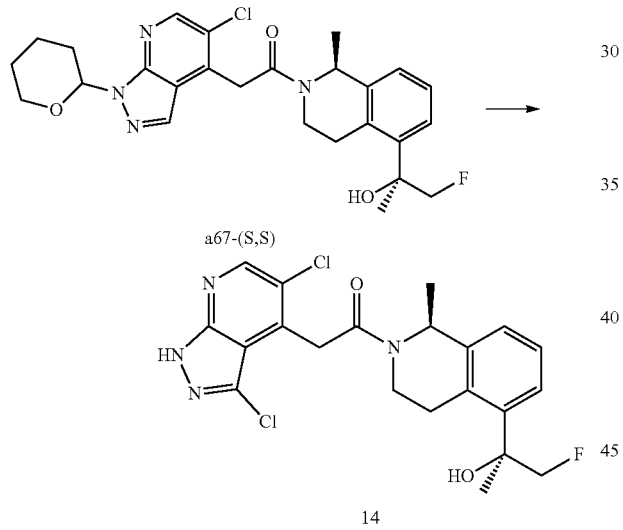

Step 1: A mixture of 2-(5-chloro-1-tetrahydropyran-2-yl-pyrazolo[3,4-b]pyridin-4-yl)-1-[(1S)-5-[(1S)-2-fluoro-1-hydroxy-1-methyl-ethyl]-1-methyl-3,4-dihydro-1H-isoquinolin-2-yl]ethanone a67-(S,S) (916 mg, 1.83 mmol), trichloroisocyanuric acid (140 mg, 0.6 mmol) and zeolite Y, hydrogen (5 mg) in ACN (12 mL) was stirred at 65° C. for 2 h. The reaction mixture was concentrated under vacuum and used in the next step without further purification.

Step 2: The mixture was dissolved in a 4N solution of HCl in Dioxane. The reaction mixture was stirred at rt for 3 h, then neutralized with an aqueous saturated solution of NaHCO$_3$ and extracted twice with DCM. The organic layer was dried over MgSO$_4$ and concentrated under vacuum. The crude residue was purified by column chromatography from 40 to 100% EtOAc in heptane as eluent, then by reverse phase chromatography (Basic mode, standard LC) to afford 380 mg of 2-(3,5-dichloro-1H-pyrazolo[3,4-b]pyridin-4-yl)-1-[(1S)-5-[(1S)-2-fluoro-1-hydroxy-1-methyl-ethyl]-1-methyl-3,4-dihydro-1H-isoquinolin-2-yl]ethanone 14.

Yield: 44.7% (2 steps).

LCMS (ES+): 451.2/453.2/455.2 (M+H)+, 98.5% purity $^1$H NMR (400 MHz, DMSO-d$_6$) δ 14.13 (s, 1H), 8.61 (s, 1H), 7.36-7.11 (m, 4H), 5.48 (m, 1H), 5.43-5.28 (m, 1H), 4.69-4.27 (m, 4H), 4.04-3.70 (m, 2H), 3.56-3.36 (m, 1H), 3.30-3.08 (m, 1H), 1.62 (d, J=6.6 Hz, 1H), 1.53 (dd, J=9.4, 2.3 Hz, 3H), 1.37 (d, J=6.7 Hz, 2H).

The following compounds may be synthesized according a method analogous to Method B2. When commercially available, starting material are identified by their CAS Register Numbers.

| No | Starting material | Purification conditions | Yield (%) |
|---|---|---|---|
| 15 | a67-(S,R) | Basic RP-LCMS | quantitative |
| 16 | a68-A | NP using 40 to 100% EtOAc in hexanes | 28 |
| 17 | a68-B | NP using 40 to 100% EtOAc in hexanes | 33 |
| 18 | a69 | NP using 40 to 100% EtOAc in hexanes | 32 |

2-(3,5-dichloro-1H-pyrazolo[3,4-b]pyridin-4-yl)-1-[(1S)-5-[(1R)-2-fluoro-1-hydroxy-1-methyl-ethyl]-1-methyl-3,4-dihydro-1H-isoquinolin-2-yl]ethanone 15

LCMS (ES+): 451.2/453.2/455.2 (M+H)+, 97.7% purity.

$^1$H NMR (400 MHz, DMSO-d$_6$) δ 14.11 (s, 1H), 8.61 (s, 1H), 7.37-7.12 (m, 3H), 5.55-5.21 (m, 2H), 4.81-4.23 (m, 4H), 4.01-3.74 (m, 2H), 3.61-3.33 (m, 1H), 1.69-1.48 (m, 3H), 1.46-1.11 (m, 3H).

2-(3,5-dichloro-1H-pyrazolo[3,4-b]pyridin-4-yl)-1-[(1S)-5-[2,2-difluoro-1-hydroxy-1-methyl-ethyl]-1-methyl-3,4-dihydro-1H-isoquinolin-2-yl]ethanone isomer A 16

LCMS (ES+): 469.0/471.0/473.0 (M+H)+, 95.6% purity.

$^1$H NMR (400 MHz, DMSO-d$_6$) δ 14.11 (s, 1H), 8.61 (s, 1H), 7.37-7.13 (m, 3H), 6.20 (td, J=55.7, 8.5 Hz, 1H), 5.89 (d, J=24.1 Hz, 1H), 5.40 (dq, J=29.1, 6.6 Hz, 1H), 4.63-4.26 (m, 2H), 4.08-3.85 (m, 1H), 3.76 (ddd, J=12.6, 8.4, 4.1 Hz, 1H), 3.62-3.39 (m, 1H), 3.25-3.15 (m, 1H), 1.69-1.56 (m, 4H), 1.39 (d, J=6.7 Hz, 2H).

2-(3,5-dichloro-1H-pyrazolo[3,4-b]pyridin-4-yl)-1-[(1S)-5-[2,2-difluoro-1-hydroxy-1-methyl-ethyl]-1-methyl-3,4-dihydro-1H-isoquinolin-2-yl]ethanone isomer A 17

LCMS (ES+): 469.0/471.0/473.0 (M+H)+, 95.4% purity.

$^1$H NMR (400 MHz, DMSO-d$_6$) δ 14.11 (s, 1H), 8.61 (s, 1H), 7.38-7.16 (m, 3H), 6.21 (t, J=55.7 Hz, 1H), 5.93 (d, J=19.7 Hz, 1H), 5.39 (dq, J=35.9, 6.7 Hz, 1H), 4.64-4.24 (m, 2H), 3.95-3.76 (m, 2H), 3.54 (dt, J=16.7, 5.8 Hz, 1H), 3.41 (ddt, J=26.8, 14.7, 5.7 Hz, 1H), 1.61 (q, J=3.7 Hz, 4H), 1.36 (d, J=6.7 Hz, 2H).

2-(3,5-dichloro-1H-pyrazolo[3,4-b]pyridin-4-yl)-1-[(1S)-5-[2-fluoro-1-(fluoromethyl)-1-hydroxy-ethyl]-1-methyl-3,4-dihydro-1H-isoquinolin-2-yl]ethanone 18

LCMS (ES⁺): 469.0/471.0/473.0 (M+H)⁺, 95.2% purity.

¹H NMR (400 MHz, DMSO-d₆) δ 14.11 (s, 1H), 8.61 (s, 1H), 7.41-7.13 (m, 3H), 6.01 (d, J=21.0 Hz, 1H), 5.40 (dq, J=31.3, 6.7 Hz, 1H), 4.88-4.26 (m, 6H), 4.07-3.73 (m, 2H), 3.56-3.33 (m, 1H), 1.50 (dd, J=100.4, 6.6 Hz, 3H). 6.6 Hz, 3H).

C.6. Method B3. Synthesis of 2-(3,5-dichloro-1-methyl-pyrazolo[3,4-b]pyridin-4-yl)-1-[(1S)-5-((1R)-2-fluoro-1-hydroxy-1-methyl-ethyl)-1-methyl-3,4-dihydro-1H-isoquinolin-2-yl]ethanone 19

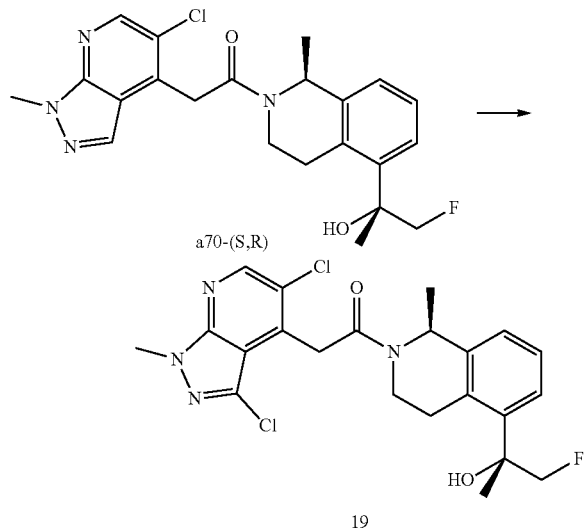

a70-(S,R)

19

A mixture of 2-(5-chloro-1-methyl-pyrazolo[3,4-b]pyridin-4-yl)-1-[(1S)-5-((1R)-2-fluoro-1-hydroxy-1-methyl-ethyl)-1-methyl-3,4-dihydro-1H-isoquinolin-2-yl]ethanone a70-(S,R) (229 mg, 0.53 mmol), trichloroisocyanuric acid (41 mg, 0.17 mmol) and zeolite Y, hydrogen (5 mg) in ACN (6 mL) was stirred at 60° C. for 2 h. The reaction mixture was concentrated under vacuum. The crude residue was purified by column chromatography from 0 to 5% MeOH in DCM as eluent, then by reverse phase chromatography (Basic mode, standard LC) to afford 75 mg of 2-(3,5-dichloro-1-methyl-pyrazolo[3,4-b]pyridin-4-yl)-1-[(1S)-5-((1R)-2-fluoro-1-hydroxy-1-methyl-ethyl)-1-methyl-3,4-dihydro-1H-isoquinolin-2-yl]ethanone 19. Yield: 30%

LCMS (ES⁺): 465.0/467.0/469.0 (M+H)⁺, 98% purity.

¹H NMR (400 MHz, DMSO-d₆) δ 8.66 (s, 1H), 7.37-7.13 (m, 3H), 5.54-5.27 (m, 2H), 4.87-4.25 (m, 5H), 4.03 (s, 3H), 3.99-3.76 (m, 1H), 3.51 (tt, J=17.0, 6.0 Hz, 1H), 3.27-3.12 (m, 1H), 1.68-1.47 (m, 3H), 1.37 (dd, J=6.8, 2.1 Hz, 2H).

The following compounds may be synthesized according a method analogous to Method B3. When commercially available, starting material are identified by their CAS Register Numbers.

| No | Starting material | Conditions, Time | Purification conditions | Yield (%) |
|---|---|---|---|---|
| 20 | a70-(S,S) | 60° C., 2 h | Basic mode, LCMS prep | 45 |
| 21 | a71-A | 60° C., 2 h | Basic mode, LCMS prep | 61 |
| 22 | a71-B | 60° C., 2 h | Basic mode, LCMS prep | 20 |
| 23 | a72 | 60° C., 2 h | Basic mode, LCMS prep | 48 |
| 24 | a73-(S,R) | 60° C., 3 h | Basic mode, LCMS prep | 69 |
| 25 | a73-(S,S) | 60° C., 3 h | Basic mode, LCMS prep | 55 |
| 26 | a74-A | 60° C., 2 h | Basic mode, LCMS prep | 72 |
| 27 | a74-B | 60° C., 1 h | Basic mode, LCMS prep | 63 |
| 28 | a75 | 60° C., 3 h | Basic mode, LCMS prep | 83 |
| 30 | a76 | rt, overnight | Basic mode, LCMS prep | 52 |

2-(3,5-dichloro-1-methyl-pyrazolo[3,4-b]pyridin-4-yl)-1-[(1S)-5-((1S)-2-fluoro-1-hydroxy-1-methyl-ethyl)-1-methyl-3,4-dihydro-1H-isoquinolin-2-yl]ethanone 20

LCMS (ES⁺): 465.0/467.0/469.0 (M+H)+, 92.7% purity.

¹H NMR (400 MHz, DMSO-d₆) δ 8.66 (s, 1H), 7.39-7.11 (m, 3H), 5.51-5.28 (m, 2H), 4.66-4.28 (m, 4H), 4.03 (s, 3H), 3.79 (ddd, J=12.5, 7.8, 4.3 Hz, 1H), 3.56-3.33 (m, 2H), 3.28-3.05 (m, 1H), 1.70-1.48 (m, 4H), 1.37 (d, J=6.7 Hz, 2H).

2-(3,5-dichloro-1-methyl-pyrazolo[3,4-b]pyridin-4-yl)-1-[(1S)-5-[2,2-difluoro-1-hydroxy-1-methyl-ethyl]-1-methyl-3,4-dihydro-1H-isoquinolin-2-yl]ethanone isomer A 21

LCMS (ES⁺): 483.0/485.0/487.0 (M+H)+, 98.2% purity.

¹H NMR (400 MHz, DMSO-d₆) δ 8.66 (s, 1H), 7.43-7.08 (m, 3H), 6.21 (t, J=55.7 Hz, 1H), 5.93 (d, J=19.6 Hz, 1H), 5.38 (dq, J=37.2, 6.7 Hz, 1H), 4.67-4.25 (m, 2H), 4.03 (s, 3H), 3.97-3.75 (m, 2H), 3.54 (dt, J=16.8, 5.8 Hz, 1H), 3.38 (dt, J=15.8, 5.6 Hz, 1H), 1.61 (q, J=3.4 Hz, 4H), 1.36 (d, J=6.7 Hz, 2H).

2-(3,5-dichloro-1-methyl-pyrazolo[3,4-b]pyridin-4-yl)-1-[(1S)-5-[2,2-difluoro-1-hydroxy-1-methyl-ethyl]-1-methyl-3,4-dihydro-1H-isoquinolin-2-yl]ethanone isomer B 22

LCMS (ES⁺): 483.0/485.0/487.0 (M+H)⁺, 100% purity.

¹H NMR (400 MHz, DMSO-d₆) δ 8.66 (s, 1H), 7.35-7.15 (m, 3H), 6.20 (td, J=55.8, 8.5 Hz, 1H), 5.89 (d, J=22.9 Hz, 1H), 5.40 (dq, J=30.5, 6.7 Hz, 1H), 4.63-4.26 (m, 2H), 4.03 (s, 3H), 3.92 (dt, J=12.1, 5.8 Hz, 1H), 3.76 (ddd, J=12.7, 8.4, 4.1 Hz, 1H), 3.58-3.44 (m, 1H), 3.28-3.16 (m, 1H), 1.68-1.55 (m, 4H), 1.38 (d, J=6.7 Hz, 2H).

2-(3,5-dichloro-1-methyl-pyrazolo[3,4-b]pyridin-4-yl)-1-[(1S)-5-[2-fluoro-1-(fluoromethyl)-1-hydroxy-ethyl]-1-methyl-3,4-dihydro-1H-isoquinolin-2-yl]ethanone 23

LCMS (ES⁺): 483.0/485.0/487.0 (M+H)⁺, 90.5% purity.

¹H NMR (400 MHz, DMSO-d₆) δ 8.66 (s, 1H), 7.36-7.17 (m, 3H), 6.01 (d, J=20.9 Hz, 1H), 5.49-5.27 (m, 1H), 4.87-4.27 (m, 7H), 4.03 (s, 3H), 3.99-3.34 (m, 2H), 3.26-3.08 (m, 1H), 1.50 (dd, J=100.7, 6.7 Hz, 3H).

2-(3,5-dichloro-1-methyl-indazol-4-yl)-1-[(1S)-5-[(1R)-2-fluoro-1-hydroxy-1-methyl-ethyl]-1-methyl-3,4-dihydro-1H-isoquinolin-2-yl]ethanone 24

LCMS (ES⁺): 464.2/466.2/468.2 (M+H)⁺, 97.6% purity.
¹H NMR (400 MHz, DMSO-d₆) δ 7.65 (dd, J=9.0, 1.6 Hz, 1H), 7.50 (d, J=9.0 Hz, 1H), 7.40-7.10 (m, 3H), 5.62-5.27 (m, 2H), 4.87-4.19 (m, 4H), 4.01 (s, 3H), 3.98-3.72 (m, 1H), 3.49 (tdd, J=17.7, 8.4, 5.8 Hz, 1H), 3.27-3.09 (m, 1H), 1.61 (d, J=6.6 Hz, 1H), 1.59-1.48 (m, 3H), 1.36 (dd, J=6.8, 2.0 Hz, 2H).

2-(3,5-dichloro-1-methyl-indazol-4-yl)-1-[(1S)-5-[(1S)-2-fluoro-1-hydroxy-1-methyl-ethyl]-1-methyl-3,4-dihydro-1H-isoquinolin-2-yl]ethanone 25

LCMS (ES⁺): 464.2/466.2/468.2 (M+H)⁺, 93.1% purity.
¹H NMR (400 MHz, DMSO-d₆) δ 7.65 (dd, J=9.1, 1.3 Hz, 1H), 7.50 (d, J=9.0 Hz, 1H), 7.36-7.11 (m, 3H), 5.46 (d, J=20.9 Hz, 1H), 5.35 (q, J=6.7 Hz, 1H), 4.69-4.23 (m, 4H), 4.01 (s, 3H), 3.97-3.70 (m, 1H), 3.54-3.33 (m, 1H), 3.30-3.08 (m, 1H), 1.61 (d, J=6.6 Hz, 1H), 1.53 (dd, J=11.8, 2.3 Hz, 3H), 1.36 (d, J=6.8 Hz, 2H).

2-(3,5-dichloro-1-methyl-indazol-4-yl)-1-[(1S)-5-[2,2-difluoro-1-hydroxy-1-methyl-ethyl]-1-methyl-3,4-dihydro-1H-isoquinolin-2-yl]ethanone isomer A 26

LCMS (ES⁺): 482.0/484.0/486.0 (M+H)⁺, 100% purity
¹H NMR (400 MHz, DMSO-d₆) δ 7.65 (dd, J=9.1, 1.6 Hz, 1H), 7.50 (d, J=9.0 Hz, 1H), 7.40-7.12 (m, 3H), 6.21 (t, J=55.7 Hz, 1H), 5.92 (d, J=19.4 Hz, 1H), 5.39 (dq, J=38.7, 6.6 Hz, 1H), 4.59-4.19 (m, 2H), 4.01 (s, 3H), 3.95-3.33 (m, 3H), 1.61 (d, J=6.3 Hz, 4H), 1.35 (d, J=6.7 Hz, 2H).

2-(3,5-dichloro-1-methyl-indazol-4-yl)-1-[(1S)-5-[2,2-difluoro-1-hydroxy-1-methyl-ethyl]-1-methyl-3,4-dihydro-1H-isoquinolin-2-yl]ethanone isomer B 27

LCMS (ES₊): 482.0/484.0/486.0 (M+H)⁺, 100% purity
¹H NMR (400 MHz, DMSO-d₆) δ 7.65 (dd, J=9.1, 1.4 Hz, 1H), 7.50 (d, J=9.0 Hz, 1H), 7.34-7.15 (m, 3H), 6.20 (td, J=55.8, 7.7 Hz, 1H), 5.89 (d, J=23.6 Hz, 1H), 5.41 (dq, J=31.6, 6.6 Hz, 1H), 4.55-4.22 (m, 2H), 4.01 (s, 3H), 3.93 (dt, J=11.9, 5.6 Hz, 1H), 3.74 (ddd, J=12.7, 8.4, 4.0 Hz, 1H), 3.57-3.39 (m, 1H), 3.29-3.15 (m, 1H), 1.60 (d, J=9.2 Hz, 3H), 1.38 (d, J=6.7 Hz, 2H).

2-(3,5-dichloro-1-methyl-indazol-4-yl)-1-[(1S)-5-[2-fluoro-1-(fluoromethyl)-1-hydroxy-ethyl]-1-methyl-3,4-dihydro-1H-isoquinolin-2-yl]ethanone 28

LCMS (ES⁺): 482.0/484.0/486.0 (M+H)⁺, 100% purity
¹H NMR (400 MHz, DMSO-d₆) δ 7.65 (dd, J=9.0, 1.6 Hz, 1H), 7.50 (d, J=9.0 Hz, 1H), 7.39-7.14 (m, 3H), 5.40 (dq, J=34.8, 6.7 Hz, 1H), 4.90-4.21 (m, 6H), 4.01 (s, 3H), 3.98-3.40 (m, 2H), 3.28-3.07 (m, 1H), 1.62 (d, J=6.6 Hz, 1H), 1.54 (s, 1H), 1.37 (d, J=6.8 Hz, 2H).

2-(3,5-dichloropyrazolo[1,5-a]pyridin-4-yl)-1-[(1S)-5-[(1S)-2,2-difluoro-1-hydroxy-ethyl]-1-methyl-3,4-dihydro-1H-isoquinolin-2-yl]ethanone 30

LCMS (ES⁺): 454.0/456.0/458.0 (M+H)⁺, 100% purity

C.7. Synthesis of 2-(3,5-dichloro-6-cyclopropyl-pyrazolo[1,5-a]pyridin-4-yl)-1-[(1S)-5-(2,2-difluoro-1-hydroxy-1-methyl-ethyl)-1-methyl-3,4-dihydro-1H-isoquinolin-2-yl]ethanone isomer A 31

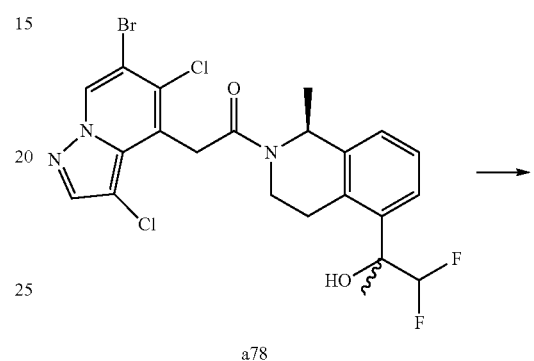

a78

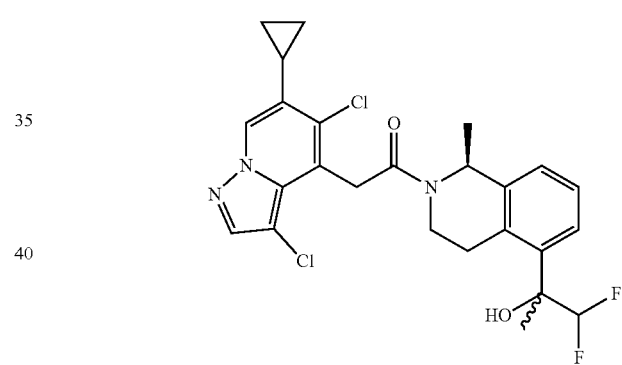

31

To a solution of 2-(6-bromo-3,5-dichloro-pyrazolo[1,5-a]pyridin-4-yl)-1-[(1S)-5-(2,2-difluoro-1-hydroxy-1-methyl-ethyl)-1-methyl-3,4-dihydro-1H-isoquinolin-2-yl]ethanone isomer A a78 (80 mg, 0.15 mmol) in 1,4-dioxane (2 mL) are added Cs₂CO₃ (95 mg, 0.29 mmol), water (0.2 mL, 10 mmol) and tetrakis(triphenylphosphine)palladium(0) (17 mg, 0.0146 mmol). To this reaction mixture was added cyclopropylboronic acid (264 mg, 2.92 mmol) and the reaction mixture is stirred at 80° C. for 4 h. The reaction mixture was filtered and the filtrate was concentrated under vacuum. The crude residue was purified by reverse phase chromatography (Basic mode, LCMS prep) to afford 35 mg of 2-(3,5-dichloro-6-cyclopropyl-pyrazolo[1,5-a]pyridin-4-yl)-1-[(1S)-5-(2,2-difluoro-1-hydroxy-1-methyl-ethyl)-1-methyl-3,4-dihydro-1H-isoquinolin-2-yl]ethanone isomer A 31 as a solid. Yield: 47% LCMS (ES⁺): 508.0/510.0/512.0 (M+H)⁺, 100% purity

C.8. Synthesis of 3,5-dichloro-4-[2-[(1S)-5-(2,2-difluoro-1-hydroxy-1-methyl-ethyl)-1-methyl-3,4-dihydro-1H-isoquinolin-2-yl]-2-oxo-ethyl]pyrazolo[1,5-a]pyridine-6-carbonitrile isomer A 32

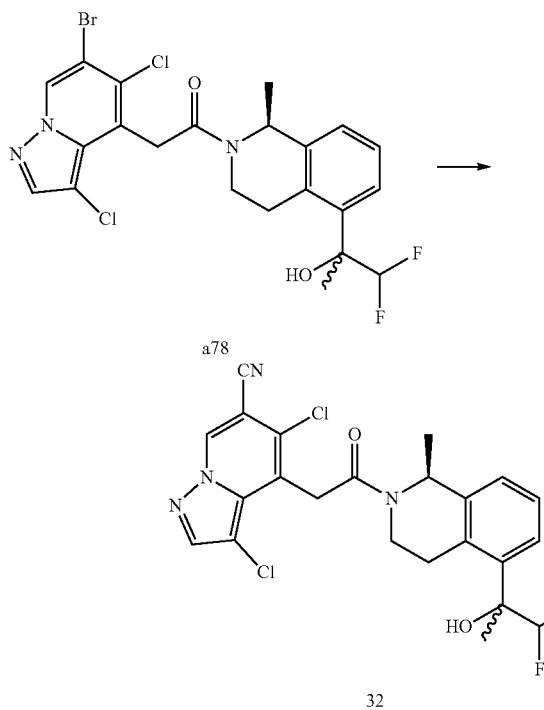

A mixture of 2-(6-bromo-3,5-dichloro-pyrazolo[1,5-a]pyridin-4-yl)-1-[(1S)-5-(2,2-difluoro-1-hydroxy-1-methyl-ethyl)-1-methyl-3,4-dihydro-1H-isoquinolin-2-yl]ethanone isomer A a78 (100 mg, 0.18 mmol) and copper(II) cyanide (33 mg, 0.37 mmol) in 1-methyl-2-pyrrolidinone (1.8 mL) was heated under microwave irradiations at 195° C. for 1 h. Brine was added to the reaction mixture. The organic layer was extracted twice with EtOAc, dried over MgSO$_4$ and concentrated under vacuum. The crude residue was purified by column chromatography using from 2 to 5% of MeOH/NH$_4$OH (9:1) in DCM, then by reverse phase chromatography (Basic mode, LCMS prep) to afford 8 mg of 3,5-dichloro-4-[2-[(1S)-5-(2,2-difluoro-1-hydroxy-1-methyl-ethyl)-1-methyl-3,4-dihydro-1H-isoquinolin-2-yl]-2-oxo-ethyl]pyrazolo[1,5-a]pyridine-6-carbonitrile isomer A 32 as a colorless lacquer.

Yield: 9%.
LCMS (ES$^+$): 493.0/495.0/497.0 (M+H)$^+$, 89.5% purity.

D. cAMP HTRF Assay.

Compounds according to the present invention do not directly activate the dopamine D1 receptor, but potentiate the effect of D1 agonists or the endogenous ligand on D1 receptors, dopamine, through an allosteric mechanism, and are therefore D1 positive allosteric modulators (D1 PAM).

Dopamine and other D1 agonists directly activate the dopamine D1 receptor by themselves.

The present assay allows to measure respectively the effects of compounds of the Examples in the absence of dopamine ("activation assay") and the effects of compounds of the Examples in the presence of dopamine ("potentiation assay").

The activation assay measures the stimulation of the production of cyclic adenosinemonophosphate (cAMP) in the HTRF assay, with the maximum increase in cAMP by increasing concentrations of the endogenous agonist, dopamine, defined as 100% activation. When tested compounds of the Examples lack significant direct agonist-like effects in that they produce less than 20% of activation (compared to dopamine maximal response) when present in a concentration of 10 μM.

The potentiation assay measures the ability of compounds to increase the levels of cAMP produced by a low-threshold concentration of dopamine. The concentration of dopamine used ([EC$_{20}$]) is designed to produce 20% stimulation compared to the maximal response (100%) seen with increasing the concentration of dopamine. To measure this potentiation we incubate increasing concentrations of the compound with the [EC$_2$O] of dopamine and measure the potentiation as increases in cAMP production. The pEC$_{50}$ of a compound is the −log 10 of the concentration of the compound which produces 50% of the potentiation of the cAMP levels and the Erel is the relative efficacy, defined as the maximal % potentiation produced by the compound compared to the maximal response produced by increasing concentrations of dopamine (Erel of 1=dopamine maximum response).

The particular conditions in which the compounds have been tested are described here below.

METHODS D1 Cell Culture

Cells were cultured at 37° C. in a humidified atmosphere of 5% CO$_2$. Cells were grown in DMEM-F12+GlutaMAX™-I medium (GIBCO®, Invitrogen, Merelbeke, Belgium) containing 10% fetal bovine serum (BioWhittaker®, Lonza, Verviers, Belgium), 400 μg/mL Geneticin (GIBCO®), 100 IU/mL Penicillin and 100 IU/mL Streptomycin (Pen-Strep solution, BioWhittaker®). LMtk (Ltk-) mouse fibroblast cells expressing the dopamine D1 receptor (BioSignal Inc, Montreal, Canada, now Perkin Elmer) were used as they have been shown to couple efficiently and give robust functional responses (Watts et al, 1995).

cAMP Assay

The measurement of changes in intracellular cyclic adenosinemonophopshpate (cAMP) was determined using the HTRF cAMP dynamic assay kit from CisBio (Codolet, France). Using homogenous time-resolved fluoresence technology, the assay is based on competition between native cAMP produced by cells and cAMP labelled with the dye d2. The tracer binding is determined by an anti-cAMP antibody labeled with cryptate. The effects of the compound alone (agonism) was determined by performing the assay in the absence of dopamine, whilst the effect of the compound as a positive allosteric modulator (PAM) was determined in the presence of an EC$_{20}$ concentration of dopamine. Cells (20, 000 per well) are incubated in 384 plates for 1 hour at room temperature in a final volume of 20 μLHBSS (Lonza, with calcium, magnesium and HEPES buffer 20 mM, pH 7.4) containing: isobutyl methylxanthine (Sigma, 0.1 mM final), varying concentrations of test compound (typically $10^{-9.5}$M to $10^{-4.5}$M) in the presence and absence of dopamine (1.1 nM final). The reaction is then terminated and the cells lysed by adding the d2 detection reagent in lysis buffer (10 microL) and the cryptate reagent in lysis buffer (10 microl) according to manufacturer's instructions. This is then incubated for a further 60 min at room temperature and changes in HTRF fluorescent emission ratio determined according to manufacturer's instructions using an Envision plate reader (Perkin Elmer, Zaventem, Belgium) with laser excitation.

All incubations were performed in duplicate and results were compared to a concentration-effect curve to dopamine. ($10^{-11}$M to $10^{-6}$M).

Data Analysis

Data was analyzed using Excel and PRISM (GraphPad Software) to obtain $pEC_{50}$ and Erel using the 4-parameter logistic equation (DeLean et al, 1978) where Erel is the fitted maximal response of the test compound minus basal expressed as a percentage relative to that obtained with dopamine which was defined as 100%.

When tested in the cAMP HTRF assay, compounds of the Examples exhibit values of pEC50 greater than or equal to 5.5; ideally greater than or equal to 6.5; preferably greater than or equal to 7.0; more preferably greater than or equal to 7.5.

Illustratively, Examples 1-8, 14, 15, 16, 17, 20, 21, 22, 28, 29, 30 and 32 exhibit values of pEC50 greater than or equal to 7.5 and Examples 9, 10, 11, 12, 18, 19, 23, 24, 25, 26, 27 and 31 exhibit values of pEC50 greater than or equal to 7.0 and lower than 7.5.

The invention claimed is:

1. A compound of formula (I), or a pharmaceutically acceptable salt thereof,

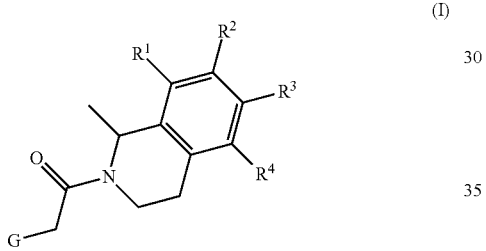

(I)

wherein
- $R^1$, $R^2$ and $R^3$ represent independently hydrogen, halogen or cyano; or $R^1$, $R^2$ and $R^3$ represent independently $C_{1-6}$ alkyl or $C_{1-6}$ alkoxy, either of which groups may be optionally substituted by one or more substituents;
- $R^4$ represents —N=S(O)$R^a R^b$, or $R^4$ represents $C_{1-6}$ alkyl, $C_{1-6}$ alkoxy, $C_{3-8}$ cycloalkyl or $C_{3-7}$heterocycloalkyl, each of these groups which may be optionally substituted by one or more substituents;
- $R^a$ and $R^b$ represent independently $C_{1-6}$ alkyl, which group may be optionally substituted by one or more substituents; or $R^a$ and $R^b$ are linked together to form with the S atom to which they are attached a $C_{3-7}$ heterocycloalkyl, which group may be optionally substituted by one or more substituents;
- G represents a fused heterocyclic system selected from the groups represented by formula ($G^1$), ($G^2$), ($G^3$), ($G^4$), ($G^5$), and ($G^6$),

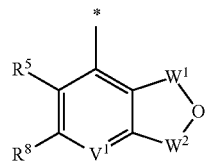

(G$^1$)

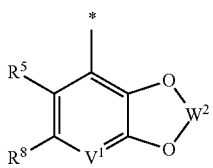

(G$^2$)

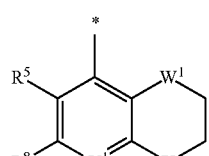

(G$^3$)

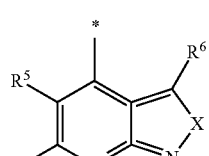

(G$^4$)

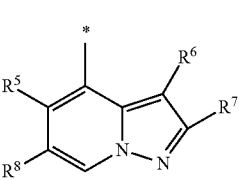

(G$^5$)

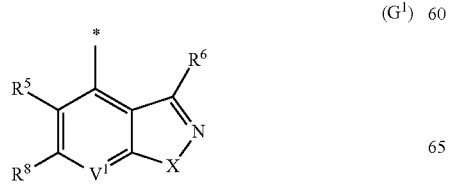

(G$^6$)

wherein
- the asterisk (*) represents the point of attachment of G to the remainder of the molecule;
- $V^1$ represents CH or N;
- $W^1$ and $W^2$ represent independently $CR^9 R^{10}$;
- X represents O or $NR^{11}$;
- $R^5$ represents halogen or cyano: or $R^5$ represents $C_{1-6}$ alkyl or $C_{1-6}$ alkoxy, either of which group may be optionally substituted by one or more substituents;
- $R^6$ and $R^7$ represent independently hydrogen, halogen or cyano; or $R^6$ and $R^7$ represent independently $C_{1-6}$alkyl or $C_{1-6}$ alkoxy, either of these groups which may be optionally substituted by one or more substituents;
- $R^8$ represents hydrogen, halogen or cyano; or $R^8$ represents independently $C_{1-6}$ alkyl, $C_{3-8}$ cycloalkyl or $C_{1-6}$ alkoxy, either of these groups which may be optionally substituted by one or more substituents;
- $R^9$ and $R^{10}$ represent independently hydrogen or halogen; or $R^9$ and $R^{10}$ represent independently $C_{1-6}$ alkyl, which group may be optionally substituted by one or more substituents; and
- $R^{11}$ represents hydrogen; or $R^{11}$ represents $C_{1-6}$alkyl, which group may be optionally substituted by one or more substituents.

2. The compound as claimed in claim 1 represented by formula (IA), or a pharmaceutically acceptable salt thereof,

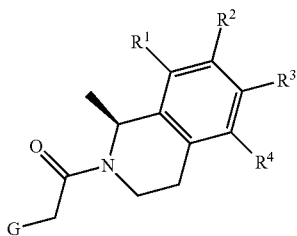

(IA)

3. The compound as claimed in claim 1, or a pharmaceutically acceptable salt thereof, wherein
R¹, R² and R³ represent independently hydrogen, halogen or cyano: or R¹, R² and R³ represent independently unsubstituted $C_{1-6}$ alkyl or unsubstituted $C_{1-6}$ alkoxy; and
R⁴ represents (hydroxy)ethyl, (fluoro)(hydroxy)ethyl, (difluoro)(hydroxy)ethyl, (methyl)(hydroxy)(difluoro)ethyl, (methyl)(hydroxy)(fluoro)ethyl, (hydroxy)(fluoromethyl)(fluoro)ethyl, (methyl)(hydroxy)ethyl, (hydroxy)(methyl)propyl, (hydroxy)(methyl)butyl, (hydroxy)cyclobutyl, (hydroxy)azetidinyl, (hydroxy)piperidinyl, methoxy, ethoxy, propoxy, difluoromethoxy, [(dimethyl)oxido-λ⁶-sulfanilidene]amino-, or [oxido-λ⁴-oxathianylidene]amino-, [oxidotetrahydro-1H-1λ⁴-thiophenylidene]amino.

4. The compound as claimed in claim 1 wherein (G) represents a fused heterocycle represented by formula (G¹), (G⁵) or (G⁶), and
X represents O or NR¹¹;
V¹ represents CH or N;
R¹¹ represents hydrogen or unsubstituted $C_{1-6}$ alkyl;
R⁵ and R⁶ represent independently halogen;
R⁷ represents hydrogen; and
R⁸ represents hydrogen, cyano or unsubstituted $C_{3-8}$ cycloalkyl.

5. The compound as claimed in claim 1 wherein R⁴ represents (hydroxy)ethyl, (fluoro)(hydroxy)ethyl, (difluoro)(hydroxy)ethyl, (methyl)(hydroxy)(difluoro)ethyl, (methyl)(hydroxy)(fluoro)ethyl, (hydroxy)(fluoromethyl)(fluoro)ethyl or (methyl)hydroxy)ethyl.

6. The compound as claimed in claim 1 represented by formula (IC-a), or a pharmaceutically acceptable salt thereof,

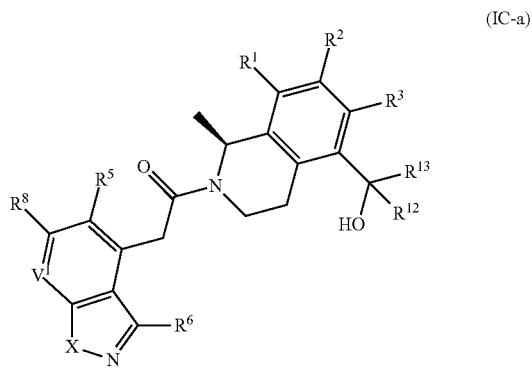

(IC-a)

wherein
R¹, R² and R³ represent independently hydrogen, halogen or cyano; or R¹, R² and R³ represent independently unsubstituted $C_{1-6}$ alkyl or unsubstituted $C_{1-6}$ alkoxy;

X represents O or NR¹¹;
V¹ represents CH or N;
R¹¹ represents hydrogen or unsubstituted $C_{1-6}$ alkyl;
R⁵ and R⁶ represent independently halogen;
R⁸ represents hydrogen, cyano or unsubstituted $C_{3-8}$ cycloalkyl, and
R¹² and R¹³ represent independently hydrogen, deuterium, methyl, fluoromethyl or difluoromethyl.

7. The compound as claimed in claim 1 represented by formula (ID-a), or a pharmaceutically acceptable salt thereof,

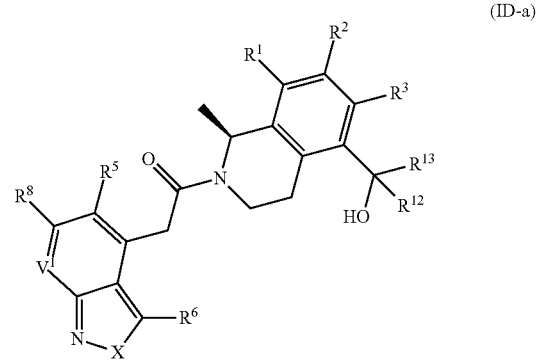

(ID-a)

wherein
R¹, R² and R³ represent independently hydrogen, halogen or cyano or R¹, R² and R³ represent independently unsubstituted $C_{1-6}$ alkyl or unsubstituted $C_{1-6}$ alkoxy;
X represents O or NR¹¹;
V¹ represents CH or N;
R¹¹ represents hydrogen or unsubstituted $C_{1-6}$ alkyl;
R⁵ and R⁶ represent independently halogen;
R⁸ represents hydrogen, cyano or unsubstituted $C_{3-8}$ cycloalkyl, and
R¹² and R¹³ represent independently hydrogen, deuterium, methyl, fluoromethyl or difluoromethyl.

8. The compound as claimed in claim 6 wherein X represents —NR¹¹ and R¹¹ is hydrogen or methyl.

9. The compound as claimed in claim 7 wherein X represents —NR¹¹ and R¹¹ is hydrogen.

10. The compound as claimed in claim 1 represented by formula (IE-a), or a pharmaceutically acceptable salt thereof,

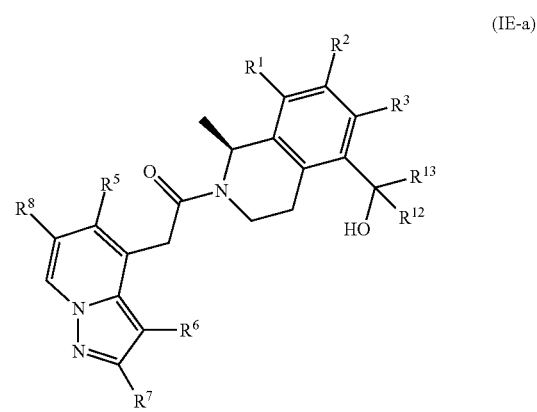

(IE-a)

wherein
R¹, R² and R³ represent independently hydrogen, halogen or cyano; or R¹, R² and R³ represent independently unsubstituted $C_{1-6}$ alkyl or unsubstituted $C_{1-6}$ alkoxy;
R⁵ and R⁶ represent independently halogen;
R⁷ represents hydrogen;
R⁸ represents hydrogen, cyano or unsubstituted $C_{3-8}$ cycloalkyl; and
R¹² and R¹³ represent independently hydrogen, deuterium, methyl, fluoromethyl or difluoromethyl.

11. The compound as claimed in claim 1 wherein R¹, R² and R³ represent independently hydrogen.

12. The compound as claimed in claim 1 wherein R⁵ and R⁶ represent independently chloro.

13. The compound as claimed in claim 1 wherein R⁸ and R⁷ represents hydrogen.

14. The compound as claimed in claim 1 which is selected from the group consisting of
- 2-(3,5-dichloro-1,2-benzoxazol-4-yl)-1-[(1S)-5-[(1S)-2,2-difluoro-1-hydroxy-ethyl]-1-methyl-3,4-dihydro-1H-isoquinolin-2-yl]ethanone;
- 2-(3,5-dichloro-1H-indazol-4-yl)-1-[(1S)-5-[(1R)-2-fluoro-1-hydroxy-1-methyl-ethyl]-1-methyl-3,4-dihydro-1H-isoquinolin-2-yl]ethanone;
- 2-(3,5-dichloro-1H-indazol-4-yl)-1-[(1S)-5-[(1S)-2-fluoro-1-hydroxy-1-methyl-ethyl]-1-methyl-3,4-dihydro-1H-isoquinolin-2-yl]ethanone;
- 2-(3,5-dichloro-1H-indazol-4-yl)-1-[(1S)-5-[(1R)-2,2-difluoro-1-hydroxy-ethyl]-1-methyl-3,4-dihydro-1H-isoquinolin-2-yl]ethanone;
- 2-(3,5-dichloro-1H-indazol-4-yl)-1-[(1S)-5-[(1S)-2,2-difluoro-1-hydroxy-ethyl]-1-methyl-3,4-dihydro-1H-isoquinolin-2-yl]ethanone;
- 2-(3,5-dichloro-1H-imidazol-4-yl)-1-[(1S)-5-[2,2-difluoro-1-hydroxy-1-methyl-ethyl]-1-methyl-3,4-dihydro-1H-isoquinolin-2-yl]ethanone;
- 2-(3,5-dichloro-2-methyl-indazol-4-yl)-1-[(1S)-5-[(1R)-2,2-difluoro-1-hydroxy-ethyl]-1-methyl-3,4-dihydro-1H-isoquinolin-2-yl]ethanone;
- 2-(3,5-dichloro-2-methyl-indazol-4-yl)-1-[(1S)-5-[(1S)-2,2-difluoro-1-hydroxy-ethyl]-1-methyl-3,4-dihydro-1H-isoquinolin-2-yl]ethanone;
- 2-(3,5-dichloro-1-methyl-1H-indazol-4-yl)-1-[(1S)-5-[(1R)-2,2-difluoro-1-hydroxyethyl]-1-methyl-3,4-dihydroisoquinolin-2(1H)-yl]ethanone;
- 2-(3,5-dichloro-1-methyl-1H-indazol-4-yl)-1-[(1S)-5-[(1S)-2,2-difluoro-1-hydroxyethyl]-1-methyl-3,4-dihydroisoquinolin-2(1H)-yl]ethanone;
- 2-(3,5-dichloro-2-methyl-indazol-4-yl)-1-[(1S)-5-[2,2-difluoro-1-hydroxy-1-methyl-ethyl]-1-methyl-3,4-dihydro-1H-isoquinolin-2-yl]ethanone;
- 2-(3,5-dichloro-1H-pyrazolo[3,4-b]pyridin-4-yl)-1-[(1S)-5-[(1S)-2-fluoro-1-hydroxy-1-methyl-ethyl]-1-methyl-3,4-dihydro-1H-isoquinolin-2-yl]ethanone;
- 2-(3,5-dichloro-1H-pyrazolo[3,4-b]pyridin-4-yl)-1-[(1S)-5-[(1R)-2-fluoro-1-hydroxy-1-methyl-ethyl]-1-methyl-3,4-dihydro-1H-isoquinolin-2-yl]ethanone;
- 2-(3,5-dichloro-1H-pyrazolo[3,4-b]pyridin-4-yl)-1-[(1S)-5-[2,2-difluoro-1-hydroxy-1-methyl-ethyl]-1-methyl-3,4-dihydro-1H-isoquinolin-2-yl]ethanone;
- 2-(3,5-dichloro-1H-pyrazolo[3,4-b]pyridin-4-yl)-1-[(1S)-5-[2-fluoro-1-(fluoromethyl)-1-hydroxy-ethyl]-1-methyl-3,4-dihydro-1H-isoquinolin-2-yl]ethanone;
- 2-(3,5-dichloro-1-methyl-pyrazolo[3,4-b]pyridin-4-yl)-1-[(1S)-5-((1R)-2-fluoro-1-hydroxy-1-methyl-ethyl)-1-methyl-3,4-dihydro-1H-isoquinolin-2-yl]ethanone;
- 2-(3,5-dichloro-1-methyl-pyrazolo[3,4-b]pyridin-4-yl)-1-[(1S)-5-((1S)-2-fluoro-1-hydroxy-1-methyl-ethyl)-1-methyl-3,4-dihydro-1H-isoquinolin-2-yl]ethanone;
- 2-(3,5-dichloro-1-methyl-pyrazolo[3,4-b]pyridin-4-yl)-1-[(1S)-5-[2,2-difluoro-1-hydroxy-1-methyl-ethyl]-1-methyl-3,4-dihydro-1H-isoquinolin-2-yl]ethanone;
- 2-(3,5-dichloro-1-methyl-pyrazolo[3,4-b]pyridin-4-yl)-1-[(1S)-5-[2-fluoro-1-(fluoromethyl)-1-hydroxy-ethyl]-1-methyl-3,4-dihydro-1H-isoquinolin-2-yl]ethanone;
- 2-(3,5-dichloro-1-methyl-indazol-4-yl)-1-[(1S)-5-[(1R)-2-fluoro-1-hydroxy-1-methyl-ethyl]-1-methyl-3,4-dihydro-1H-isoquinolin-2-yl]ethanone;
- 2-(3,5-dichloro-1-methyl-indazol-4-yl)-1-[(1S)-5-[(1S)-2-fluoro-1-hydroxy-1-methyl-ethyl]-1-methyl-3,4-dihydro-1H-isoquinolin-2-yl]ethanone;
- 2-(3,5-dichloro-1-methyl-indazol-4-yl)-1-[(1S)-5-[2,2-difluoro-1-hydroxy-1-methyl-ethyl]-1-methyl-3,4-dihydro-1H-isoquinolin-2-yl]ethanone;
- 2-(3,5-dichloro-1-methyl-indazol-4-yl)-1-[(1S)-5-[2-fluoro-1-(fluoromethyl)-1-hydroxy-ethyl]-1-methyl-3,4-dihydro-1H-isoquinolin-2-yl]ethanone;
- 2-(3,5-dichloropyrazolo[1,5-a]pyridin-4-yl)-1-[(1S)-5-[(1S)-2-fluoro-1-hydroxy-1-methyl-ethyl]-1-methyl-3,4-dihydro-1H-isoquinolin-2-yl]ethanone;
- 2-(3,5-dichloropyrazolo[1,5-a]pyridin-4-yl)-1-[(1S)-5-[(1S)-2,2-difluoro-1-hydroxy-1-methyl-ethyl]-1-methyl-3,4-dihydro-1H-isoquinolin-2-yl]ethanone;
- 2-(3,5-dichloro-6-cyclopropyl-pyrazolo[1,5-a]pyridin-4-yl)-1-[(1S)-5-(2,2-difluoro-1-hydroxy-1-methyl-ethyl)-1-methyl-3,4-dihydro-1H-isoquinolin-2-yl]ethanone; and
- 3,5-dichloro-4-[2-[(1S)-5-(2,2-difluoro-1-hydroxy-1-methyl-ethyl)-1-methyl-3,4-dihydro-1H-isoquinolin-2-yl]-2-oxo-ethyl]pyrazolo[1,5-a]pyridine-6-carbonitrile.

15. A method of treating a subject with a disease or condition mediated by a D1 receptor, the method comprising administering to the subject a therapeutically effect amount of a compound according to claim 1, or a pharmaceutically acceptable salt thereof.

16. The method according to claim 15, wherein the disease or condition is cognitive and negative symptoms in schizophrenia, cognitive and negative symptoms in schizophrenia, cognitive impairment related to classical antipsychotic therapy, impulsivity, attention disorder with hyperactivity (ADHD), Parkinson's disease and related movement disorders, dystonia, Huntington's disease, dementia with Lewy Body, Alzheimer's disease, age-related cognitive decline, mild cognitive impairment (MCI), drug addiction, sleep disorders or apathy.

17. A pharmaceutical composition comprising a compound according to claim 1, or a pharmaceutically acceptable salt thereof, in association with a pharmaceutically acceptable carrier.

* * * * *